(12) United States Patent
Aoki et al.

(10) Patent No.: US 11,680,943 B2
(45) Date of Patent: Jun. 20, 2023

(54) ELECTRIC FIELD STIRRING APPARATUS, ELECTRIC FIELD STIRRING METHOD, AND PATHOLOGICAL SAMPLE MANUFACTURING APPARATUS

(71) Applicant: Seiko Epson Corporation, Tokyo (JP)

(72) Inventors: Taro Aoki, Niigata (JP); Tadashi Sato, Ugo (JP); Yoichi Suzuki, Yuzawa (JP); Junya Enomoto, Yuzawa (JP)

(73) Assignee: SEIKO EPSON CORPORATION

( * ) Notice: Subject to any disclaimer, the term of this patent is extended or adjusted under 35 U.S.C. 154(b) by 879 days.

(21) Appl. No.: 16/590,499

(22) Filed: Oct. 2, 2019

(65) Prior Publication Data
US 2020/0110078 A1    Apr. 9, 2020

(30) Foreign Application Priority Data

Oct. 3, 2018  (JP) .............................. JP2018-188001

(51) Int. Cl.

| G01N 1/00 | (2006.01) |
|---|---|
| G01N 33/53 | (2006.01) |
| G01N 1/31 | (2006.01) |
| G01N 33/543 | (2006.01) |
| G01N 1/38 | (2006.01) |
| B01F 33/05 | (2022.01) |
| B01F 33/302 | (2022.01) |
| B01F 33/3031 | (2022.01) |

(52) U.S. Cl.
CPC ......... *G01N 33/5302* (2013.01); *B01F 33/05* (2022.01); *B01F 33/051* (2022.01); *B01F 33/3021* (2022.01); *B01F 33/3031* (2022.01); *G01N 1/31* (2013.01); *G01N 1/38* (2013.01); *G01N 33/5438* (2013.01)

(58) Field of Classification Search
None
See application file for complete search history.

(56) References Cited

U.S. PATENT DOCUMENTS

| 2010/0173300 A1 | 7/2010 | Akagami et al. |
| 2015/0233902 A1* | 8/2015 | Akagami ................. B01L 9/52 435/7.1 |
| 2019/0195756 A1 | 6/2019 | Aoki et al. |

FOREIGN PATENT DOCUMENTS

| JP | 2010-119388 A | 6/2010 |
| JP | 2014-054601 A | 3/2014 |
| JP | 2016-109636 A | 6/2016 |
| JP | 2018-040788 A | 3/2018 |
| JP | 6354114 B1 | 7/2018 |
| JP | 2018-139504 A | 9/2018 |

* cited by examiner

*Primary Examiner* — Jyoti Nagpaul

(74) *Attorney, Agent, or Firm* — Harness, Dickey & Pierce, P.L.C.

(57) ABSTRACT

An electric field stirring apparatus, in which a droplet as a liquid disposed between a first electrode and a second electrode disposed to face each other is vibrated and stirred by an electric field generated between the first electrode and the second electrode, the second electrode having a groove formed along a first direction on an electrode surface facing the first electrode, includes a movement mechanism that reciprocally moves the first electrode relative to the second electrode in a second direction intersecting the first direction in a state in which the first electrode and the second electrode face each other during a period in which the electric field is generated.

11 Claims, 29 Drawing Sheets

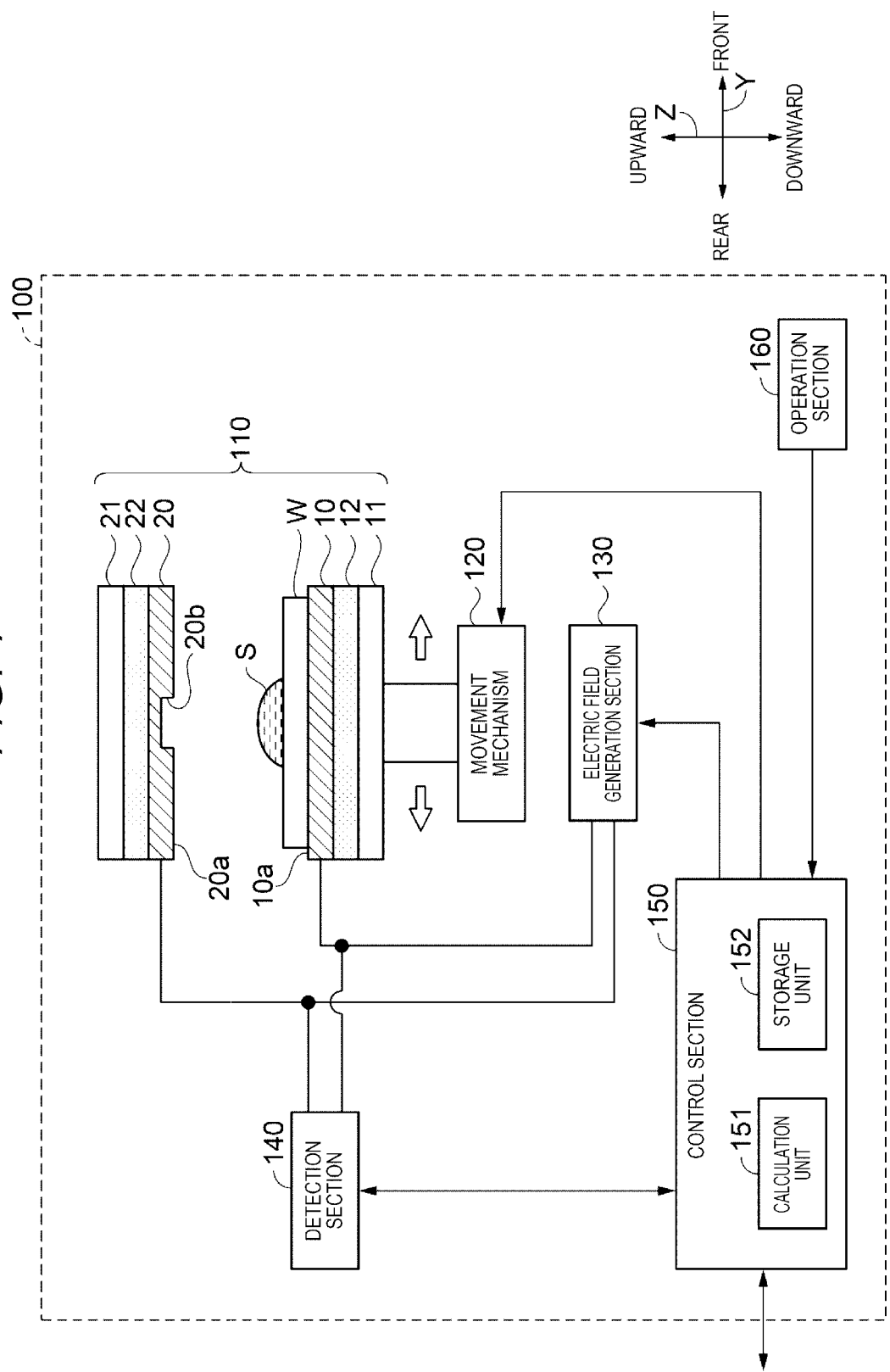

ELECTRIC FIELD STIRRING APPARATUS, ELECTRIC FIELD STIRRING METHOD, AND PATHOLOGICAL SAMPLE MANUFACTURING APPARATUS

The present application is based on, and claims priority from, JP Application Serial Number 2018-188001, filed Oct. 3, 2018, the disclosure of which is hereby incorporated by reference herein in its entirety.

BACKGROUND

1. Technical Field

The present disclosure relates to an electric field stirring apparatus, an electric field stirring method, and a pathological sample manufacturing apparatus.

2. Related Art

In recent years, with the development of biotechnology, various devices used for research and the like have been developed. For example, in the pathology field, automation of a staining process has progressed in immunostaining performed to detect an antigen that is a kind of protein in a tissue sample. Specifically, an electric field stirring apparatus capable of speeding up a primary/secondary antigen-antibody reaction process and an electric field stirring method using the same are disclosed (JP-A-2016-109636).

The electric field stirring apparatus disclosed in JP-A-2016-109636 is an apparatus that stirs a liquid disposed between a first electrode and a second electrode due to an electric field generated between the first electrode and the second electrode, and the second electrode has a first portion and a second portion of which inter-electrode distances between the first electrode and the second electrode are different from each other when the second electrode faces the first electrode. A configuration forming the first portion and the second portion having different inter-electrode distances may be a groove or a protrusion formed on the second electrode. According to the configuration of the electric field stirring apparatus disclosed in JP-A-2016-109636, in the first portion and the second portion having different inter-electrode distances, a state occurs in which a field intensity of the other is stronger than that of one or a field intensity of the other is weaker than that of one, and thus vibration of a liquid is increased by an electric field more than in a case where an electric field with a constant intensity is applied to the liquid, and thus the liquid can be efficiently stirred.

However, in the electric field stirring method using the electric field stirring apparatus in JP-A-2016-109636, a vibration state of a liquid can be increased by an electric field, but there is a problem in that it cannot necessarily be said that a stirring state of the liquid is uniform. Specifically, when, for example, a reagent related to an antigen-antibody reaction, as a liquid disposed on a substrate between the first electrode and the second electrode, is vibrated and stirred by Coulomb force based on the electric field, there is an occurrence of a portion in which the reagent is favorably stirred and a reaction progresses, and a portion in which stirring at apart corresponding to a node of vibration is weaker than at other parts, and thus a reaction hardly progresses. When the reagent is colored by using a coloring reagent after the antigen-antibody reaction, coloring unevenness occurs depending on a progress state of the antigen-antibody reaction. There is concern that coloring unevenness in immunohistochemistry (IHC) may reduce the accuracy of diagnosis. In an In Situ Hybridization (ISH) method of examining gene expression in a cell or tissue, diagnosis is performed based on a state of a colored portion indicating the presence of an expressed gene for the whole cell or tissue, and thus it is necessary to remove coloring unevenness by uniformizing a stirring state not only in a case of IHC but also in a case of ISH.

SUMMARY

An electric field stirring apparatus according to an aspect of the present disclosure is an electric field stirring apparatus in which a liquid disposed between a first electrode and a second electrode disposed to face each other is vibrated and stirred by an electric field generated between the first electrode and the second electrode, the second electrode having a groove formed along a first direction on an electrode surface facing the first electrode. The electric field stirring apparatus includes a movement mechanism that reciprocally moves at least one of the first electrode and the second electrode relative to the other electrode in a second direction intersecting the first direction in a state in which the first electrode and the second electrode face each other during a period in which the electric field is generated.

In the electric field stirring apparatus, the liquid may be disposed in a predetermined region on one surface of a substrate, the first electrode has a mounting portion on which the substrate is mounted, and, when a position where a center of the predetermined region of the substrate mounted on the mounting portion of the first electrode faces a center of the groove of the second electrode is set as an origin in the second direction, the movement mechanism may reciprocally move the one electrode in the second direction relative to the other electrode to a position where an inner edge of the predetermined region is deviated relative to the origin.

In the electric field stirring apparatus, a plurality of the grooves may be formed with a predetermined arrangement pitch in the second direction on the electrode surface of the second electrode, and the predetermined region in which the liquid is disposed may be provided in a plurality with the predetermined arrangement pitch in the second direction on the one surface of the substrate.

The electric field stirring apparatus may further include an electric field generation section that periodically applies a voltage between the first electrode and the second electrode so as to generate an electric field; a detection section that detects the voltage applied between the first electrode and the second electrode; and a control section, and the control section may control the electric field generation section such that a value of the voltage detected by the detection section is included in a predetermined range.

In the electric field stirring apparatus, the predetermined range of the value of the voltage may be ±5% of a predetermined voltage value.

An electric field stirring method according to another aspect of the present disclosure includes an electric field stirring step in which a liquid disposed between a first electrode and a second electrode disposed to face each other is vibrated and stirred by an electric field generated between the first electrode and the second electrode, in which the second electrode has a groove formed along a first direction on an electrode surface facing the first electrode, and in the electric field stirring step, at least one of the first electrode and the second electrode is reciprocally moved relative to the other electrode in a second direction intersecting the first direction in a state in which the first electrode and the second electrode face each other during a period in which the electric field is generated.

In the electric field stirring method, the liquid may be disposed in a predetermined region on one surface of a substrate, and, in the electric field stirring step, when a position where a center of the predetermined region of the substrate mounted on the first electrode faces a center of the groove of the second electrode is set as an origin in the second direction, the one electrode may be reciprocally moved in the second direction relative to the other electrode to a position where an outer edge of the predetermined region is deviated relative to the origin.

In the electric field stirring method, a plurality of the grooves may be formed with a predetermined arrangement pitch in the second direction on the electrode surface of the second electrode, and the predetermined region in which the liquid is disposed may be provided in a plurality with the predetermined arrangement pitch in the second direction on the one surface of the substrate.

In the electric field stirring method, in the electric field stirring step, a voltage may be periodically applied between the first electrode and the second electrode so as to generate an electric field, and the voltage may be applied such that a value of the voltage applied between the first electrode and the second electrode is included in a predetermined range.

A pathological sample manufacturing apparatus according to still another aspect of the present disclosure includes the electric field stirring apparatus; a stage section that includes a stage which functions as the first electrode of the electric field stirring apparatus and on which a substrate with a tissue sample fixed to a predetermined region is mounted; a reagent supply section that supplies a reagent to the substrate mounted on the stage; a cleaning section that supplies a cleaning liquid to the substrate mounted on the stage; a stage transport mechanism that functions as the movement mechanism of the electric field stirring apparatus when the cleaning section, the reagent supply section, and the electric field stirring apparatus are disposed in the second direction, and moves the stage in the second direction; and a control unit, in which, based on a pathological sample manufacturing protocol, the control unit controls driving of the stage transport mechanism, thus moves the stage to a position facing the second electrode of the electric field stirring apparatus, and subjects the reagent or the cleaning liquid supplied to the substrate to electric field stirring.

The pathological sample manufacturing apparatus may further include a plurality of stage sections, the stage transport mechanism may be provided to correspond to each of the plurality of stage sections, and the second electrode of the electric field stirring apparatus may be separately provided for each of the plurality of stage sections.

The pathological sample manufacturing apparatus may further include a probe that is brought into contact with the stage transported to the electric field stirring apparatus by the stage transport mechanism, and that applies a potential for generating an electric field, and the electric field stirring apparatus may include a probe movement mechanism that reciprocally moves the probe in the second direction in a state in which the probe is brought into contact with the stage.

BRIEF DESCRIPTION OF THE DRAWINGS

FIG. 1 is a schematic diagram illustrating an electrical and mechanical configuration of an electric field stirring apparatus of a first embodiment.

DESCRIPTION OF EXEMPLARY EMBODIMENTS

Figure 2A:
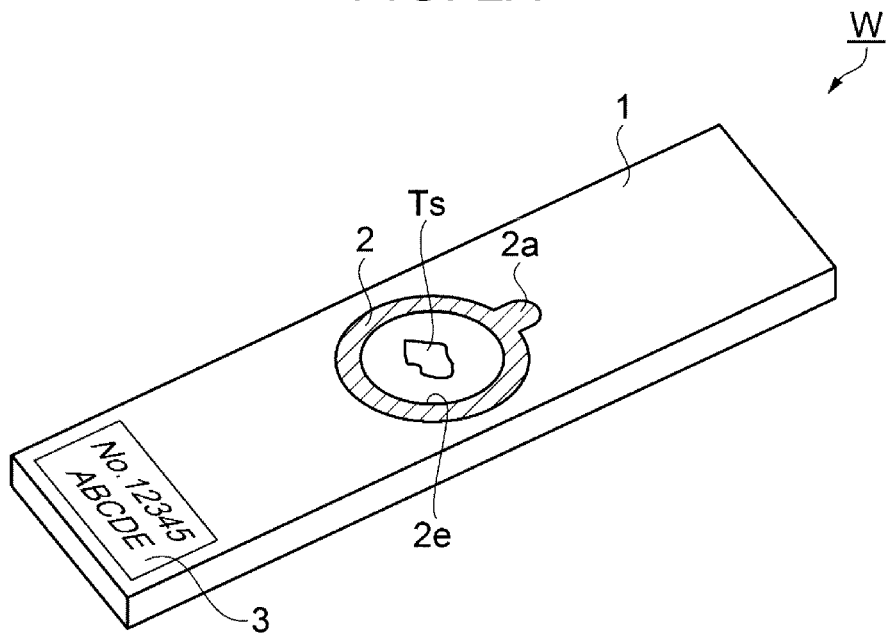
FIG. 2A is a perspective view illustrating a workpiece to which a tissue sample is fixed.

Hereinafter, embodiments of the present disclosure will be described with reference to the drawings. Throughout the drawings, a described portion is displayed to be enlarged or reduced as appropriate such that the portion has a size sufficient to be recognized. In an electric field stirring apparatus according to an embodiment of the present disclosure described below, a small amount of liquid is disposed between a pair of electrodes, and an electric field is generated by periodically applying voltages to the pair of electrodes. In the electric field stirring apparatus, the liquid is vibrated and stirred by Coulomb force based on the electric field.

First Embodiment

Electric Field Stirring Apparatus

An electric field stirring apparatus of the present embodiment will be described with reference to FIG. 1. FIG. is a schematic diagram illustrating an electrical and mechanical configuration of an electric field stirring apparatus of a first embodiment.

An electric field stirring apparatus 100 of the present embodiment is configured to include a stirring section 110, a movement mechanism 120, an electric field generation section 130, a detection section 140, a control section 150, and an operation section 160. The stirring section 110 includes a first electrode 10 and a second electrode 20 disposed to face each other, and a workpiece W on which a droplet S that is a liquid is disposed is mounted on a surface of the first electrode 10. The first electrode 10 is supported at an electrode support portion 11 via an insulating portion 12. The second electrode 20 is supported by an electrode support portion 21 via an insulating portion 22 so as to face the first electrode 10. A material forming the first electrode 10 and the second electrode 20 is, for example, aluminum. A groove 20b is formed on an electrode surface 20a of the second electrode 20 facing the first electrode 10.

The electric field stirring apparatus 100 has a casing in which the stirring section 110, the movement mechanism 120, the electric field generation section 130, the detection section 140, the control section 150, and the operation section 160. The casing is provided with a door (not illustrated) through which the workpiece W is loaded onto and unloaded from the stirring section 110. The electric field stirring apparatus 100 includes a power source section (not illustrated) supplying power for driving each mechanism or each section.

With respect to the stirring section 110, the movement mechanism 120 and the electric field generation section 130 are provided under the stirring section 110. The operation section 160 is provided in front of the stirring section 110. The detection section 140 and the control section 150 are provided behind the stirring section 110. Hereinafter, on the drawings, a vertical direction in which the first electrode 10 and the second electrode 20 are disposed to face each other is set to an upward-downward direction or a Z direction, and a direction of front and rear in the apparatus is set to a front-rear direction or a Y direction. Although not illustrated in FIG. 1, a direction of left and right orthogonal to the upward-downward direction and the front-rear direction is set to a leftward-rightward direction or an X direction.

The movement mechanism 120 is configured to be able of move the electrode support portion 11 supporting the first electrode 10 in the front-rear direction (Y direction). A configuration of the movement mechanism 120 is not particularly limited, but may be a configuration of including, for example, a guide that guides the electrode support portion 11 to be movable in the front-rear direction, and a motor as a drive source of the guide.

The electric field generation section 130 is electrically coupled to the first electrode 10 and the second electrode 20, and periodically applies a voltage between the first electrode 10 and the second electrode 20 so as to generate an electric field. Specifically, the electric field generation section 130 generates, for example, a rectangular wave electric signal of which a voltage periodically changes between 0 volts (V) and 4 kilovolts (kV). A frequency of the electric signal is, for example, 5 hertz (Hz). The first electrode 10 is electrically coupled to, for example, the ground (GND), and the electric field generation section 130 applies the electric signal to the second electrode 20. A voltage of an electric signal or setting of a frequency is not limited thereto, and is set as appropriate by taking into consideration physical properties such as an amount, viscosity, or surface tension of a liquid to be stirred.

The detection section 140 detects a voltage of the electric signal generated by the electric field generation section 130. Specifically, the detection section 140 detects a voltage level of the electric signal in a state of being reduced to, for example, 1/1000, and feeds back a detection result to the control section 150 at an interval of one cycle.

The operation section 160 is provided with operation buttons such as a stirring start button and a stirring stop button for operating the electric field stirring apparatus 100. Consequently, the control section 150 electrically coupled to the operation section 160 controls driving of each section of the electric field stirring apparatus 100, and performs an operation corresponding to an operation button. The control section 150 controls driving of the electric field generation section 130 based on an operation from the operation section 160, to apply a voltage between the first electrode 10 and the second electrode 20 and thus to generate an electric field between the first electrode 10 and the second electrode 20. The control section 150 controls driving of the movement mechanism 120 in a period in which the electric field generation section 130 generates the electric field between the first electrode 10 and the second electrode 20, and reciprocally moves the first electrode 10 relative to the second electrode 20 in the front-rear direction (Y direction) in a state in which the first electrode 10 and the second electrode 20 face each other. In other words, stirring of the droplet S as a liquid due to the electric field generated between the first electrode 10 and the second electrode 20 is performed according to reciprocal movement of the first electrode 10 in the front-rear direction (Y direction). The reciprocal movement of the first electrode 10 is performed based on the groove 20b provided on the electrode surface 20a of the second electrode 20. Detailed contents of such an electric field stirring method will be described later.

The control section 150 includes a calculation unit 151 and a storage unit 152, and automatically executes the driving control of each section based on a stirring program stored in advance in the storage unit 152. The stirring program includes stirring conditions that are set according to the type, physical properties (for example, viscosity and surface tension), a volume, and a weight of the droplet S as a liquid disposed on the workpiece W. The storage unit 152 stores not only the stirring program but also various control programs for the electric field stirring apparatus 100. The storage unit 152 may be accessed from the outside via an interface provided on the control section 150 such that the programs are viewed or corrected, or other programs are added. Regarding access from the outside, an access code or the like may be set from the viewpoint of ensuring of security.

The control section 150 controls the electric field generation section 130 to generate an electric signal with a predetermined voltage based on a detection result of a voltage of an electric signal in the detection section 140. Specifically, a variation range of a voltage is controlled to be within ±5% with respect to a preset value of the voltage.

Method of Forming Workpiece W

Next, with reference to FIGS. 2A and 2B, a description will be made of a method of forming the workpiece W. The workpiece W used in the present embodiment is a pathological sample manufactured in a pathological department in order to obtain important information regarding diagnosis, prognosis, and medical treatment selection for a patient. A pathological sample manufacturing method may include an immunohistochemistry (IHC) method in which a worker observes an amount of expressed protein in tissue or a cell while viewing a shape of the tissue or the cell as a tissue sample, or an In Situ Hybridization (ISH) method in which a worker observes an amount of an expressed gene in tissue or a cell.

Figure 2B:
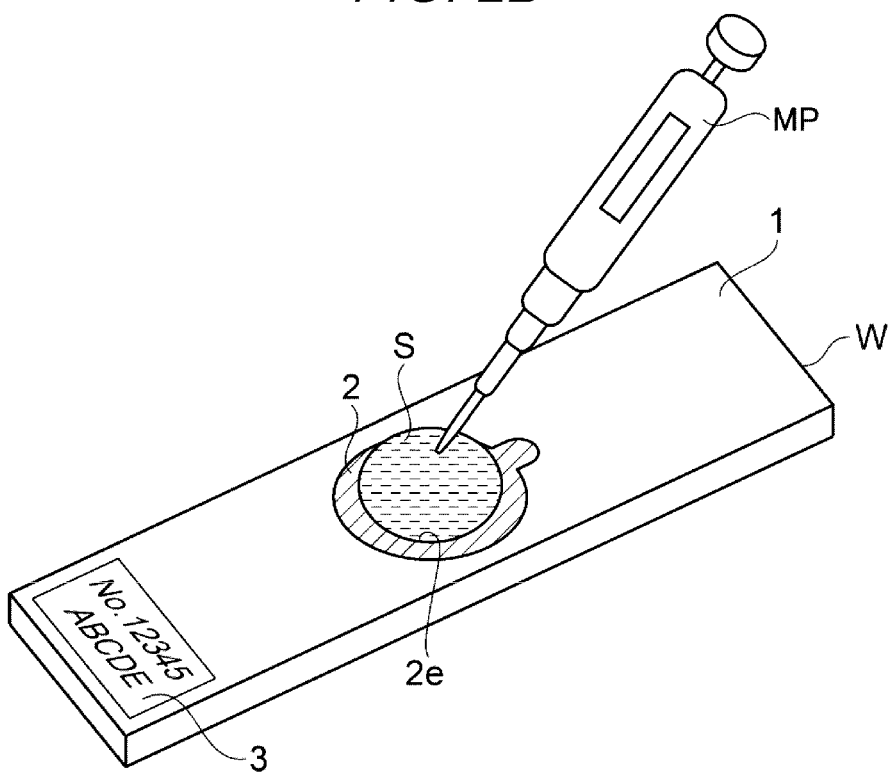
FIG. 2B is a perspective view illustrating a workpiece on which a droplet as a liquid is formed.

FIG. 2A is a perspective view illustrating a workpiece to which a tissue sample is fixed, and FIG. 2B is a perspective view illustrating a workpiece on which a droplet as a liquid is formed. As illustrated in FIG. 2A, a tissue sample Ts used to manufacture a pathological sample is fixed to a substrate 1. As the substrate 1, a colorless and transparent slide glass for a microscope having a width of 26 mm, a length of 76 mm, and a thickness of 1.1 mm, which is standardized in JIS R 3703:1998, is used. A water repellent ring 2 formed of an adhesive seal is stuck to the substrate 1 so as to hold a solution such as a reagent supplied to the fixed tissue sample Ts in a predetermined region 2e. The water repellent ring 2 has a tab 2a protruding from the outer circumference thereof. A worker may pinch the tab 2a so as to stick the water repellent ring 2 to the substrate 1, or pinch the tab 2a so as to peel off the water repellent ring 2 stuck to the substrate 1. The tissue sample Ts is a section of sliced tissue, and is fixed inside the water repellent ring 2. The water repellent ring 2 may be formed by coating the substrate 1 with a water repellent in a ring shape. The water repellent ring 2 may be formed to surround the tissue sample Ts on the substrate 1 to which the tissue sample Ts is fixed. A shape of the water repellent portion is not limited to a circular shape, and may be a polygonal shape such as a quadrilateral shape.

A marking region 3 for identifying the fixed tissue sample Ts is provided on the substrate 1 at one end side in a longitudinal direction of the substrate 1. A worker may stick, for example, a seal on which the name or a management number of the fixed tissue sample Ts is written to the marking region 3, and may form a coating surface on which the name or a management number of the fixed tissue sample Ts is writable.

As illustrated in FIG. 2B, a reagent as a liquid is ejected in a predetermined amount to form the droplet S by using a micropipette MP or the like in the predetermined region 2e defined by the water repellent ring 2. A size of the predetermined region 2e defined by the water repellent ring is, for example, Φ12 mm or ϕ 20 mm. A size of the predetermined region 2e, that is, a size of the water repellent ring 2 is set according to a size of the tissue sample Ts or an amount of a reagent to be reacted with the tissue sample Ts.

The water repellent ring 2 is not limited to being formed alone on the substrate 1, and may be formed in a plurality. For example, two water repellent rings 2 may be formed, a positive tissue sample may be fixed inside one water repellent ring 2, and a comparative negative tissue sample may be fixed inside the other water repellent ring 2.

Electric Field Stirring Method

Figure 3A:
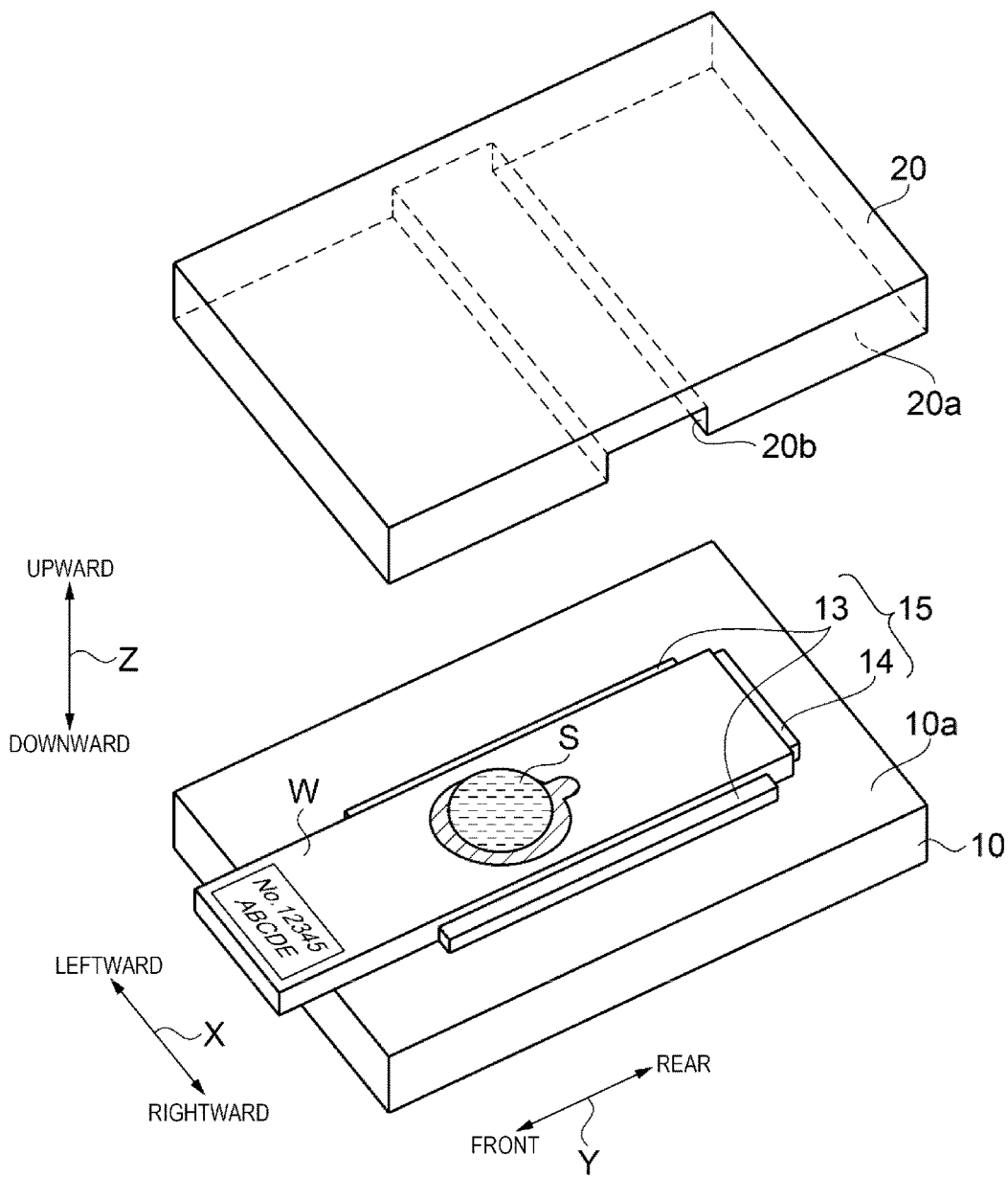
FIG. 3A is a perspective view illustrating a state of a workpiece set in a stirring section.

Next, with reference to FIGS. 3A, 3B, 4A, 4B, and 5, a description will be made of an electric field stirring method of the present embodiment. FIG. 3A is a perspective view illustrating a state of a workpiece set in a stirring section, and FIG. 3B is a sectional view illustrating a state of the workpiece set in the stirring section.

A worker mounts the workpiece W on the first electrode 10 in order to stir the droplet S of the workpiece W. Specifically, as illustrated in FIG. 3A, a pair of guide portions 13 that are disposed along the front-rear direction (Y direction) of the first electrode 10 and are disposed with a gap in the leftward-rightward direction (X direction), and a stop portion 14 disposed along the leftward-rightward direction (X direction) on the rear side of the first electrode 10 in the front-rear direction (Y direction) are provided on an electrode surface 10a of the first electrode 10. When the workpiece W is slid along the pair of guide portions 13 on the first electrode 10, and is butted against the stop portion 14 so as to be disposed, one end of the workpiece W in the longitudinal direction is disposed to protrude from the front end of the first electrode 10. In other words, the pair of guide portions 13 and the stop portion 14 in the first electrode 10 function as a positioning portion 15 for the workpiece W. In other words, the first electrode 10 has a mounting portion for the workpiece W configured with the electrode surface 10a and the positioning portion 15. One end of the workpiece W in the longitudinal direction is disposed to protrude from the front end of the first electrode 10, and thus the worker can hold the protruding one end of the workpiece W and easily remove the workpiece W from the first electrode 10 after the end of stirring. Therefore, the workpiece W can be easily set or reset onto the first electrode 10.

The groove 20b is formed along the leftward-rightward direction (X direction) on the electrode surface 20a of the second electrode 20 disposed to face the first electrode 10 in the upward-downward direction (Z direction).

Figure 3B:
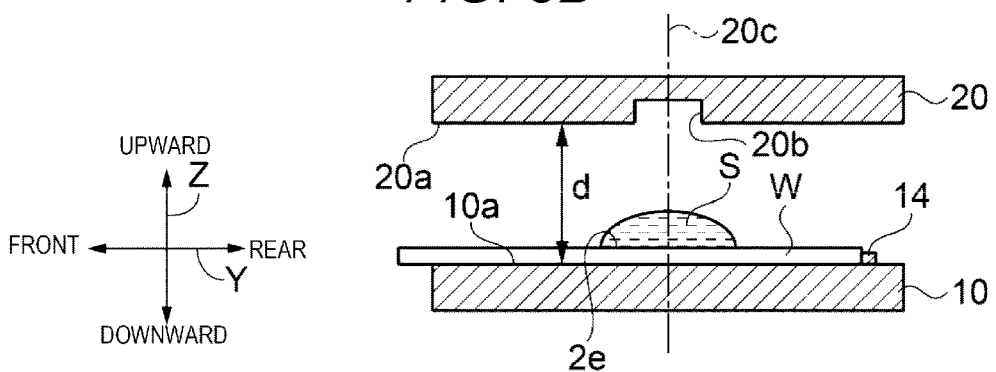
FIG. 3B is a sectional view illustrating a state of the workpiece set in the stirring section.

As illustrated in FIG. 3B, the electrode surface 20a of the second electrode 20 is disposed to face, in the upward-downward direction (Z direction), the electrode surface 10a of the first electrode 10 on which the workpiece W is mounted, with an inter-electrode distance d. In this case, the second electrode 20 is disposed with respect to the first electrode 10 such that the droplet S formed on the workpiece W faces the groove 20b of the second electrode 20. A central line 20c passing through the center of the groove 20b in the front-rear direction (Y direction) overlaps the center of the predetermined region 2e in which the droplet S defined by the water repellent ring 2 is formed on the workpiece W when viewed from leftward-rightward direction (X direction). A position of the central line 20c in the front-rear direction (Y direction) is the origin when the first electrode 10 and the second electrode 20 are disposed to face each other in the electric field stirring method of the present embodiment. A width of the groove 20b of the second electrode 20 in the front-rear direction (Y direction) is, for example, 8 mm. A depth of the groove 20b from the electrode surface 20a is, for example, 4 mm. As described above, when a plurality of water repellent rings 2 are formed on the substrate 1, a plurality of grooves 20b are formed on the electrode surface 20a of the second electrode 20 in correspondence with the plurality of water repellent rings 2.

Figure 4A:
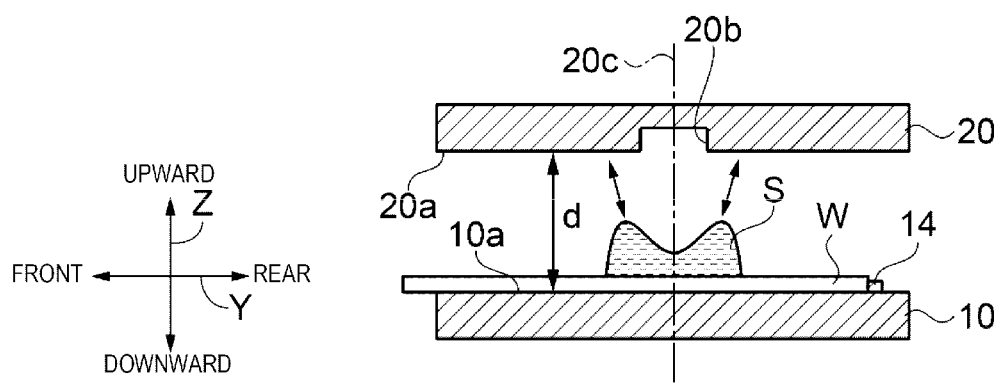
FIG. 4A is a sectional view illustrating an electric field stirring state of the droplet.
Figure 4B:
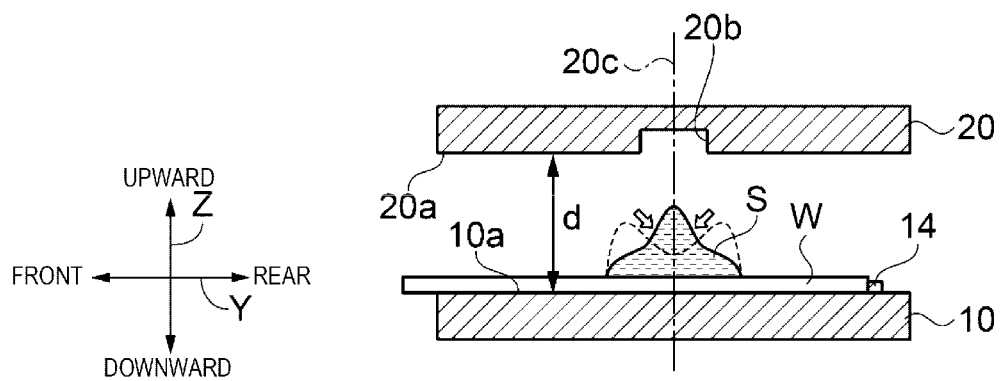
FIG. 4B is a sectional view illustrating an electric field stirring state of the droplet.

FIGS. 4A and 4B are sectional views illustrating an electric field stirring state of the droplet. As illustrated in FIG. 4A, a bottom of the groove 20b of the second electrode 20 has a longer inter-electrode distance than other portions of the second electrode 20. Therefore, when an electric field is generated between the first electrode 10 and the second electrode 20 at the origin where the groove 20b and the droplet S are disposed to face each other on the central line 20c, an intensity of an electric field generated between the first electrode 10 and the groove 20b of the second electrode 20 is weaker than intensities of other portions. In other words, intensities of electric fields generated between portions other than the groove 20b of the second electrode 20 and the first electrode 10 are stronger. The droplet S can be attracted toward the second electrode 20 so as to extend obliquely upward toward the electrode surface 20a on both sides with the groove 20b interposed therebetween, by Coulomb force of electric fields generated with the groove 20b interposed therebetween.

As described above, since an electric signal of which a voltage periodically changes is applied to the second electrode 20 from the electric field generation section 130, when a potential of the second electrode 20 becomes 0 V, the potential is the same as a potential of the first electrode 10, and thus an electric field is not generated between the first electrode 10 and the second electrode 20. Therefore, as illustrated in FIG. 4B, a portion of the droplet S that extends obliquely upward to be attracted toward the second electrode 20 due to the electric field falls down to be collected at the center side by its own weight when the electric field disappears. Such a change in the shape of the droplet S periodically occurs in synchronization with a frequency of the electric signal, and thus the droplet S is periodically vibrated in the upward-downward direction (Z direction) so as to be stirred due to the electric field generated between the first electrode 10 and the second electrode 20. Such a stirring state of the droplet S will be referred to as electric field stirring in the present specification. The inter-electrode distance d between the first electrode 10 and the second electrode 20 is set to a distance in which the droplet S vibrated in the upward-downward direction due to the electric field stirring does not come into contact with the second electrode 20.

In the electric field stirring of the droplet S, since the droplet S is periodically vibrated in the upward-downward direction (Z direction), the droplet S is strongly stirred in a portion separate from a node of vibration of the droplet S, but the droplet S is weakly stirred in the node of the vibration and the vicinity of the node. Therefore, in order to uniformize a stirring state of the droplet S, in the electric field stirring method of the present embodiment, the first electrode 10 is reciprocally moved in the front-rear direction (Y direction) relative to the second electrode 20.

Figure 5:
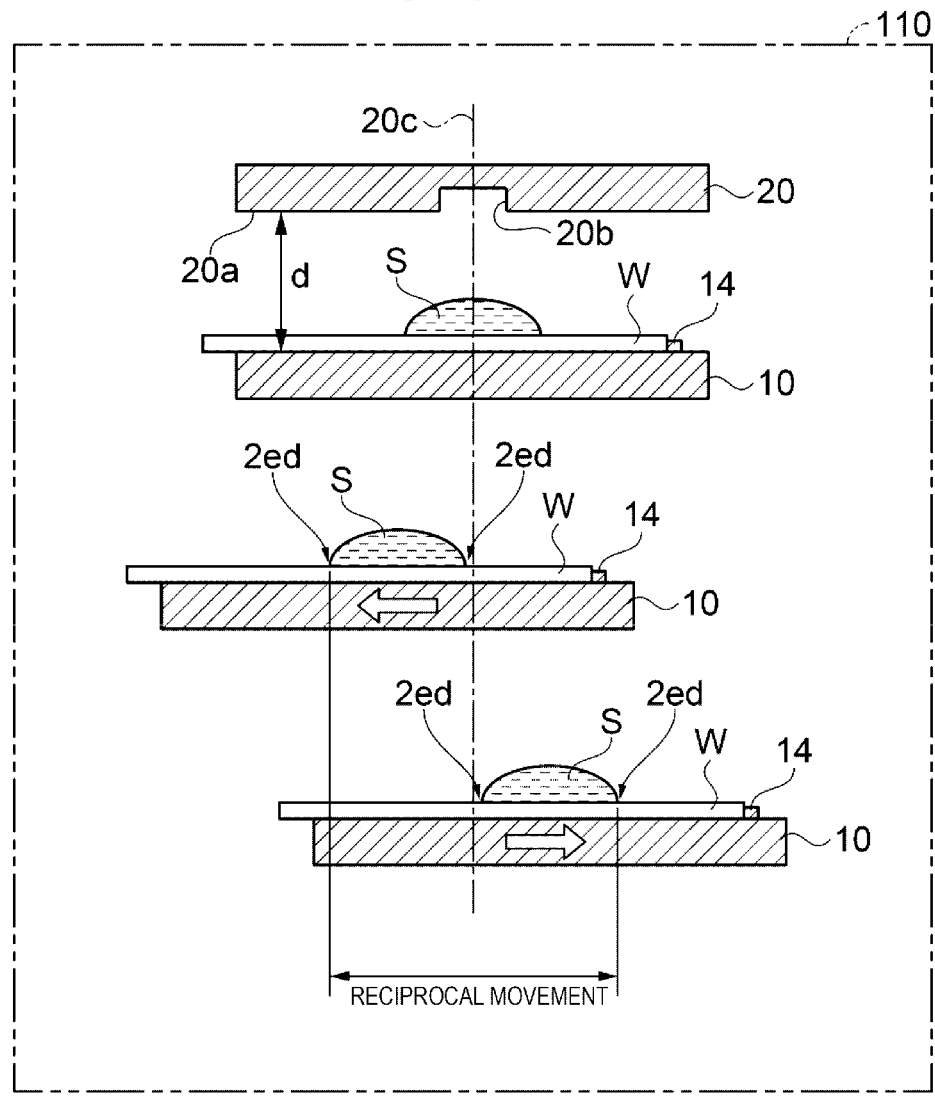
FIG. 5 is a sectional view illustrating a method in which a first electrode is reciprocally moved relative to a second electrode in electric field stirring.

FIG. 5 is a sectional view illustrating a method in which the first electrode is reciprocally moved relative to the second electrode in electric field stirring. As illustrated in FIG. 5, the electric field stirring method of the present embodiment includes an electric field stirring process in which the droplet S as a liquid disposed between the first electrode 10 and the second electrode 20 disposed to face each other is vibrated and stirred due to an electric field generated between the first electrode 10 and the second electrode 20. The second electrode 20 has the groove 20b formed along the leftward-rightward direction (X direction) as a first direction on the electrode surface 20a on the side thereof facing the first electrode 10. In the electric field stirring process, the first electrode 10 is reciprocally moved in the front-rear direction (Y direction) as a second direction orthogonal to the leftward-rightward direction (X direction) in a state in which the first electrode 10 and the second electrode 20 face each other during a period in which an electric field is generated.

In the electric field stirring method using the electric field stirring apparatus 100, the movement mechanism 120 reciprocally moves the first electrode 10 in the front-rear direction (Y direction) to a position where an outer edge 2ed of the predetermined region 2e is deviated relative to the origin, with a position indicated by the central line 20c on which the center of the predetermined region 2e in the droplet S of the workpiece W mounted on the first electrode 10 faces the center of the groove 20b of the second electrode 20 as the origin in the front-rear direction (Y direction). Regarding the reciprocal movement of the first electrode 10 in the movement mechanism 120, the first electrode 10 may be first moved to the front side relative to the second electrode 20, and may then be moved to the rear side, and may be moved reversely thereto.

Figure 6:
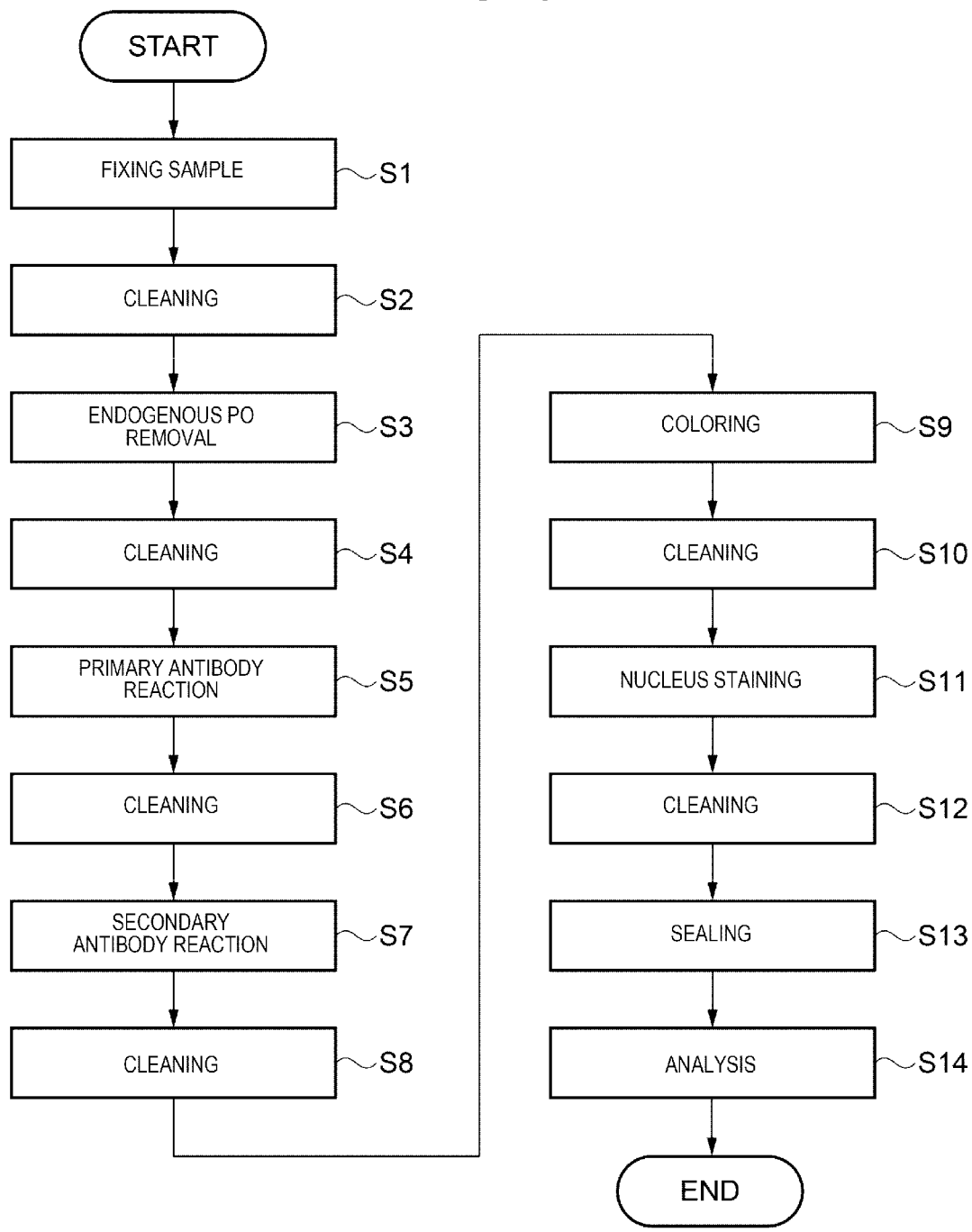
FIG. 6 is a flowchart illustrating an example of immunohistochemistry (IHC).

An effect of the electric field stirring method using the electric field stirring apparatus 100 of the present embodiment will now be described by exemplifying immunohistochemistry (IHC). FIG. 6 is a flowchart illustrating an example of the immunohistochemistry (IHC).

As illustrated in FIG. 6, an example of the IHC of the present embodiment includes a sample fixation process (step S1) of fixing the sliced tissue sample Ts to the workpiece W; a cleaning process (step S2) of cleaning the fixed tissue sample Ts; an endogenous peroxidase (PO) removal process (step S3) of removing an endogenous PO of the tissue sample Ts; a cleaning process (step S4) of cleaning the tissue sample Ts from which the endogenous PO is removed; a primary antibody reaction process (step S5); a cleaning process (step S6) of cleaning the tissue sample Ts having undergone the primary antibody reaction treatment; a secondary antibody reaction process (step S7); and a cleaning process (step S8) of cleaning the tissue sample Ts having undergone the secondary antibody reaction treatment. The example of the IHC also includes a coloring process (step S9) of coloring the cleaned tissue sample Ts; a cleaning process (step S10) of cleaning the colored tissue sample Ts; a nucleus staining process (step S11) of subjecting the cleaned tissue sample Ts to nucleus staining; a cleaning process (step S12) of cleaning the tissue sample Ts subjected to the nucleus staining; a sealing process (step S13) of enclosing the cleaned tissue sample Ts; and an analysis process (step S14) of checking the staining density of the enclosed tissue sample Ts.

In the sample fixation process of step S1, a frozen section obtained by slicing a pig liver block as the tissue sample Ts is disposed inside the water repellent ring 2 of the workpiece W, and then the workpiece W is immersed in acetone for two minutes. Consequently, the frozen section is stuck and fixed to the substrate 1 of the workpiece W. In other words, the workpiece W to which the tissue sample Ts is fixed is obtained. As the tissue sample Ts, a paraffin section obtained by slicing a pig liver block and embedding the sliced block in paraffin may be used. In this case, the tissue sample Ts is fixed to the substrate 1 through deparaffinization treatment. The flow proceeds to step S2.

In step S2, the fixed tissue sample Ts is cleaned by using a cleaning liquid. Specifically, the tissue sample Ts is cleaned by causing PBS-T to flow on the workpiece W for 30 seconds by using the PBS-T, that is, PBS containing nonionic surfactant Tween20 as a cleaning liquid. The flow proceeds to step S3.

In the endogenous PO removal process of step S3, for example, a hydrogen peroxide solution of 3% by volume as a reagent for removing endogenous PO is dropped into the water repellent ring 2 of the work W. An amount of the dropped hydrogen peroxide solution of 3% by volume depends on a size of the water repellent ring 2, and is, for example, 150 microliters (μL). After a predetermined amount of the hydrogen peroxide solution of 3% by volume is supplied to the workpiece W, the workpiece W is allowed to stand still there for one minute, and then endogenous PO is removed from the tissue sample Ts through blocking. The process proceeds to step S4.

In the cleaning process of step S4, in the same manner as in step S2, cleaning using PBS-T is performed. The flow proceeds to step S5.

In the primary antibody reaction process of step S5, 150 μL of Hep-par1, as a primary antibody reagent, binding to protein contained a liver cell is dropped into the water repellent ring 2 of the workpiece W, and thus a primary antibody reaction is performed. The flow proceeds to step S6.

In the cleaning process of step S6, in the same manner as in step S2, cleaning using PBS-T is performed. The flow proceeds to step S7.

In the secondary antibody reaction process of step S7, for example, 150 μL of EnVision+Dual Link (manufactured by Dako Corporation) that is a sensitizing reagent using dextran polymer and peroxidase as a secondary antibody reagent is dropped into the water repellent ring 2 of the workpiece W, and thus a secondary antibody reaction is performed. The flow proceeds to step S8.

In the cleaning process of step S8, in the same manner as in step S2, cleaning using PBS-T is performed. The flow proceeds to step S9.

In the coloring process of step S9, for example, 150 μL of 3,3'-Diaminobenzidine (DAB) as a reagent for causing color development is dropped into the water repellent ring 2 of the work W, and the workpiece W is allowed to stand still there for three minutes, and thus the tissue sample Ts and the reagent (DAB) are reacted with each other such that a color is developed. The flow proceeds to step S10.

In the cleaning process of step S10, distilled water as a cleaning liquid is caused to flow for two minutes, and thus the workpiece W is cleaned. The flow proceeds to step S11.

In the nucleus staining process of step S11, as a reagent for nuclear staining (counter staining), for example, 150 μL of hematoxylin is dropped into the water repellent ring 2 of the work W, the workpiece W is allowed to stand still there for one minute, and thus the tissue sample Ts is reacted with the reagent (hematoxylin) such that nucleus staining (counter staining) is performed. The flow proceeds to step S12.

In the cleaning process of step S12, in the same manner as in step S10, the workpiece W is cleaned by using distilled water. The flow proceeds to step S13.

In the sealing process of step S13, in order to prevent the cleaned tissue sample Ts from being dried, a water-insoluble sealing agent is dropped into the water repellent ring 2 of the workpiece W such that sealing treatment of covering the tissue sample Ts with cover glass is performed. The flow proceeds to step S14.

In the analysis process of step S14, the tissue sample Ts subjected to the sealing treatment is imaged by using an image analysis apparatus having an imaging unit, and staining density is checked through image analysis. The tissue sample Ts with a positive finding and the tissue sample Ts with a negative finding are prepared, staining densities thereof are checked and compared with each other through image analysis, and thus pathological diagnosis is performed.

Comparison Example 1

In IHC of Comparison Example 1, in the primary antibody reaction process of step S5 and the secondary antibody reaction process of step S7, an electric field was generated between the first electrode 10 and the flat second electrode 20 (here, hereinafter, referred to as a second electrode 20R) with no groove 20b, and a primary antibody reagent and a secondary antibody reagent were subjected to electric field stirring. In the electric field stirring, the inter-electrode distance d between the first electrode 10 and the second electrode 20R was 4.1 mm, and the electric field was generated by applying an electric signal of which a voltage changes between 0 V to 4 kV in a cycle of 5 Hz to the second electrode 20R with a potential of the first electrode 10 as 0 V. A time period of the electric field stirring in Comparison Example 1 is five minutes. During the electric field stirring, the first electrode 10 and the second electrode 20R are kept disposed to face each other.

Comparison Example 2

In IHC of Comparison Example 2, in the same manner as in Comparison Example 1, in the primary antibody reaction process of step S5 and the secondary antibody reaction process of step S7, an electric field was generated between the first electrode 10 and the second electrode 20 provided with the groove 20b, and a primary antibody reagent and a secondary antibody reagent were subjected to electric field stirring. Conditions for the electric field stirring are the same as in Comparison Example 1, that is, the inter-electrode distance d between the first electrode 10 and the second electrode 20 was 4.1 mm, and the electric field was generated by applying an electric signal of which a voltage changes between 0 V to 4 kV in a cycle of 5 Hz to the second electrode 20 with a potential of the first electrode 10 as 0 V. A time period of the electric field stirring in Comparison Example 2 is also five minutes. During the electric field stirring, the first electrode 10 and the second electrode 20 are kept disposed to face each other at the origin.

Example 1

In IHC of Example 1, in the same manner as in Comparison Example 1, in the primary antibody reaction process of step S5 and the secondary antibody reaction process of step S7, an electric field was generated between the first electrode 10 and the second electrode 20 with the groove 20b, and a primary antibody reagent and a secondary antibody reagent were subjected to electric field stirring. As conditions for the electric field stirring, the inter-electrode distance d between the first electrode 10 and the second electrode 20 was 4.1 mm, and the electric field was generated by applying an electric signal of which a voltage changes between 0 V to 4 kV in a cycle of 5 Hz to the second electrode 20 with a potential of the first electrode 10 as 0 V. During the electric field stirring, the first electrode 10 was reciprocally moved relative to the origin in the front-rear direction (Y direction) by the movement mechanism 120 in a state in which the first electrode 10 and the second electrode 20 are disposed to face each other. Specifically, the first electrode 10 was reciprocally moved to a position where the outer edge 2ed of the predetermined region 2e in which the reagent was disposed on the workpiece W was deviated relative to the origin, in the front-rear direction (Y direction). A movement speed in reciprocal movement in this case is 1.0 mm/second (sec). Time of the electric field stirring is five minutes in the same manner as in Comparison Example 1 or Comparison Example 2.

Figure 7:
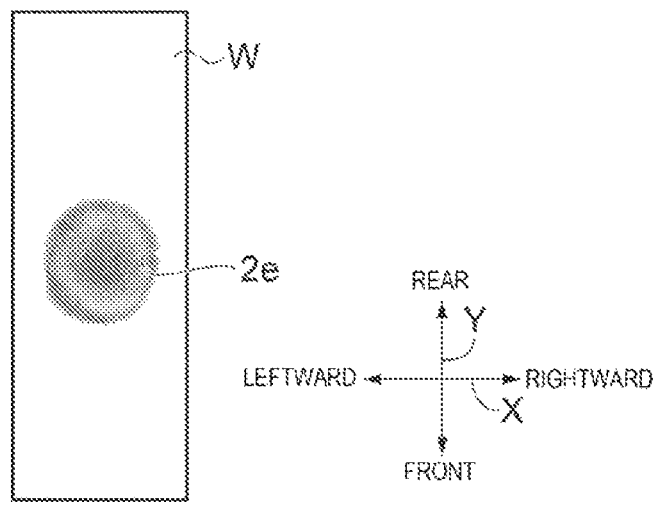
FIG. 7 is a diagram illustrating a coloring state due to the IHC in Comparison Example 1.
Figure 8:
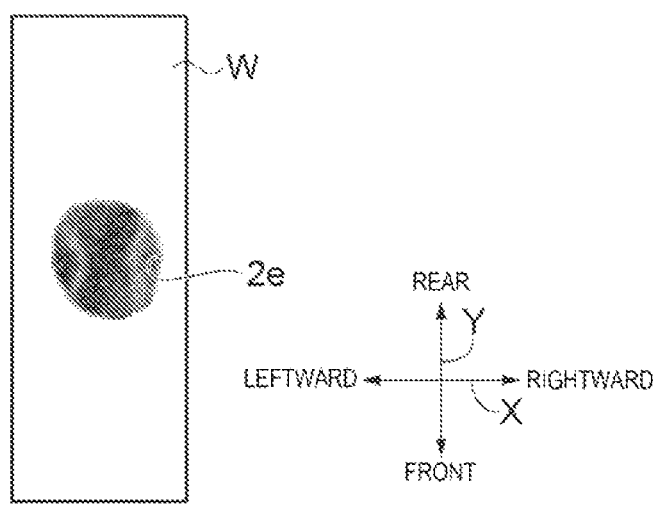
FIG. 8 is a diagram illustrating a coloring state due to the IHC in Comparison Example 2.
Figure 9:
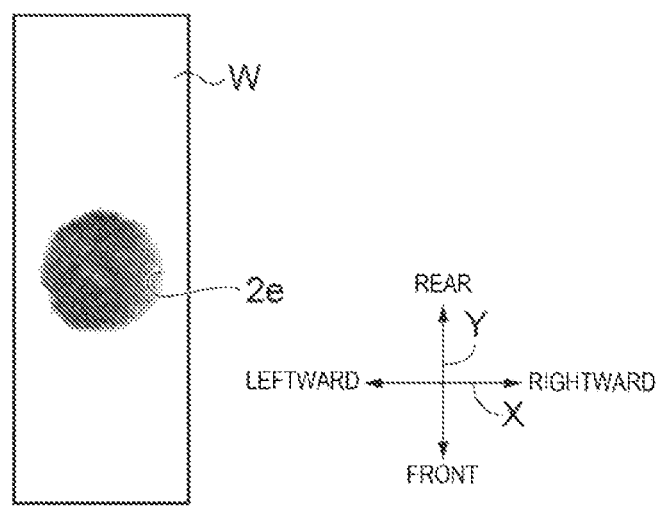
FIG. 9 is a diagram illustrating a coloring state due to the IHC in Example 1.

FIG. 7 is a diagram illustrating a coloring state due to the IHC in Comparison Example 1; FIG. 8 is a diagram illustrating a coloring state due to the IHC in Comparison Example 2; and FIG. 9 is a diagram illustrating a coloring state due to the IHC in Example 1. FIGS. 7 to 9 are diagrams illustrating black-and-white images obtained through image processing of color images obtained by imaging coloring states. As illustrated in FIG. 7, in the coloring state due to the IHC of Comparison Example 1, the color is developed over the predetermined region 2e in which the reagent is disposed, but ring-shaped coloring unevenness is checked in which the developed color is slightly thinner in a portion along the outer edge of the predetermined region 2e than in other portions.

As illustrated in FIG. 8, in the coloring state due to the IHC of Comparison Example 2, the color is developed thicker than in the coloring state in Comparison Example 1 illustrated in FIG. 7, but coloring unevenness is checked in which the developed color is slightly thinner in the predetermined region 2e in which the reagent is disposed than in other portions. The coloring unevenness is similar to stitches of a baseball in a plan view. Thus, the coloring unevenness appears symmetrically in the leftward-rightward direction (X direction) in which the groove 20b of the second electrode 20 is formed with respect to a central axis along the front-rear direction (Y direction) of the predetermined region 2e.

As illustrated in FIG. 9, the coloring state due to the IHC of Example 1 is in the same level as that of the coloring state of Comparison Example 2 illustrated in FIG. 8, and coloring unevenness such as stitches of a baseball in Comparison Example 2 is not checked. In other words, in the IHC of Example 1 to which the electric field stirring method of the present embodiment is applied, an antigen-antibody reaction efficiently progresses due to the electric field stirring, and thus a clearer coloring state is obtained than in Comparison Example 1. In Example 1, uniform electric field stirring is realized, and coloring unevenness as in Example 2 is improved. A movement speed when the first electrode 10 is reciprocally moved in the front-rear direction (Y direction) during the electric field stirring is set by taking into consideration physical properties such as an amount, viscosity, and surface tension of the droplet S formed in the water repellent ring 2.

According to the electric field stirring apparatus 100 of the first embodiment and the electric field stirring method using the electric field stirring apparatus 100, when the first electrode 10 and the second electrode 20 are disposed to face each other, a first portion in which a distance from the first electrode 10 is the predetermined inter-electrode distance d and a second portion longer than the first portion are generated in the portion of the groove 20b formed along the leftward-rightward direction (X direction) as a first direction in the second electrode 20. Therefore, when an electric field is generated between the first electrode 10 and the second electrode 20, an intensity of an electric field generated in the second portion is lower than an intensity of an electric field generated in the first portion. When a liquid is stirred under a situation of the electric field intensities, vibration of the liquid due to the electric field is increased more than in a case where the liquid is stirred at a constant electric field intensity. When the first electrode 10 is reciprocally moved in the front-rear direction (Y direction) as a second direction intersecting the leftward-rightward direction (X direction) by the movement mechanism 120 in a state in which the first electrode 10 and the second electrode 20 face each other, a position of the node when a liquid is vibrated due to an electric field swings in the front-rear direction (Y direction). Since weaker stirring occurs in a node portion in vibration of a liquid than in other portions, a position of the node in vibration is caused to swing in the front-rear direction (Y direction), and thus the liquid can be uniformly stirred compared with a case where a position of the node in vibration of the liquid is constant. In other words, it is possible to provide the electric field stirring apparatus 100 and the electric field stirring method capable of suppressing coloring unevenness caused by a reaction by uniformly stirring a reagent as a liquid and reacting the reagent with the tissue sample Ts.

In the first embodiment, the first electrode 10 is reciprocally moved relative to the origin in the front-rear direction (Y direction) during electric field stirring, but is not limited thereto, and the same effect can be achieved even through the second electrode 20 is reciprocally moved in the front-rear direction (Y direction) relative to the first electrode 10 on which the workpiece W is mounted. Both of the first electrode 10 and the second electrode 20 may be moved. In other words, at least one of the first electrode 10 and the second electrode 20 disposed to face each other may be reciprocally moved relative to the other electrode.

The electric field stirring method may be applied not only to the primary antibody reaction process or the secondary antibody reaction process but also to the coloring process or the cleaning process.

Second Embodiment

Pathological Sample Manufacturing Apparatus

Figure 10:
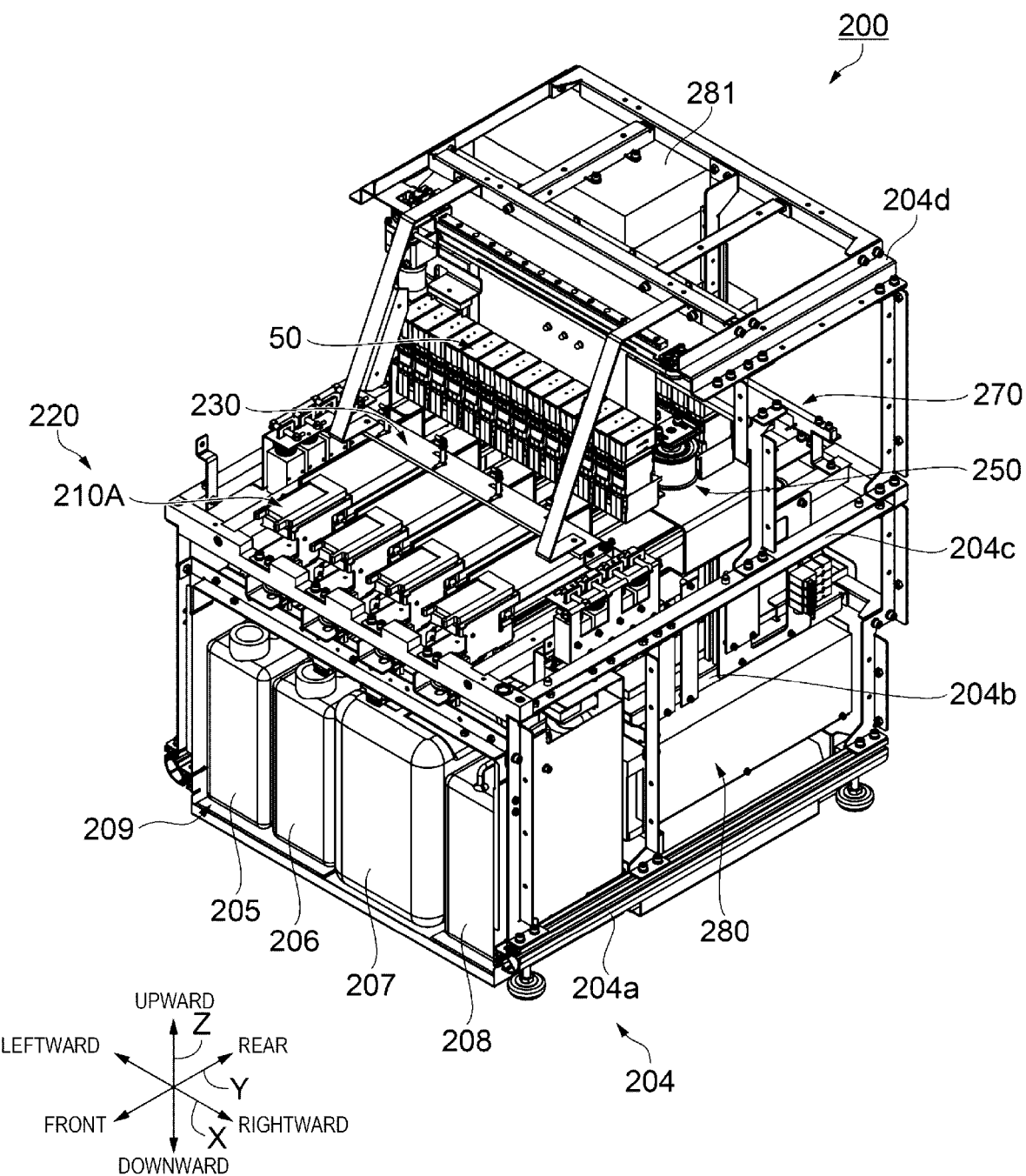
FIG. 10 is a schematic perspective view illustrating a configuration of a pathological sample manufacturing apparatus according to a second embodiment.

Next, with reference to FIG. 10, a description will be made of a principal configuration of a pathological sample manufacturing apparatus to which the electric field stirring apparatus of the present embodiment is applied. FIG. 10 is a schematic perspective view illustrating a configuration of a pathological sample manufacturing apparatus of a second embodiment. The pathological sample manufacturing apparatus of the present embodiment is an apparatus manufacturing a pathological sample required for pathological diagnosis based on a pathological sample manufacturing protocol such as immunohistochemistry (IHC) or In Situ Hybridization (ISH).

As illustrated in FIG. 10, a pathological sample manufacturing apparatus 200 of the present embodiment includes four tanks 205 to 208, a stage section 220, a cleaning section 230, a reagent supply section 250, an electric field stirring section 270, a circuit section 280, an electric field generation section 281, and a frame 204 as a structural body in which the respective sections are disposed. The frame 204 has a first frame 204a, a second frame 204b, a third frame 204c, and a fourth frame 204d that are frameworks forming stage parts for disposing the above-described sections in order from the bottom in the Z direction. The frame 204 is made of aluminum.

Hereinafter, a leftward-rightward direction of the pathological sample manufacturing apparatus 200 disposed on a workbench is set to an X direction, a front-rear direction orthogonal to the X direction is set to a Y direction, and an upward-downward direction orthogonal to the X direction and the Y direction is set to a Z direction.

The four tanks 205, 206, 207, and 208 are disposed to be arranged in this order in the X direction on the front side in the Y direction in the first frame 204a corresponding to the lowermost stage of the frame 204. In other words, a tank storage section 209 in which the four tanks 205 to 208 are allowed to be disposed side by side is attached to the first frame 204a.

Water ($H_2O$) as a cleaning liquid is stored in the tank 205. As the water, distilled water or pure water subjected to ion exchange treatment may be used. In the present embodiment, distilled water is stored in the tank 205. The tank 206 stores a buffer solution that is used to prevent the tissue sample Ts from being dried and is a cleaning liquid such as phosphate-buffered-saline (PBS), tris-buffered-saline (TBS), or standard-saline-citrate (SSC).

The tank 207 and the tank 208 are prepared to store a waste liquid of a cleaning liquid or a waste liquid of a reagent. A capacity of each of the tanks 205, 206, and 208 is, for example, 3 litters (L), and a capacity of the tank 207 is 5 L larger than the capacities of the other tanks. The tanks 205 to 208 employ resin containers such as polyethylene or polypropylene by taking into consideration chemical resistance or weight.

In immunohistochemistry (IHC), a coloring reagent may contain a carcinogen such as a coloring agent, and, when the coloring reagent is mixed with another liquid, an amount of a waste liquid that needs to be subjected to predetermined waste liquid treatment is increased. Therefore, there is a configuration in which the tank 207 in which a waste liquid of a cleaning liquid and a waste liquid of a reagent may be mixed and stored and the tank 208 in which a waste liquid containing a coloring reagent is stored are separately provided. In the present embodiment, the capacity of the tank 207 is larger than the capacities of the other tanks 205, 206, and 208. Therefore, it is possible to cope with an increase of an amount of a mainly used cleaning liquid, that is, an amount of a waste liquid depending on the type of pathological sample manufacturing protocol. The capacities of the tanks 205 to 208 may be the same as each other, and may be different from each other as necessary. The number of tanks storing a cleaning liquid or a waste liquid is not limited to four.

Figure 11:
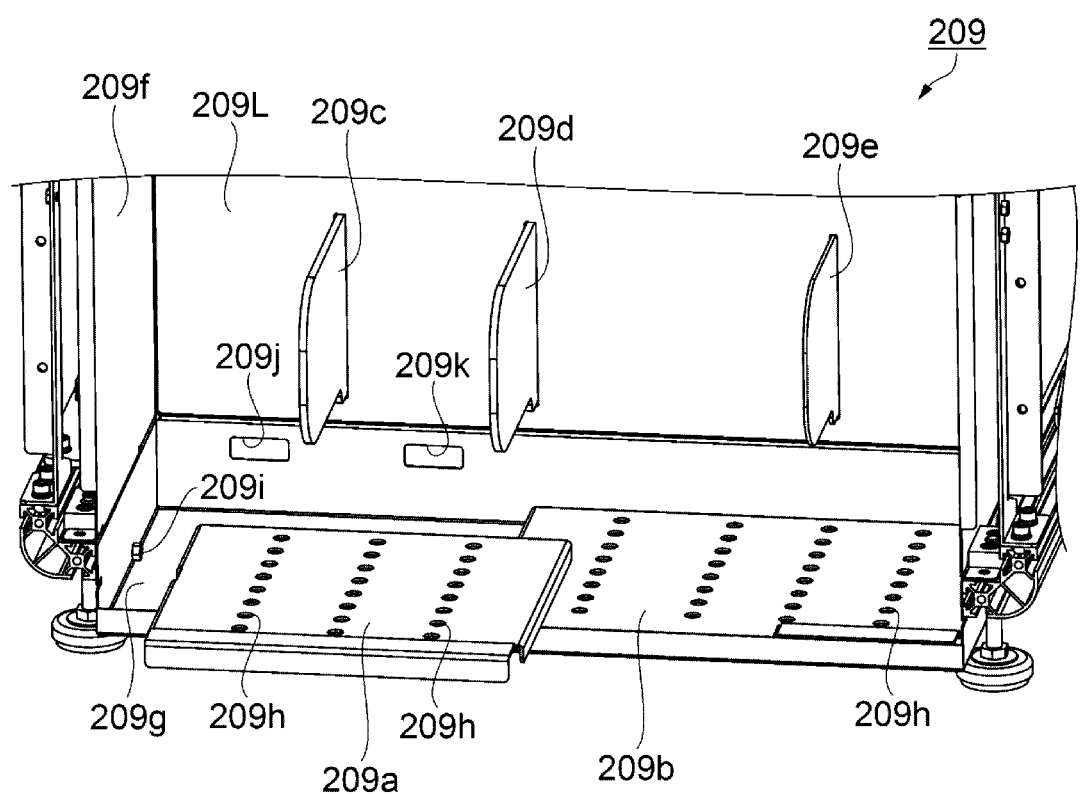
FIG. 11 is a schematic perspective view illustrating a configuration of a tank storage section.

FIG. 11 is a schematic diagram illustrating a configuration of the tank storage section. As illustrated in FIG. 11, two tank receiving portions 209a and 209b are provided on a bottom surface 209g of the tank storage section 209. FIG. 11 illustrates a state in which the tank receiving portion 209a located on the left in the X direction is raised, and a part of the tank receiving portion 209a is intentionally deviated to overlap the tank receiving portion 209b located on the right such that a structure of the tank storage section 209 can be understood.

Each of the tank receiving portions 209a and 209b is provided with a plurality of holes 209h that form a column with gaps in the Y direction. A plurality of columns of the holes 209h are provided to respectively correspond to the four tanks 205, 206, 207, and 208.

A drain hole 209i is provided at a boundary with the bottom surface 209g on a left sidewall 209f of the tank storage section 209 in the X direction. In other words, even though a liquid leaks when a cleaning liquid, a reagent, and waste liquids thereof are stored in the tanks 205, 206, 207, and 208 mounted on the tank receiving portions 209a and 209b, the leaked liquid is received at the bottom surface 209g through the plurality of holes 209h formed in the tank receiving portions 209a and 209b, and is discharged to the outside of the apparatus via the drain hole 209i.

Three partitions 209c, 209d, and 209e for mounting the four tanks 205, 206, 207, and 208 at predetermined positions are provided on a sidewall 209L on the rear side of the tank storage section 209 in the Y direction.

Two rectangular holes 209j and 209k are formed on a lower side of the rear sidewall 209L. When the two tanks 205 and 206 are mounted on the tank receiving portion 209a, the two holes 209j and 209k are formed at positions that are open toward bottoms of the two tanks 205 and 206. The tanks 205 and 206 are formed by using transparent or translucent resin containers. A residual quantity detection sensor 265 (not illustrated in FIG. 11) that detects residual quantities of various solutions stored in the tanks 205 and 206 is provided inside the two holes 209j and 209k formed in the sidewall 209L. A noncontact optical sensor may be used as the residual quantity detection sensor 265. An application of the residual quantity detection sensor 265 will be described later.

Each section configuring the tank storage section 209 is formed by using a steel material having water resistance, such as stainless steel (SUS).

As illustrated in FIG. 10, the circuit section 280 is disposed on the rear side of the first frame 204a in the Y direction. The circuit section 280 includes a power source unit supplying power to electrical drive systems included in the stage section 220, the cleaning section 230, and the reagent supply section 250, a control unit related to control of each section, and the like. An electrical configuration of the circuit section 280 will be described in a pathological sample manufacturing system which will be described later. The electric field generation section 281 supplying a high voltage to the electric field stirring section 270 is attached to the fourth frame 204d over the electric field stirring section 270. As mentioned above, the electric field generation section 281 is disposed around the electric field stirring section 270, and thus a wiring via which a high voltage is applied can be further shortened.

In the Z direction, a cleaning liquid supply mechanism (not illustrated) feeding and supplying a cleaning liquid from the tank 205 or the tank 206, and a channel switching mechanism 240 (refer to FIG. 18) switching discharge channels for separately discharging a waste liquid of a cleaning liquid or a waste liquid of a reagent to the tank 207 and the tank 208 are disposed in the second frame 204b located on the first frame 204a. The cleaning liquid supply mechanism may include, for example, a mechanism that pumps and supplies a cleaning liquid stored in each of the tank 205 and the tank 206 by using a pump, or a mechanism that sends a gas to the tank 205 and the tank 206 so as to press the cleaning liquid stored therein such that the cleaning liquid is fed to the outside from each of the tank 205 and the tank 206. The channel switching mechanism 240 will be described later.

The stage section 220 includes a stage 210A on which the workpiece W is mounted, a stage transport mechanism that moves the stage 210A in the Y direction, and a stage inclination mechanism that inclines the stage 210A in the X direction. The stage section 220 extending in the Y direction is disposed in a plurality (four, in the present embodiment) in parallel in the X direction in the third frame 204c. Details of the stage transport mechanism and the stage inclination mechanism will be described later. The number of stage sections 220 is not limited to four. Each stage section 220 is individually disposed in the third frame 204c, and can thus be subjected to individual maintenance.

The cleaning section 230, the reagent supply section 250, and the electric field stirring section 270 are disposed in this order from the front side in the Y direction in the third frame 204c. The cleaning section 230 has a plurality of (four) nozzles corresponding to the number of stages 210A, and is configured to supply a cleaning liquid required for cleaning of two types of cleaning liquids to each of the plurality of stages 210A. The cleaning section 230 is coupled to a gas supply section, has a plurality of (four) nozzles corresponding to the number of stages 210A, and is configured to blow a gas from each nozzle to each of the plurality of stages 210A. In other words, the cleaning section 230 has two types of nozzles, that is, a total of eight nozzles for a single stage 210A.

The reagent supply section 250 is configured to supply a reagent required for a reaction among a plurality of types of reagents to each of the plurality of (four) stages 210A. Details of the reagent supply section 250 will be described later.

The electric field stirring section 270 has an upper electrode 272 (refer to FIG. 24) corresponding to the second electrode 20 of the electric field stirring apparatus 100 of the first embodiment. The upper electrode 272 is provided electrically separately in correspondence with each of the plurality of (four) stage sections 220. Details of the upper electrode 272 will be described later.

In each stage section 220, the stage 210A is moved in the Y direction by the stage transport mechanism, and is disposed to correspond to each of the cleaning section 230, the reagent supply section 250, and the electric field stirring section 270.

According to the pathological sample manufacturing apparatus 200, a maximum of four workpieces W can be disposed on the respective stages 210A, and pathological samples can be manufactured. Since the four tanks 205 to 208 and the circuit section 280, the stage sections 220, the cleaning section 230 and the reagent supply section 250 and the electric field stirring section 270, and the electric field generation section 281 are disposed to overlap each other in the frame 204, the small-sized pathological sample manufacturing apparatus 200 having a small footprint (installation area) is realized. Hereinafter, a configuration or a structure of each section of the pathological sample manufacturing apparatus 200 will be described in detail. The frame 204 in which the respective sections can be disposed to overlap each other is not limited to a four-stage configuration having the first frame 204a, the second frame 204b, the third frame 204c, and the fourth frame 204d, and may have a four or more-stage configuration, for example, a five-stage configuration.

Stage Section

Figure 12:
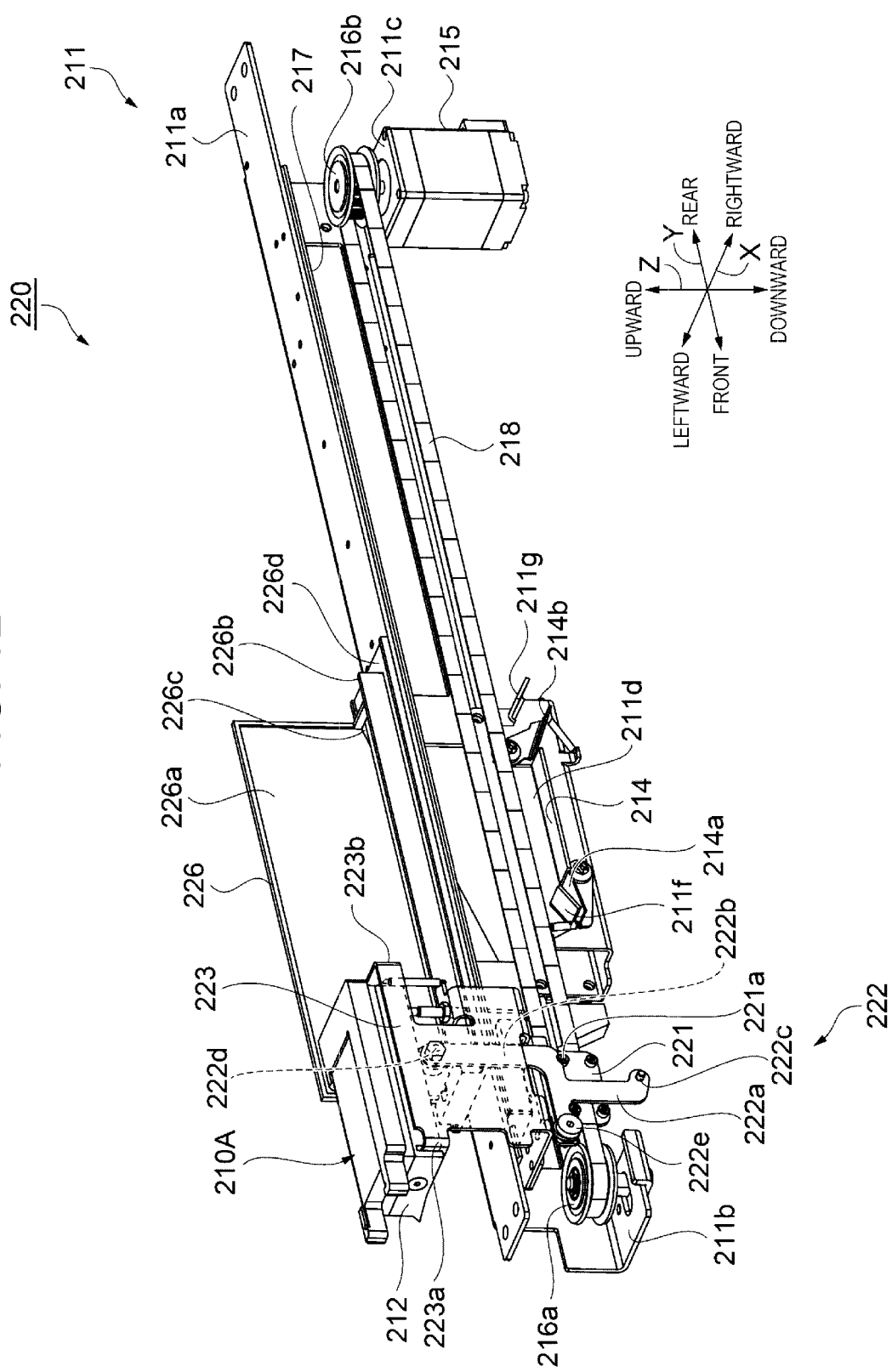
FIG. 12 is a schematic perspective view illustrating a configuration of a stage section of the pathological sample manufacturing apparatus.
Figure 13:
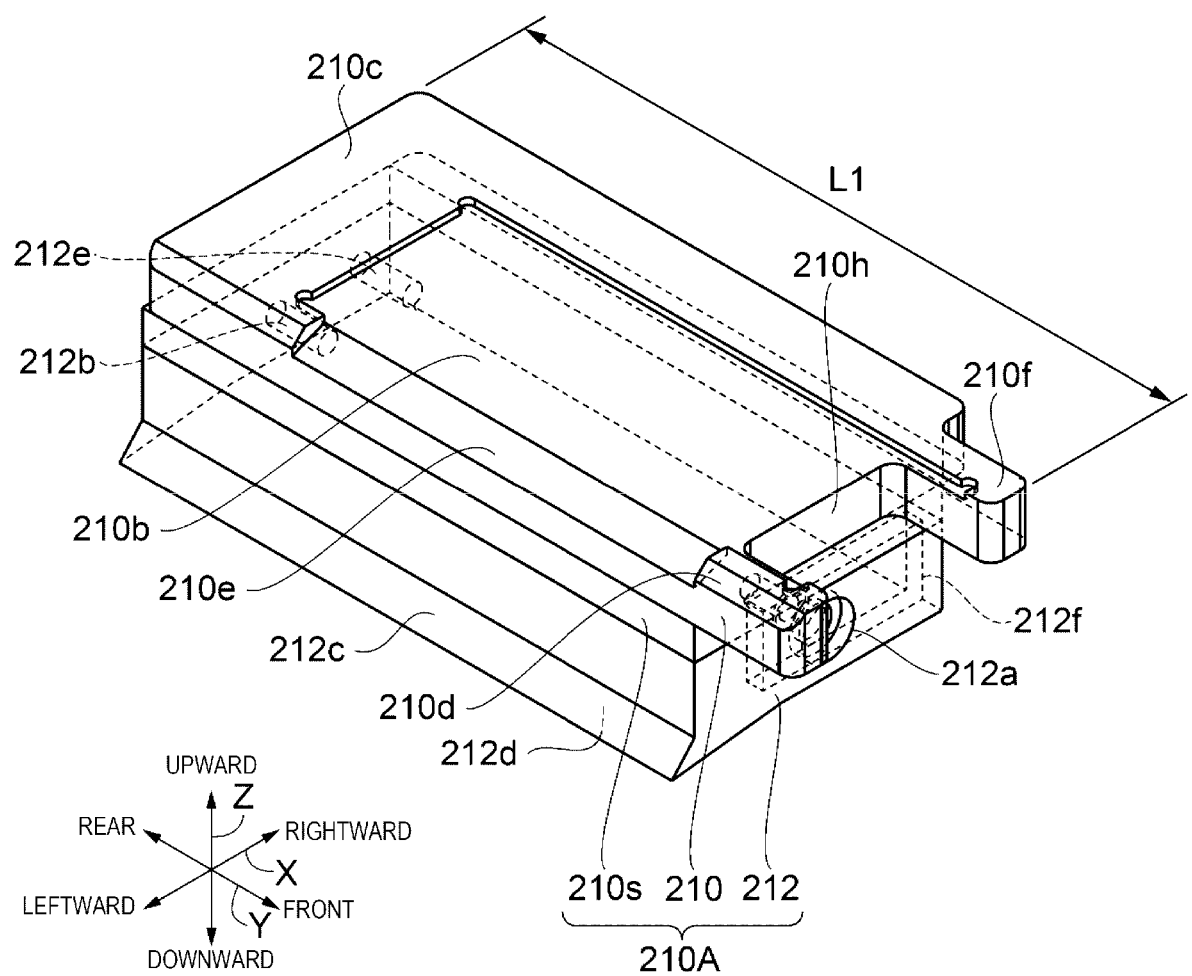
FIG. 13 is a schematic perspective view illustrating a configuration of a stage of the stage section.
Figure 14:
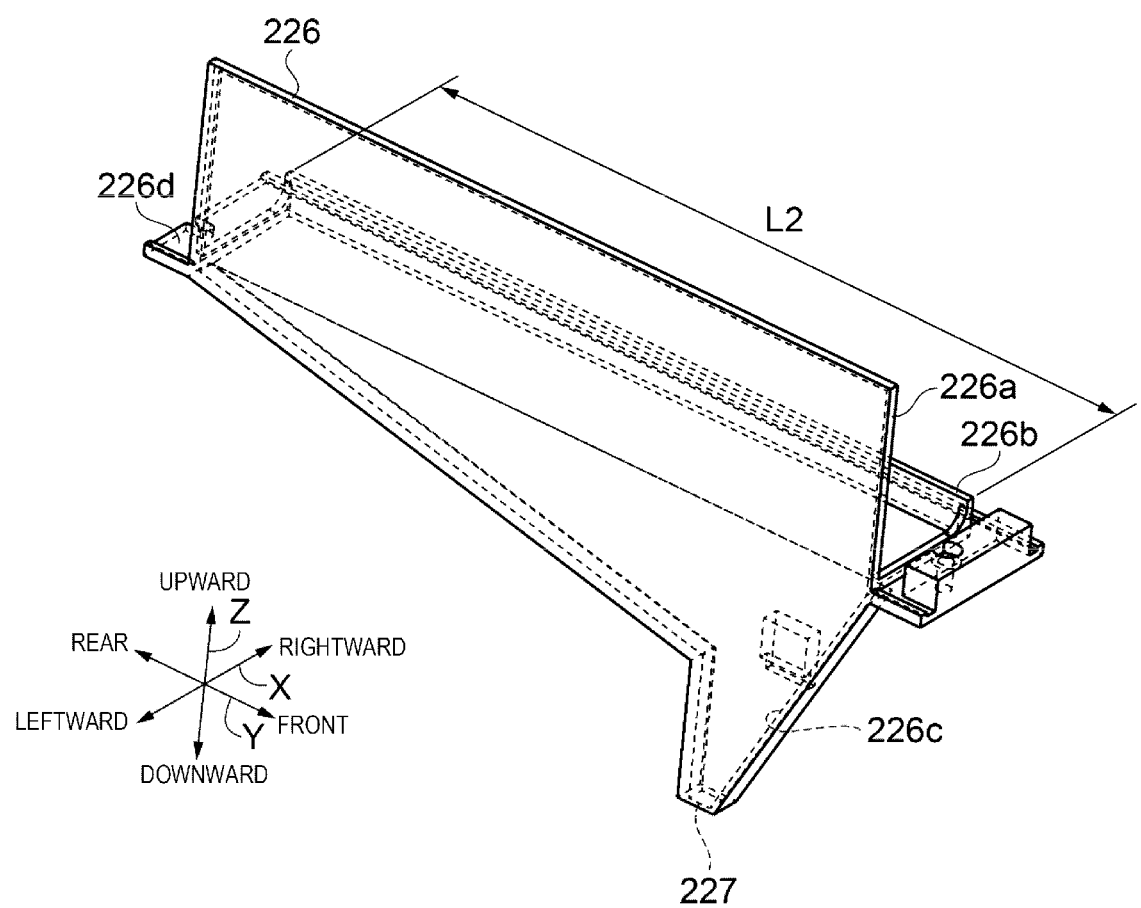
FIG. 14 is a schematic perspective view illustrating a liquid discharge guide portion of the stage section.

Next, the stage section 220 will be described with reference to FIGS. 12 to 14. FIG. 12 is a schematic perspective view illustrating a configuration of the stage section in the pathological sample manufacturing apparatus; FIG. 13 is a schematic perspective view illustrating a configuration of the stage of the stage section; and FIG. 14 is a schematic perspective view illustrating a liquid discharge guide portion of the stage section.

As illustrated in FIG. 12, the stage section 220 includes the stage 210A, a support frame 211, a motor 215, a linear guide 217, a first stage support portion 221, a second stage support portion 223, and a liquid discharge guide portion 226.

The support frame 211 has an upper surface part 211a extending in the Y direction, a pair of leg parts 211b and 211c supporting both ends of the surface part 211a in the Y direction, and a side part 211d supporting the surface part 211a at an intermediate position in the Y direction. The support frame 211 is a frame in which the upper surface part 211a, the pair of leg parts 211b and 211c, and the side part 211d are integrally formed, for example, by bending a SUS plate subjected to outer shape machining. The linear guide 217 is provided to extend in the Y direction on a lower surface of the upper surface part 211a in the Z direction.

The motor 215 is, for example, a stepping motor, and is attached to one leg part 211c located on the rear side of the pair of leg parts 211b and 211c in the Y direction such that a rotation shaft thereof is directed upward in the Z direction. The rotation shaft is provided with a timing pulley 216b. Another timing pulley 216a is pivotally supported by the other leg part 211b so as to be rotatable. A timing belt 218 is stretched between the two timing pulleys 216a and 216b. The first stage support portion 221 is fixed to a right portion of the stretched timing belt 218 in the X direction. When the motor 215 is driven, the timing belt 218 is rotated, and thus the first stage support portion 221 fixed to the timing belt 218 may be moved to the front side and the rear side in the Y direction.

The side part 211d supporting the upper surface part 211a of the support frame 211 at the intermediate position in the Y direction is provided at a position closer to one leg part 211b of the pair of leg parts 211b and 211c. The liquid discharge guide portion 226 is provided along the upper surface part 211a at the position where the side part 211d is provided.

As illustrated in FIG. 13, the stage 210A is substantially a rectangular parallelepiped, and a longitudinal direction thereof is disposed along the Y direction. The stage 210A has a lower electrode 210 corresponding to the first electrode 10 of the electric field stirring apparatus 100 of the first embodiment. The lower electrode 210 is disposed on a pedestal 212 with a tabular insulating portion 210s interposed. The lower electrode 210 is provided with a mounting portion 210b on which the workpiece W is mounted. A guide portion 210c and a guide portion 210d mounting the workpiece W on the mounting portion 210b at a predetermined position in the X direction and the Y direction are provided. The guide portion 210c is provided on a right lateral side in the X direction and a rear end side in the Y direction of the mounting portion 210b. The guide portion 210d is provided at a left corner on the front side of the mounting portion 210b. An oblique portion 210e is provided on a left lateral side of the mounting portion 210b in the X direction. The mounting portion 210b has a notch part 210h of which a front side is notched. The notch part 210h is notched such that, when the end of the workpiece W is held by, for example, tweezers, and is set or reset onto the mounting portion 210b, the tweezers are not brought into contact with the lower electrode 210. In other words, there is a configuration in which setting or resetting of the workpiece W for the stage 210A is easily performed. The stage 210A is transported to a position facing the upper electrode 272 of the electric field stirring section 270 which will be described later by a transport mechanism of the stage section 220. In the stage 210A, the lower electrode 210 and the pedestal 212 are formed by using, for example, aluminum. Although not illustrated in FIG. 13, a Peltier element 16 as a heating member heating the lower electrode 210, and a temperature sensor 17 (refer to FIG. 30) are incorporated into the tabular insulating portion 210s interposed between the lower electrode 210 and the pedestal 212.

The pedestal 212 has a groove portion 212f that is formed to be cut with a predetermined width in the X direction on the front side in the Y direction. A screw hole 212a is formed on a sidewall of the pedestal 212 on the front side in the Y direction, and two screw holes 212b and 212e are formed on a sidewall of the pedestal 212 on the rear side in the Y direction. The pedestal 212 has an oblique portion 212c that obliquely prolongs outward from the lower end on the left side in the X direction.

As illustrated in FIG. 12, the stage 210A is supported to be rotatable in a predetermined direction from a horizontal state by the second stage support portion 223. Specifically, one arm part 223a of a pair of arm parts 223a and 223b of the second stage support portion 223 is inserted into the groove portion 212f of the pedestal 212. Holes respectively corresponding to the screw holes 212a and 212b provided in the pedestal 212 are formed on front end sides of the pair of arm parts 223a and 223b. Shafts are inserted into the screw holes 212a and 212b, and the shafts penetrate through the holes formed in the pair of arm parts 223a and 223b, and thus the pedestal 212 is supported by the second stage support portion 223 in a state of being rotatable about the shafts.

The linear guide 217 is provided directly under the upper surface part 211a of the support frame 211. A slider 217a (refer to FIG. 15) is attached to the linear guide 217. The slider 217a is fixed to the second stage support portion 223. The second stage support portion 223 is fixed to the first stage support portion 221 attached to the timing belt 218. In other words, when the motor 215 is driven to move the timing belt 218, the stage 210A supported by the first stage support portion 221 and the second stage support portion 223 is movable in the Y direction along the linear guide 217. In other words, the stage transport mechanism in the present embodiment includes at least the motor 215 as a drive source, the timing pulleys 216a and 216b, the linear guide 217, the slider 217a, the timing belt 218, the first stage support portion 221, and the second stage support portion 223.

Although not illustrated in FIG. 12, a sensor is attached to the front side of the upper surface part 211a of the support frame 211 in the Y direction. The sensor has a function of detecting a position of the first stage support portion 221 that is fixed to the timing belt 218 and is moved in the Y direction, and stopping the motor 215. A position of the stage 210A when the sensor stops the motor 215 is the origin in the stage transport mechanism in the Y direction. When the stage 210A is located at the origin, the workpiece W is set or reset in the stage 210A.

As illustrated in FIG. 14, the liquid discharge guide portion 226 of the present embodiment has a polygonal gutter shape in terms of outer shape when viewed from the X direction, and a flexible tube is attached to a coupling portion 227 provided at a front end side of a channel 226c extending downward. The liquid discharge guide portion 226 has a protrusion 226d that protrudes in the X direction and can be screwed into the upper surface part 211a of the support frame 211. The protrusion 226d has a guide part 226b of which a shape including a side surface part 226a is an L shape when viewed from the Y direction. An edge of the guide part 226b extends upward in the Z direction from the protrusion 226d. A length L2 of the guide part 226b in the Y direction is larger than a length L1 (refer to FIG. 13) of the stage 210A in the Y direction. A position where the liquid discharge guide portion 226 is attached to the upper surface part 211a of the support frame 211 corresponds to a cleaning position in the Y direction. In other words, there is a configuration in which, even though the workpiece W mounted on the stage 210A is cleaned with a cleaning liquid by moving the stage 210A to the front side and the rear side in the Y direction, the cleaning liquid discharged from the upper part of the stage 210A can be received by the guide part 226b, so as to be guided to the coupling portion 227 from the channel 226c.

Stage Inclination Mechanism

Figure 15:
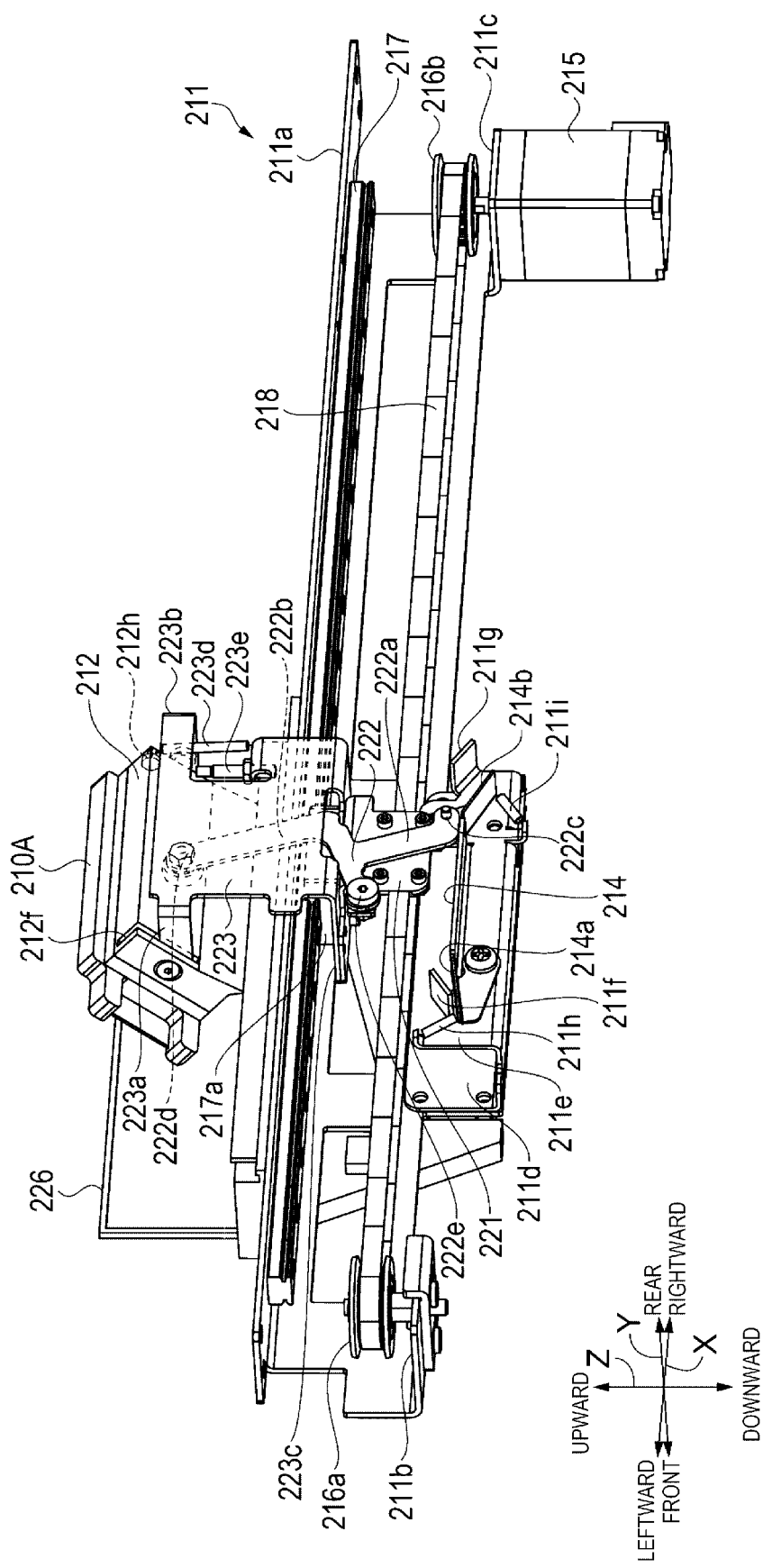
FIG. 15 is a schematic perspective view for describing a stage inclination mechanism of the pathological sample manufacturing apparatus.
Figure 16:
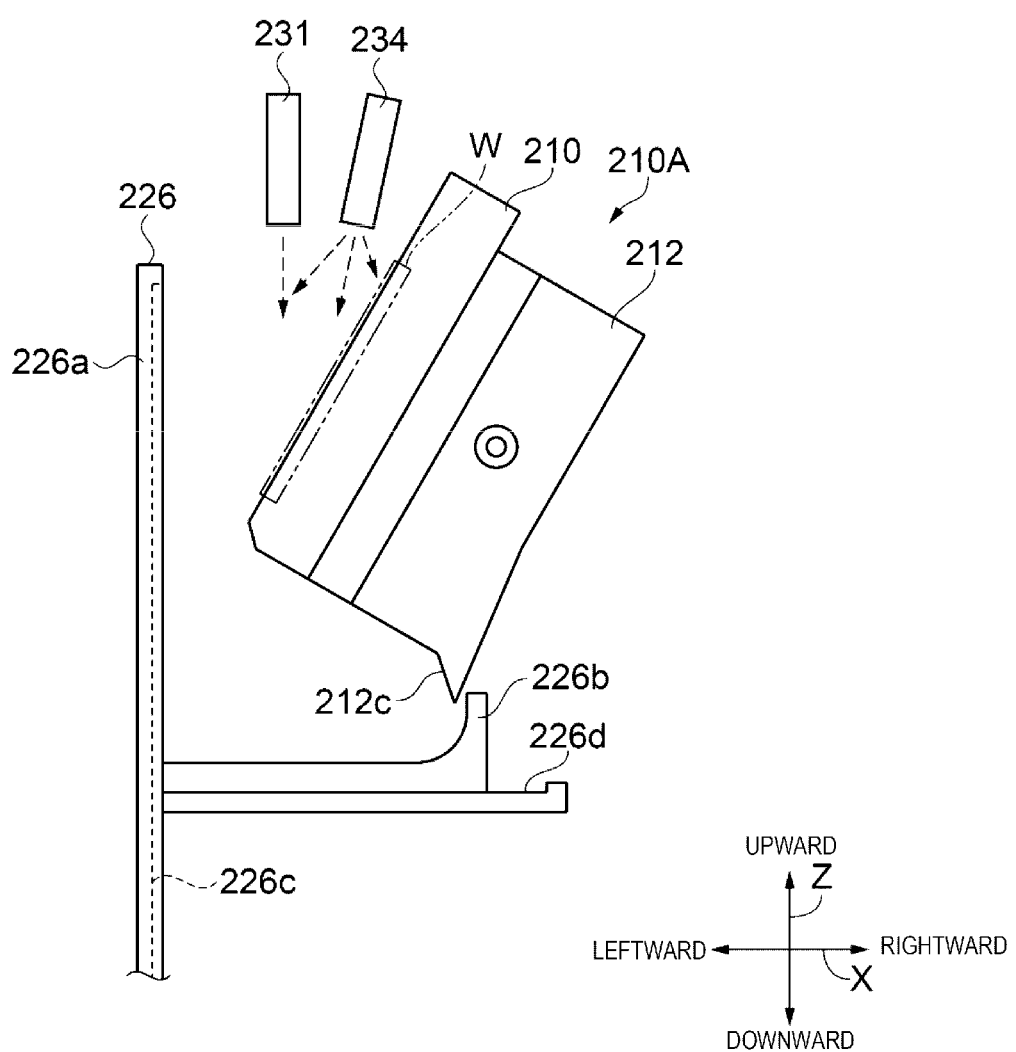
FIG. 16 is a diagram illustrating positional relationships among the stage inclined by the stage inclination mechanism and other constituent elements.

Next, with reference to FIGS. 15 and 16, the stage inclination mechanism of the present embodiment will be described. FIG. 15 is a schematic perspective view for describing the stage inclination mechanism of the pathological sample manufacturing apparatus, and FIG. 16 is a diagram illustrating positional relationships among the stage inclined by the stage inclination mechanism and other constituent elements. FIG. 16 is a view when the inclined stage 210A is viewed from the front side in the Y direction.

As illustrated in FIG. 15, the side part 211d of the support frame 211 is provided with a wall surface 211e standing downward of the timing belt 218, a plate 214 that is in contact with the wall surface 211e and extends in the Y direction, and a pair of oblique parts 211f and 211g that are obliquely provided in different directions on the front side and the rear side of the wall surface 211e in the Y direction. The wall surface 211e is provided with a pair of guide plates 214a and 214b respectively facing the pair of oblique parts 211f and 211g on the front side and the rear side of the plate 214 in the Y direction. Each of the pair of guide plates 214a and 214b is supported at the wall surface 211e in a rotationally movable state with the plate 214 side as a fulcrum.

Of the pair of guide plates 214a and 214b, one guide plate 214a on the front side in the Y direction has a front end on the front side biased upward in the Z direction by a spring 211h stretched to the wall surface 211e. The other guide plate 214b has a front end on the rear side biased downward in the Z direction by a spring 211i stretched to the wall surface 211e. Therefore, one guide plate 214a is inclined to be substantially horizontal and is continued to the plate 214 in a state of being biased by each of the springs 211h and 211i. The other guide plate 214b is continued to the plate 214 in a state of being inclined rearward in the Y direction.

A lever 222 is pivotally supported at the first stage support portion 221 attached to the timing belt 218 so as to be rotationally moved. The lever 222 has a first arm 222a extending downward in the Z direction, and a second arm 222b that is continued to the first arm 222a, extends in the Y direction, and then extends upward, and an outer shape thereof when viewed from the X direction is a substantially T shape. A rod is attached to a front end part 222c of the first arm 222a in a state of being rotatable via a miniature bearing. Similarly, a rod is attached to an upper front end part 222d of the second arm 222b in a state of being rotatable.

An end 222e of a portion of the second arm 222b of the lever 222 in the Y direction is pivotally supported at the first stage support portion 221. Therefore, as illustrated in FIG. 12, for example, when the stage 210A is located at the origin in the Y direction, the portion of the second arm 222b extending in the Y direction abuts on the screw 221a fixed to the first stage support portion 221, and thus rotation of the lever 222 about the end 222e is stopped. In this case, the upper front end part 222d of the second arm 222b of the lever 222 abuts on the bottom surface of the pedestal 212 of the stage 210A. When the motor 215 is driven in this state, and thus the stage 210A is moved from the origin rearward in the Y direction, the front end part 222c of the first arm 222a of the lever 222 passes the lower sides of the guide plate 214a and the plate 214, is raised over the rear guide plate 214b, and is then moved to the motor 215 side.

When rotational driving of the motor 215 is controlled, and thus the stage 210A moved rearward in the Y direction is moved frontward toward the origin again, the front end part 222c of the first arm 222a of the lever 222 is guided by the oblique part 211g so as to abut on the rear guide plate 214b, and thus rides on the plate 214. Consequently, the lever 222 rotationally moves counterclockwise about the end 222e, and thus the front end part 222d of the second arm 222b pushes up the bottom surface of the pedestal 212. The stage 210A having pushed up the bottom surface of the pedestal 212 is inclined toward the liquid discharge guide portion 226 in the X direction.

When the stage 210A is moved toward the origin, the front end part 222c of the first arm 222a of the lever 222 abuts on the front oblique part 211f from the plate 214, and thus pushes down the front guide plate 214a. Therefore, since the front end part 222c of the first arm 222a is deviated from the guide plate 214a and is thus moved frontward, the lever 222 is rotated clockwise about the end 222e and abuts on the screw 221a of the first stage support portion 221, so that rotation thereof is stopped. Consequently, the operation in which the upper front end part 222d of the second arm 222b of the lever 222 is pushing up the bottom surface of the pedestal 212 is canceled. A locking part 212h is screwed into the screw hole 212e (refer to FIG. 13) provided on the rear wall surface of the pedestal 212 in the Y direction. A spring 223d is stretched between the locking part 212h and the second stage support portion 223. The second stage support portion 223 has a contact 223e standing in the Z direction on the lower side of the pedestal 212. When the operation in which the upper front end part 222d of the second arm 222b of the lever 222 is pushing up the bottom surface of the pedestal 212 is canceled, the pedestal 212 is attracted by the stretched spring 223d, and thus the bottom surface 212d (refer to FIG. 13) of the pedestal 212 abuts on the contact 223e. Consequently, the rotational movement of the stage 210A supported by the second stage support portion 223 is stopped, and thus the mounting portion 210b of the stage 210A becomes horizontal.

In other words, the stage section 220 has the stage inclination mechanism including the pair of oblique parts 211f and 211g, the plate 214, the pair of guide plates 214a and 214b, the first stage support portion 221, and the lever 222, to incline the stage 210A toward the liquid discharge guide portion 226 in the X direction.

As illustrated in FIG. 16, the stage inclination mechanism of the stage section 220 inclines the stage 210A toward the liquid discharge guide portion 226. The stage 210A is inclined to be stopped in a state in which the oblique portion 212c of the pedestal 212 is brought into contact with the guide part 226b of the liquid discharge guide portion 226 or immediately before the oblique portion 212c is brought into contact with the guide part 226b. An inclined angle of the stage 210A in this case is an angle formed between the workpiece W mounted on the stage 210A and inclined and the horizontal plane, and is set in a range of 45 degrees to 60 degrees. Specifically, an inclined angle of the stage 210A may be adjusted by adjusting an attachment position of the plate 214 in the Z direction to the wall surface 211e of the side part 211d illustrated in FIG. 15, a length from the end 222e of the lever 222 to the front end part 222c of the first arm 222a, and a length from the end 222e of the lever 222 to the front end part 222d of the second arm 222b.

As described above, since the stage 210A is inclined, when a cleaning liquid is ejected toward the workpiece W from a nozzle 231 located over the stage 210A, the cleaning liquid runs on the surface of the workpiece W, and flows down into the guide part 226b of the liquid discharge guide portion 226. For example, even though the cleaning liquid goes around the lower electrode 210 so as to flow to the side surface of the pedestal 212, the cleaning liquid runs on the oblique portion 212c provided at the pedestal 212 so as to flow down into the guide part 226b. In the present embodiment, another nozzle 234 is disposed over the stage 210A. The nozzle 234 is disposed to be inclined in the Z direction, and air is blown toward the inclined workpiece W from the nozzle 234. Therefore, air is blown toward the surface of the inclined workpiece W from the nozzle 234, and thus the cleaning liquid ejected from the nozzle 231 can be discharged to the liquid discharge guide portion 226 without being left.

Cleaning Section

Figure 17:
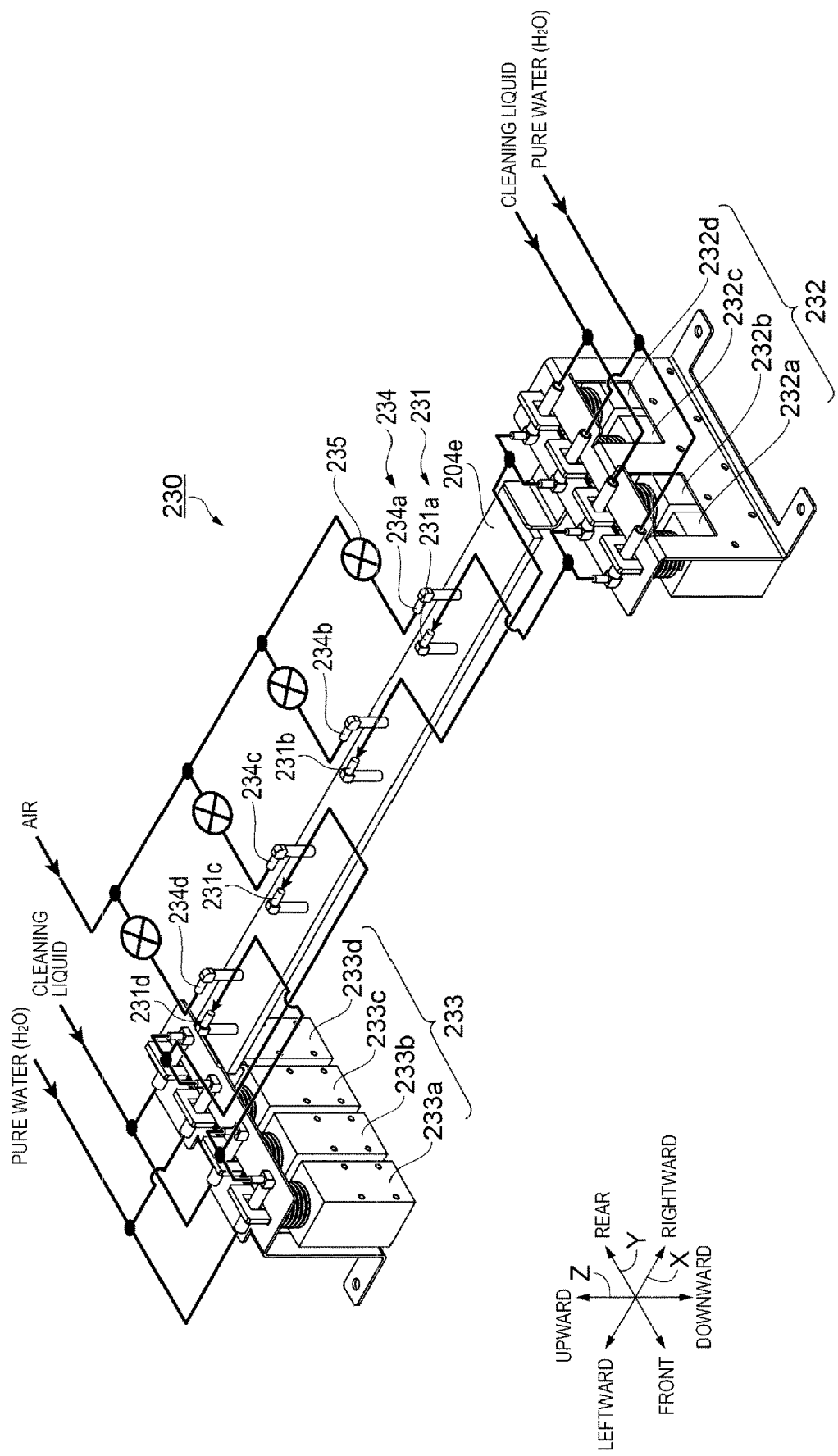
FIG. 17 is a schematic perspective view illustrating a configuration of a cleaning section of the pathological sample manufacturing apparatus.
Figure 18:
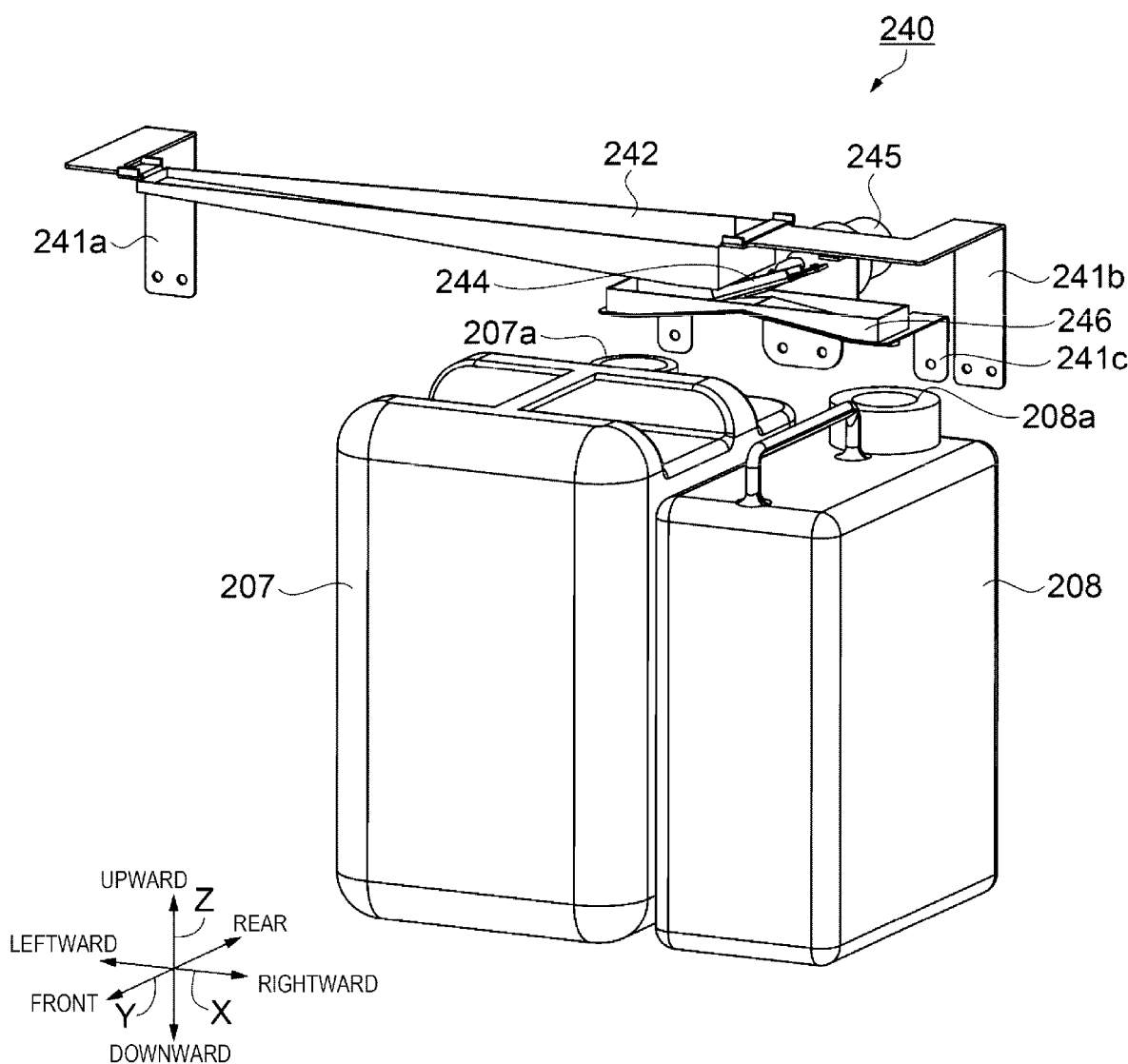
FIG. 18 is a schematic perspective view illustrating a configuration of a channel switching mechanism of the cleaning section.

A description will be made of the cleaning section 230 of the present embodiment with reference to FIGS. 17 and 18. FIG. 17 is a schematic perspective view illustrating a configuration of the cleaning section of the pathological sample manufacturing apparatus, and FIG. 18 is a schematic perspective view illustrating a configuration of a channel switching mechanism of the cleaning section.

As illustrated in FIG. 17, the cleaning section 230 has a plurality of (four) nozzles 231 ejecting a cleaning liquid, a plurality of (four) nozzles 234 blowing air, a valve group 232 and a valve group 233 having a plurality of valves, and a support plate 204e supporting the plurality of nozzles 231 and nozzles 234.

The support plate 204e has a rectangular shape, and is supported at the third frame 204c of the frame 204 of the pathological sample manufacturing apparatus 200 such that a longitudinal direction thereof is parallel to the X direction (refer to FIG. 10). The plurality of nozzles 231 and nozzles 234 are disposed at an equal interval in the X direction on the support plate 204e. The plurality of nozzles 231 are given reference signs in order from the right in the X direction, and will be referred to as a nozzle 231a, a nozzle 231b, a nozzle 231c, and a nozzle 231d. Similarly, the plurality of nozzles 234 are given reference signs in order from the right in the X direction, and will be referred to as a nozzle 234a, a nozzle 234b, a nozzle 234c, and a nozzle 234d. The nozzles 231 and 234 are provided to correspond to each stage 210A of the stage section 220. In the X direction, the nozzle 234 is disposed to be slightly deviated to the right relative to the nozzle 231.

Each of the valve group 232 and the valve group 233 includes a plurality of valves provided to correspond to the number of nozzles 231. The valve group 232 has a plurality of (four) valves 232a, 232b, 232c, and 232d arranged in the Y direction. The valve group 233 also has a plurality of (four) valves 233a, 233b, 233c, and 233d arranged in the Y direction. The valve group 232 and the valve group 233 are separately disposed in the third frame 204c of the pathological sample manufacturing apparatus 200 so as to face each other in the X direction with the support plate 204e interposed therebetween (refer to FIG. 10).

The valve group 232 and the valve group 233 are electromagnetic valves of which opening and closing can be electrically controlled, and are controlled to be opened and closed by a control unit included in the circuit section 280 which will be described later. Specifically, each of the electromagnetic valves has a gate type opening/closing portion, and a flexible tube inserted into the opening/closing portion is pressed and squeezed by moving the opening/closing portion down such that a liquid channel in the tube can be closed. When the opening/closing portion is moved up, and thus pressing of the tube is canceled, the liquid channel in the tube can be opened.

For example, as indicated by a solid line in FIG. 17, a flexible tube is coupled to the nozzle 231a via the valve 232a and the valve 232b. Similarly, a flexible tube is coupled to the nozzle 231b via the valve 232c and the valve 232d. Similarly, a flexible tube is coupled to the nozzle 231d via the valve 233a and the valve 233b. Similarly, a flexible tube is coupled to the nozzle 231c via the valve 233c and the valve 233d. Through the coupling, lengths of the flexible tubes from the valves to the nozzles 231 can be made substantially the same as each other for the respective nozzles 231. In other words, pressure losses when a cleaning liquid is supplied to the nozzles 231 can be uniformized for the respective nozzles 231, and thus a variation in an amount of the supplied cleaning liquid can be reduced.

Distilled water ($H_2O$) as a cleaning liquid is supplied to a piping system related to the valves 232a and 232c and the valves 233a and 233c, and another cleaning liquid is supplied to a piping system related to the valves 232b and 232d and the valves 233b and 233d. Opening and closing of each valve are controlled, and thus one of the two cleaning liquids can be selected and ejected from each of the plurality of nozzles 231a, 231b, 231c, and 231d.

Although not illustrated in FIG. 17, instead of separately providing supply paths for the cleaning liquid and the distilled water ($H_2O$) reaching the valve group 232 and the valve group 233, a part of a supply path for the distilled water ($H_2O$) is connected to a supply path for the cleaning liquid via the valve, and thus the distilled water ($H_2O$) can be supplied to the supply path for the cleaning liquid. Consequently, it is possible to perform maintenance of cleaning a path for the cleaning liquid reaching the nozzle 231 with the distilled water ($H_2O$). For example, even though the cleaning liquid remains in a path up to the nozzle 231 and is dried, and thus clogging occurs, the clogging can be removed by causing the distilled water ($H_2O$) to flow through the path.

Each of the plurality of nozzles 234a, 234b, 234c, and 234d supported by the support plate 204e is coupled to a gas supply portion via a valve 235. The gas supply portion in the present embodiment may include a small-sized pressing pump that compresses and delivers air. The valve 235 is also an electromagnetic valve, and is controlled to be opened and closed by the control unit of the circuit section 280.

Channel Switching Mechanism

The cleaning section 230 has the channel switching mechanism for discharging a cleaning liquid ejected from the nozzles 231 to the tank 207 or the tank 208 as a waste liquid. As illustrated in FIG. 18, the channel switching mechanism 240 of the cleaning section 230 is configured to include a pair of leg portions 241a and 241b, a waste liquid receiving portion 242, a motor 245, and a flow division passage 246.

The pair of leg portions 241a and 241b are attached to the third frame 204c of the frame 204 so as to face each other in the X direction. The waste liquid receiving portion 242, which has an elongated gutter shape, is supported at both end sides of an opening directed upward by the pair of leg portions 241a and 241b such that the opening is horizontal, and is disposed along the X direction.

Although not illustrated in FIG. 18, a front of a tube attached to the coupling portion 227 of the liquid discharge guide portion 226 provided in each of the plurality of stage sections 220 hangs down to the gutter-shaped waste liquid receiving portion 242.

The gutter-shaped waste liquid receiving portion 242 is formed such that the right side is deeper and wider than the left side in the X direction. A left end of the waste liquid receiving portion 242 in the X direction is closed, and a right end thereof is open.

The flow division passage 246 is disposed under the waste liquid receiving portion 242 in the Z direction. The flow division passage 246 also has a gutter shape, and has openings (not illustrated in FIG. 18) at both ends of a bottom in the X direction. The bottom of the flow division passage 246 is provided with oblique surfaces that are respectively oblique toward the two openings. The flow division passage 246 is supported from below by a side part 241c.

The side part 241c supporting the flow division passage 246 from below has a wall surface standing in the Z direction, and the motor 245 is attached to the wall surface such that a rotation shaft thereof is parallel to the Y direction. The motor 245 is, for example, a stepping motor, and a guide plate 244 is attached to the rotation shaft of the motor 245 inside the flow division passage 246. When the motor 245 is stopped, the guide plate 244 is inclined toward the left opening in the X direction of the two openings provided on the bottom of the flow division passage 246.

Of the two openings provided on the bottom of the flow division passage 246, one left opening in the X direction is located over an injection port 207a of the tank 207. Of the two openings, the other right opening in the X direction is located over an injection port 208a of the tank 208.

As described above, at the cleaning position, when the cleaning liquid is ejected to the workpiece W mounted on the stage 210A from the nozzle 231 in a state in which the stage 210A is inclined by the stage inclination mechanism, the cleaning liquid cleans the surface of the workpiece W and then flows into the liquid discharge guide portion 226. The cleaning liquid that has flowed into the liquid discharge guide portion 226 passes through the tube attached to the coupling portion 227 via the channel 226c, and then flows into the gutter-shaped waste liquid receiving portion 242. The cleaning liquid that has flowed into the waste liquid receiving portion 242 flows along the bottom rightward in the X direction. In this case, when the motor 245 is stopped, the cleaning liquid that has flowed into the waste liquid receiving portion 242 is guided to the left opening of the two openings along the guide plate 244, and is discharged to the tank 207 as a waste liquid.

In FIG. 18, when the motor 245 is driven such that the rotation shaft is rotated clockwise by a predetermined angle, the guide plate 244 attached to the shaft of the motor 245 is inclined rightward in the X direction, and thus the cleaning liquid that has flowed into the waste liquid receiving portion 242 is guided to the right opening in the X direction of the flow division passage 246 along the guide plate 244, and is discharged to the tank 208 as a waste liquid.

The channel switching mechanism 240 of the present embodiment includes at least the waste liquid receiving portion 242, the motor 245, the guide plate 244 attached to the rotation shaft of the motor 245, and the flow division passage 246. Consequently, for example, when a cleaning liquid flowing into the waste liquid receiving portion 242 does not contain a coloring reagent, the motor 245 stops driving, and thus the cleaning liquid treated as a waste liquid is discharged to the tank 207. For example, when a cleaning liquid flowing into the waste liquid receiving portion 242 contains a coloring reagent, the motor 245 is driven, and thus the cleaning liquid treated as another waste liquid is discharged to the tank 208.

Reagent Supply Section

Figure 19:
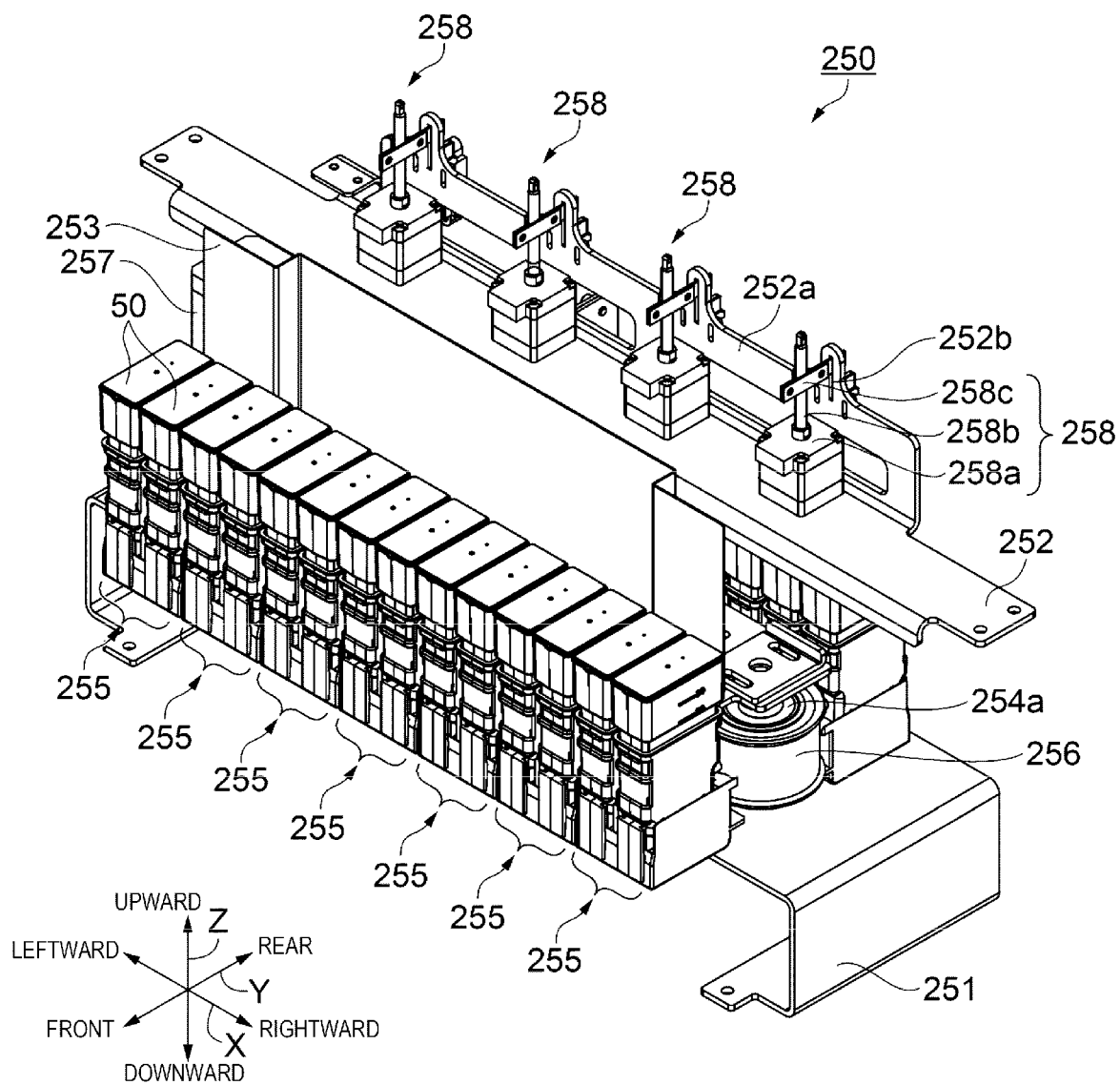
FIG. 19 is a schematic perspective view illustrating a configuration of a reagent supply section of the pathological sample manufacturing apparatus.
Figure 20:
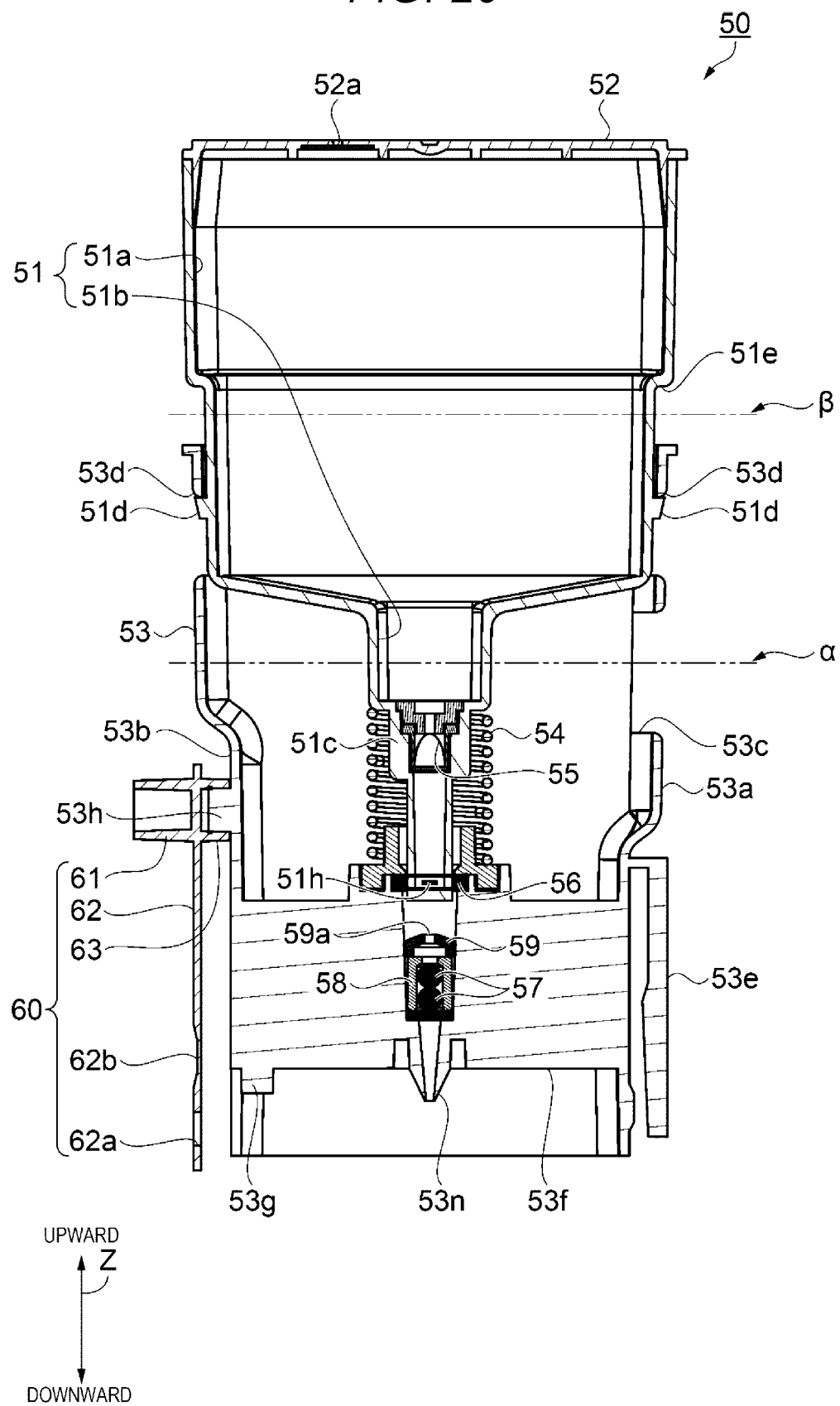
FIG. 20 is a sectional view illustrating a cartridge for a reagent.
Figure 21:
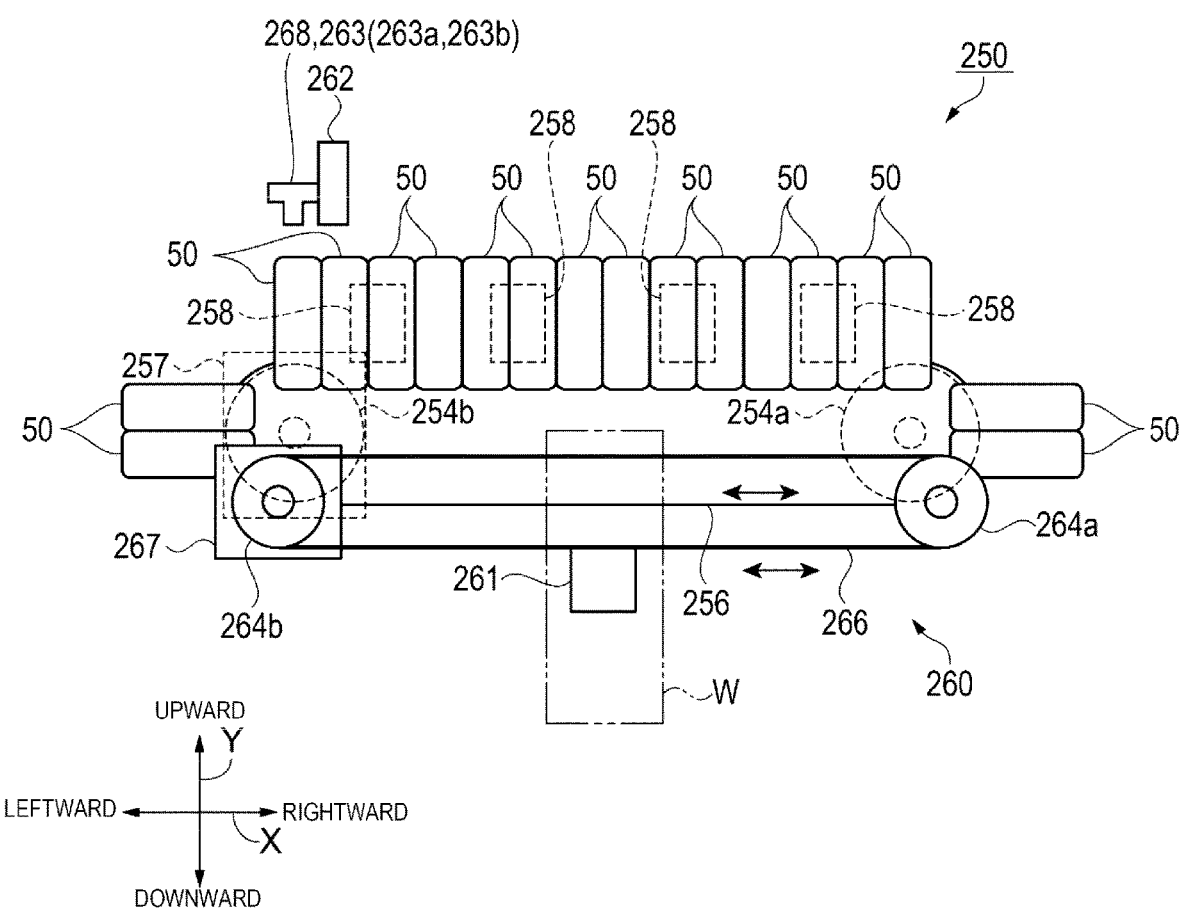
FIG. 21 is a schematic plan view illustrating disposition of respective sections related to the reagent supply section of the pathological sample manufacturing apparatus.
Figure 22:
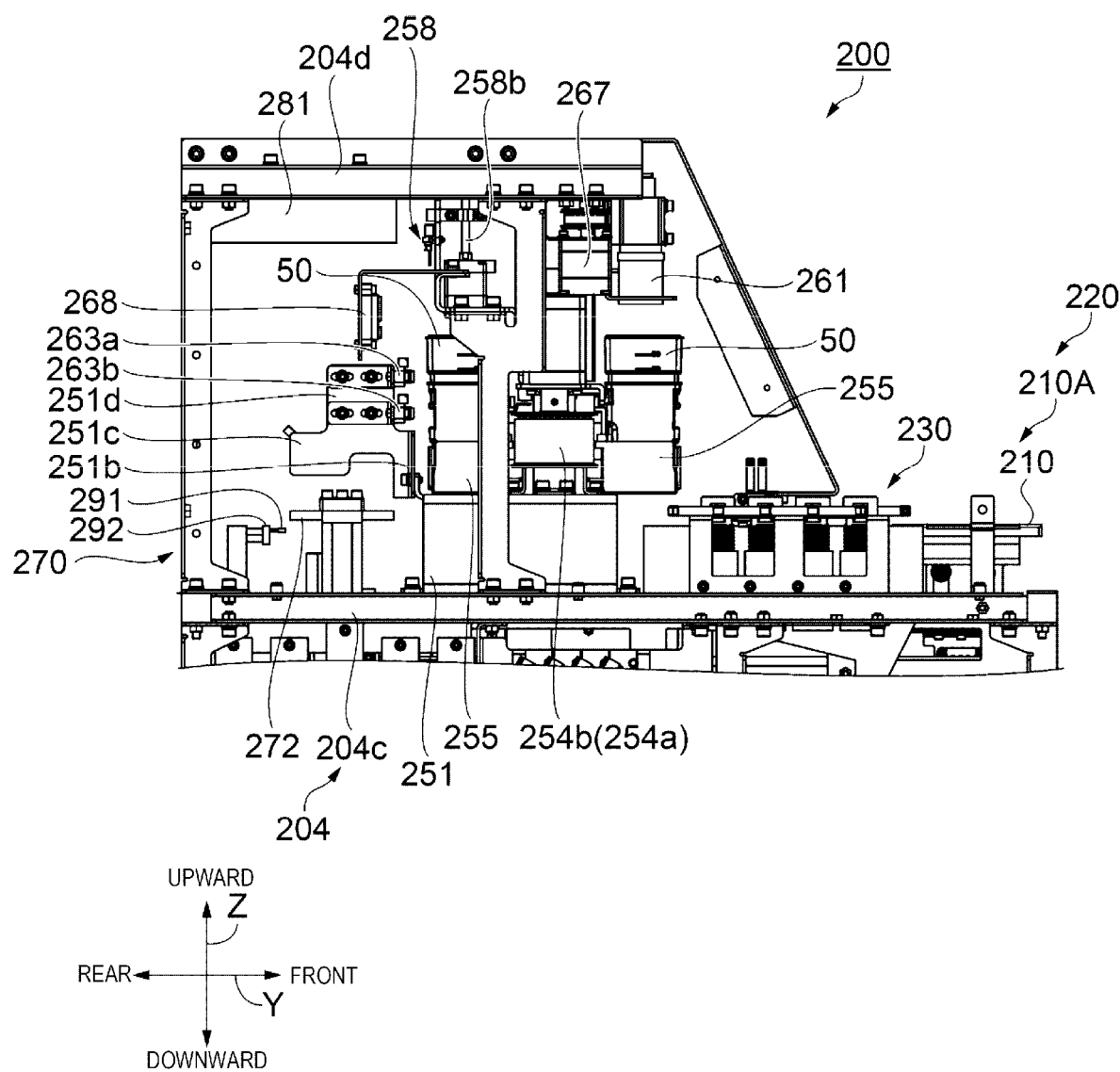
FIG. 22 is a schematic side view illustrating disposition of the respective sections related to the reagent supply section of the pathological sample manufacturing apparatus.

Next, the reagent supply section 250 of the present embodiment will be described with reference to FIGS. 19 to 22. FIG. 19 is a schematic perspective view illustrating a configuration of the reagent supply section of the pathological sample manufacturing apparatus; FIG. 20 is a sectional view illustrating a cartridge for a reagent; FIG. 21 is a schematic plan view illustrating disposition of respective sections related to the reagent supply section of the pathological sample manufacturing apparatus; and FIG. 22 is a schematic side view illustrating disposition of the respective sections related to the reagent supply section of the pathological sample manufacturing apparatus.

The reagent supply section 250 of the present embodiment is a device that supplies a reagent filling a cartridge 50 to the workpiece W mounted on the stage 210A of the stage section 220. As illustrated in FIG. 19, the reagent supply section 250 includes a bridge pier portion 251, a support frame 252, a front surface frame 253, a pair of timing pulleys 254a and 254b, a cartridge holder 255 as a holding portion to which the cartridge 50 is detachably attached, a timing belt 256, a motor 257, and an electric pusher 258.

The bridge pier portion 251 is a structural body supporting the pair of timing pulleys 254a and 254b and the motor 257, and is stretched in the X direction in the third frame 204c of the pathological sample manufacturing apparatus 200. The pair of timing pulleys 254a and 254b are respectively provided on both end sides of a portion of the bridge pier portion 251 extending in the X direction. Of the pair of timing pulleys 254a and 254b, one timing pulley 254a located on the right in the X direction is pivotally supported at the bridge pier portion 251 so as to be rotatable. To the other timing pulley 254b (refer to FIG. 21) located on the left in the X direction, the motor 257 is attached, and rotation thereof is electrically controlled. The motor 257 is, for example, a stepping motor.

The timing belt 256 is stretched between the pair of timing pulleys 254a and 254b. A plurality of (nine) cartridge holders 255 are attached to the timing belt 256. In the present embodiment, two cartridges 50 detachably attached to a single cartridge holder 255, and thus a total of 18 cartridges 50 are attached to the plurality of (nine) cartridge holders 255. When the motor 257 is driven to move the timing belt 256, the plurality of (nine) cartridge holders 255 attached to the timing belt 256 may be freely moved in the X direction. In the present embodiment, a configuration including the pair of timing pulleys 254a and 254b, the timing belt 256, and the motor 257 is an example of a transport portion for the cartridges 50. The number of cartridge holders 255, that is, the number of cartridges 50 which can be attached to the reagent supply section 250 is not limited thereto.

The support frame 252 is provided to stand over the rear end of the bridge pier portion 251 in the Y direction and to extend in the X direction. The support frame 252 has a projection 252a that is bent rearward in the middle in the Y direction and then extends in the Z direction. A plurality of (four) electric pushers 258 are provided with gaps along the projection 252a on the support frame 252. The electric pusher 258 includes a motor 258a, a male screw 258b, and a support portion 258c of the male screw 258b. The motor 258a is, for example, a linearly moving stepping motor, and is screwed to the male screw 258b to move up and down the male screw 258b in the Z direction. Consequently, the electric pusher 258 can press the cartridges 50 attached to the cartridge holder 255 with the male screw 258b from the upper side to the lower side in the Z direction.

The support portion 258c supporting an upper end side of the male screw 258b in the Z direction is provided in each electric pusher 258 in the support frame 252, and is inserted into an upper end side of a slit 252b that is formed at the projection 252a of the support frame 252 so as to extend in the Z direction. Consequently, the support portion 258c can prevent axial deviation caused by rotation of the male screw 258b.

Cartridge

Here, with reference to FIG. 20, a description will be made of the cartridge 50 that ejects a reagent according to the present embodiment. As illustrated in FIG. 20, the cartridge 50 has a rectangular parallelepiped outer shape, and includes a reagent storage portion 51 filled with a reagent, a case 53 that stores the reagent storage portion 51 and in which a nozzle 53n is provided on a bottom surface 53f, and a lid portion 52 of the reagent storage portion 51. An opening portion 53d is provided close to a storage port of one side surface 53a of the case 53. A locking portion 51d is provided on a side surface of the reagent storage portion 51 facing the opening portion 53d. In other words, when the reagent storage portion 51 is stored in the case 53, the locking portion 51d of the reagent storage portion 51 is fitted to the opening portion 53d of the case 53, and thus the reagent storage portion 51 is held in the case 53.

The reagent storage portion 51 has a storage chamber 51a in which a reagent is stored. A lower side of the storage chamber 51a in the Z direction is a narrow portion 51b of which a volume is reduced. A cylindrical projection 51c that communicates with the narrow portion 51b and extends downward is provided at the narrow portion 51b. A valve 55 that causes a reagent to flow toward the projection 51c side or stops the reagent from flowing is provided between the narrow portion 51b and the projection 51c. A front end side of the projection 51c is closed, and an opening portion 51h is formed slightly upward of the front end. A total of two opening portions 51h are respectively formed on the front side and the depth side in the drawing at the front end side of the projection 51c. A reagent is injected into the storage chamber 51a via the storage port of the reagent storage portion 51 which is then covered with the lid portion 52. Thereafter, when the reagent storage portion 51 is inserted and pushed into the case 53, the projection 51c connected to the narrow portion 51b of the storage chamber 51a is held in a state of being movable up and down in the Z direction in a reagent channel connected to the nozzle 53n of the case 53. A coil spring 54 as a biasing portion biasing the reagent storage portion 51 upward against the case 53 in the Z direction is attached to the projection 51c. The locking portion 51d of the reagent storage portion 51 is locked to the opening portion 53d of the case 53, and thus the reagent storage portion 51 is installed in the case 53. Consequently, it is not easy to detach the reagent storage portion 51 from the case 53, and moisture or the like hardly permeates into the cartridge 50 from the outside. A communication hole 52a that communicates with the storage chamber 51a is provided in the lid portion 52. A porous film through which a gas passes and a liquid does not pass is stuck to the communication hole 52a. In other words, even when the cartridge 50 is turned upside down, a reagent does not leak from the communication hole 52a.

A ball chamber 58 accommodating two balls 57 in the Z direction and a contact portion 59 provided on the projection 51c side of the ball chamber 58 are provided in the reagent channel between the projection 51c of the reagent storage portion 51 and the nozzle 53n of the case 53. Since the ball chamber 58 and the contact portion 59 are disposed on the nozzle 53n side of the reagent channel, a predetermined space is formed between the front end of the projection 51c and the contact portion 59. This space is referred to as a stroke chamber. The contact portion 59 is provided with an opening part 59a. Therefore, the stroke chamber communicates with the nozzle 53n via the ball chamber 58 and the contact portion 59. Since the balls 57 are formed by using a material having specific gravity lower than that of the reagent, when the ball chamber 58 is filled with the reagent, the two balls 57 are moved upward to close a communication hole of the ball chamber 58.

The opening portion 51h provided on the front end side of the projection 51c of the reagent storage portion 51 is closed by an O-ring 56 provided on one side of the reagent channel of the case 53 when the reagent storage portion 51 is biased upward against the case 53 by the coil spring 54.

When the lid portion 52 of the cartridge 50 is pressed to push down the reagent storage portion 51 with respect to the case 53, the projection 51c is moved downward, and thus the opening portion 51h closed by the O-ring 56 is opened to the reagent channel. Therefore, the reagent filling the storage chamber 51a flows into the stroke chamber via the valve 55 and the opening portion 51h, and fills the tip of the nozzle 53n further via the contact portion 59 and the ball chamber 58. When pressing of the cartridge 50 is canceled, the reagent storage portion 51 is moved up with respect to the case 53 by the coil spring 54, and thus the opening portion 53d of the case 53 is locked to the locking portion 51d of the reagent storage portion 51 which is then held again. In this case, the valve 55 is closed, and thus the communication hole of the ball chamber 58 is closed by the balls 57 such that the reagent does not leak from the nozzle 53n. In a state in which the reagent fills the tip of the nozzle 53n, when the lid portion 52 of the cartridge 50 is pressed, and the reagent storage portion 51 is pushed down with respect to the case 53 until the projection 51c abuts on the contact portion 59, the reagent filling the reagent channel including the stroke chamber is ejected from the nozzle 53n. In other words, an amount of the reagent ejected from the nozzle 53n through pressing of the cartridge 50 performed once is defined depending on a volume of the reagent filling the stroke chamber. In other words, a predetermined amount of the reagent can be ejected from the nozzle 53n through pressing of the cartridge 50 performed once.

The reagent storage portion 51 of the cartridge 50 storing the reagent is transparent or translucent, and is made with polyethylene or polypropylene by taking into consideration chemical resistance. An opening portion 53c is provided on one side surface 53a of the case 53 storing the reagent storage portion 51 under the opening portion 53d. The opening portion 53c is provided at a position facing the narrow portion 51b of the storage chamber 51a of the reagent storage portion 51.

The cartridge 50 of the present embodiment is provided with two optical paths for optically detecting an amount of the reagent filling the reagent storage portion 51. One of the two optical paths is an optical path α indicated by a dashed line in FIG. 20, which passes through the opening portion 53c at the position facing the narrow portion 51b. The other of the two optical paths is an optical path β indicated by a dashed line in FIG. 20, which passes through a portion 51e that is slightly reduced in width in the reagent storage portion 51 protruding upward from the case 53.

A hook 53e is provided under the opening portion 53c of the side surface 53a of the case 53 of the cartridge 50. Therefore, as illustrated in FIG. 19, when the cartridge 50 is inserted into the cartridge holder 255, a part of the cartridge holder 255 is sandwiched between the side surface 53a of the cartridge 50 and the hook 53e, and thus the case 53 can be fixed not to be moved by attaching the cartridge 50 to the cartridge holder 255. An opening is provided on the bottom surface of the cartridge holder 255 at a position corresponding to the nozzle 53n.

A protrusion 53h is provided on the other side surface 53b facing one side surface 53a of the case 53. A nozzle cap 60 is fitted and mounted on the protrusion 53h. The nozzle cap 60 has a cap part 61 that is attached to and encloses the nozzle 53n of the case 53, and a support plate 62 provided at one end of the cap part 61. A fitting part 63 fitting to the protrusion 53h of the case 53 is provided at one end of the support plate 62 on an opposite side to the cap part 61. A through-hole 62a is provided at the other end of the support plate 62. A thin part 62b of which a thickness is reduced is provided near the through-hole 62a of the support plate 62. In FIG. 20, the nozzle cap 60 is detachably attached to the case 53, but, actually, a protrusion 53g provided on the bottom surface 53f of the case 53 is inserted into the through-hole 62a of the support plate 62, and the protrusion 53g is thermally welded and fixed to the support plate 62.

In handling of the cartridge 50 filled with the reagent, the nozzle 53n is enclosed with the nozzle cap 60 in a stage before the cartridge 50 is attached to the cartridge holder 255. Consequently, the tip of the nozzle 53n is prevented from being contaminated due to contact with other substances. In a case where the cartridge 50 is attached to the cartridge holder 255, the cap part 61 is removed from the nozzle 53n, the support plate 62 is bent, the fitting part 63 is fitted to the protrusion 53h of the case 53, and thus the nozzle cap 60 is fixed to the case 53 of the cartridge 50. The support plate 62 of the nozzle cap 60 is thermally welded to the protrusion 53g of the case 53, and thus the nozzle cap 60 can be prevented from being lost. The nozzle cap 60 is formed by using a resin material such as polyethylene or polypropylene in the same manner as the reagent storage portion 51 or the case 53.

As illustrated in FIG. 21, when the motor 257 is driven to move the timing belt 256 in the X direction, the cartridge 50 attached to the cartridge holder 255 may be moved to a position overlapping the electric pusher 258. The electric pusher 258 presses the lid portion 52 of the cartridge 50 as described above, and thus ejects the reagent from the nozzle 53n of the cartridge 50. In this case, when the stage section 220 moves the stage 210A to the position facing the reagent supply section 250, a predefined amount of the reagent may be dropped onto the tissue sample Ts of the workpiece W mounted on the stage 210A with high accuracy.

As illustrated in FIG. 21, a plurality of sensors and a barcode reader 262 are provided side by side on the rear side of the reagent supply section 250 in the Y direction and on the left side in the X direction. The plurality of sensors include two residual quantity detection sensors 263a and 263b detecting a residual quantity of the reagent in the cartridge 50, and a height detection sensor 268 detecting a height of the cartridge 50.

An imaging unit 260 imaging the workpiece W is provided in front of the reagent supply section 250 in the Y direction. The imaging unit 260 is configured to include a CCD 261 as an imaging portion, a pair of timing pulleys 264a and 264b, a timing belt 266, and a motor 267.

The pair of timing pulleys 264a and 264b are disposed to be arranged in the Y direction and partially overlap the pair of timing pulleys 254a and 254b of the reagent supply section 250 in a plan view. The timing belt 266 is stretched between the pair of timing pulleys 264a and 264b in the X direction. The CCD 261 is attached to the front side of the timing belt 266 stretched in the X direction so as to image a lower side in the Z direction. The left timing pulley 264b of the pair of timing pulleys 264a and 264b in the X direction is attached with the motor 267.

When the motor 267 is driven, the CCD 261 fixed to the timing belt 266 may be moved in the X direction. In other words, when the motor 267 is controlled to be driven, in each of the plurality of (four) stage sections 220, the CCD 261 may be disposed at a position corresponding to the stage 210A moved to the reagent supply section 250 by the stage transport mechanism. The workpiece W mounted on the stage 210A is imaged by using the CCD 261, and thus information regarding a state of the tissue sample Ts fixed to the workpiece W or information regarding the tissue sample Ts written on the marking region 3 may be acquired as an image. A light source such as an LED that illuminates the workpiece W when the CCD 261 images the workpiece W may be provided on the timing belt 266 along with the CCD 261.

Next, with reference to FIG. 22, a description will be made of a configuration of each of the barcode reader 262 and the plurality of sensors related to the cartridge 50.

As illustrated in FIG. 22, a leg portion 251b stands on the rear side in the Y direction with respect to the bridge pier portion 251 supporting the pair of timing pulleys 254a and 254b of the reagent supply section 250 from below. A height of the leg portion 251b is set not to contact with the cartridge holder 255. A support portion 251c extending rearward in the Y direction from the leg portion 251b is provided, and the barcode reader 262 and the plurality of sensors are provided on the support portion 251c. Among the plurality of sensors, the residual quantity detection sensor 263a and the residual quantity detection sensor 263b are attached, in this order from the top, to a support plate 251d that is provided at the support portion 251c and extends in the Z direction. The height detection sensor 268 is provided over the residual quantity detection sensor 263a.

In the present embodiment, a seal indicating a barcode related to a reagent is stuck to the hook 53e of the case 53 of the cartridge 50. When the motor 257 is driven to move the cartridge holder 255, the cartridge 50 may face the barcode reader 262. The barcode stuck to the cartridge 50 is read by the barcode reader 262. The operation in which the barcode is read by using the barcode reader 262 is performed on each of a total of 18 cartridges 50 set in the plurality of cartridge holders 255 of the reagent supply section 250. A barcode assigned to the cartridge 50 is a one-dimensional barcode or a two-dimensional barcode, and, as the barcode reader 262, a device that can read such a barcode is selected.

A position of the barcode in the cartridge 50 is not limited to the hook 53e of the case 53. A position of the barcode reader 262 may be set such that the cartridge 50 and the barcode reader 262 face each other depending on a position of the barcode.

When the motor 257 is driven to move the cartridge holder 255, the cartridge 50 may face the two residual quantity detection sensors 263a and 263b and the height detection sensor 268.

Of the two residual quantity detection sensors 263a and 263b, the residual quantity detection sensor 263a is attached to the support plate 251d at a position corresponding to the optical path β (refer to FIG. 20) facing the reagent storage portion 51 protruding upward from the case 53 of the cartridge 50. The residual quantity detection sensor 263b is attached to the support plate 251d at a position corresponding to the optical path α (refer to FIG. 20) facing the opening portion 53c of the case 53 of the cartridge 50.

Each of the two residual quantity detection sensors 263a and 263b includes a light emitting portion and a light receiving portion, receives reflected light in which light emitted from the light emitting portion is reflected by a target object, with the light receiving portion, and thus detects an intensity of the reflected light such that the presence or absence of a reagent is optically detected.

As described above, the reagent storage portion 51 filled with the reagent in the cartridge 50 is formed by using a light-transmissive member that is transparent or translucent. Therefore, when the residual quantity detection sensor 263a is used, the presence or absence of the reagent in the storage chamber 51a of the reagent storage portion 51 may be detected. When the residual quantity detection sensor 263b is used, the presence or absence of the reagent in the narrow portion 51b of the reagent storage portion 51 may be detected.

Since a portion of the cartridge 50 facing the residual quantity detection sensor 263a is the storage chamber 51a close to the narrow portion 51b, when it is detected by the residual quantity detection sensor 263a that there is no reagent, this indicates that an amount of the reagent in the storage chamber 51a is reduced to a half or less, and a replacement time of the cartridge 50 comes.

Since the opening portion 53c of the cartridge 50 facing the residual quantity detection sensor 263b is open to the position facing the narrow portion 51b, when it is detected by the residual quantity detection sensor 263b that there is no reagent, this indicates that an amount of the reagent in the storage chamber 51a reaches the limit, and thus the cartridge 50 is required to be replaced. As mentioned above, when the two residual quantity detection sensors 263a and 263b are used, a residual quantity of the reagent in the cartridge 50 can be detected with high accuracy, and thus it is possible to thoroughly manage a residual quantity of the reagent.

The height detection sensor 268 is attached at a position where a surface of the lid portion 52 of the cartridge 50 set in the cartridge holder 255 is detectable. As described above, the cartridge 50 has a configuration in which the lid portion 52 is pressed from above by the electric pusher 258, and thus a predetermined amount of a reagent is ejected from the nozzle 53n. When the cartridge 50 is not accurately set in the cartridge holder 255, and the lid portion 52 is located above a predetermined position in the Z direction, even though the lid portion 52 is pressed once by the electric pusher 258, there is concern that a predetermined amount of a reagent may not be accurately ejected from the nozzle 53n. When the motor 257 is driven to move the cartridge holder 255, there is concern that the male screw 258b of the electric pusher 258 may come into contact with the lid portion 52 of the cartridge 50. A position of the lid portion 52 of the cartridge 50, that is, a height of the cartridge 50 set in the cartridge holder 255 is detected by using the height detection sensor 268, and thus it is possible to prevent the above problem.

As illustrated in FIG. 22, the CCD 261 of the imaging unit 260 is disposed in front of the motor 267 in the Y direction which moves the CCD 261 in the X direction. A probe 291 applying a potential to the lower electrode 210 of the stage 210A transported to the electric field stirring section 270 by the stage transport mechanism of the stage section 220 is provided on the rear side of the third frame 204c. The probe 291 is movable in the front-rear direction (Y direction) in a state of being brought into contact with the lower electrode 210. A configuration related to the probe 291 will be described later.

Electric Field Stirring Section

Figure 23:
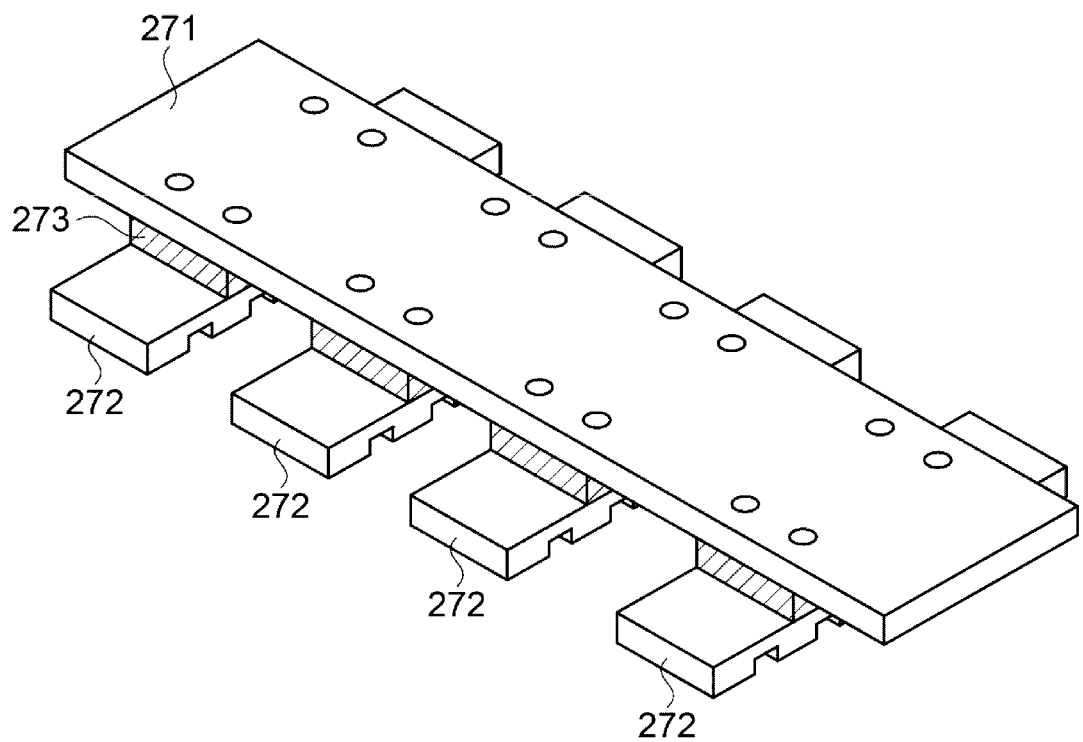
FIG. 23 is a schematic perspective view illustrating a configuration of an electric field stirring section of the pathological sample manufacturing apparatus.
Figure 24:
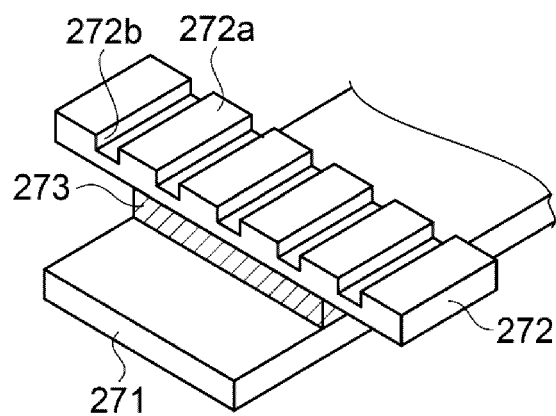
FIG. 24 is a schematic perspective view illustrating a configuration of an upper electrode of the electric field stirring section.
Figure 25A:
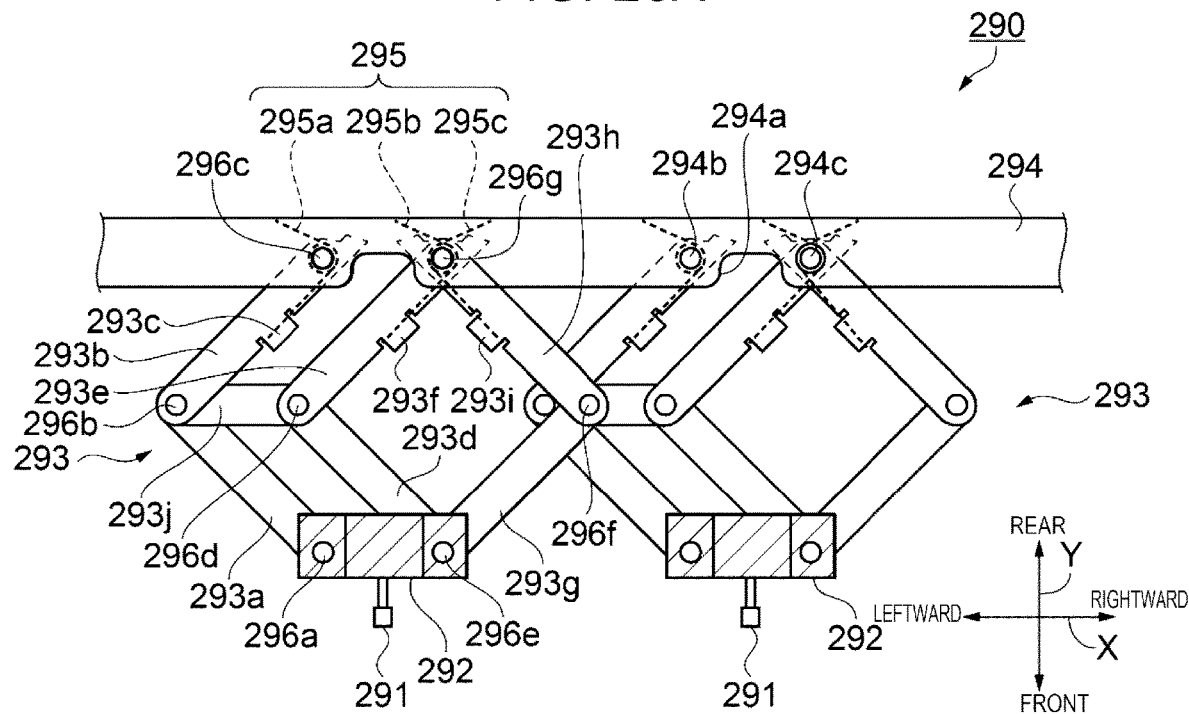
FIG. 25A is a schematic plan view illustrating a probe movement mechanism of the electric field stirring section.
Figure 25B:
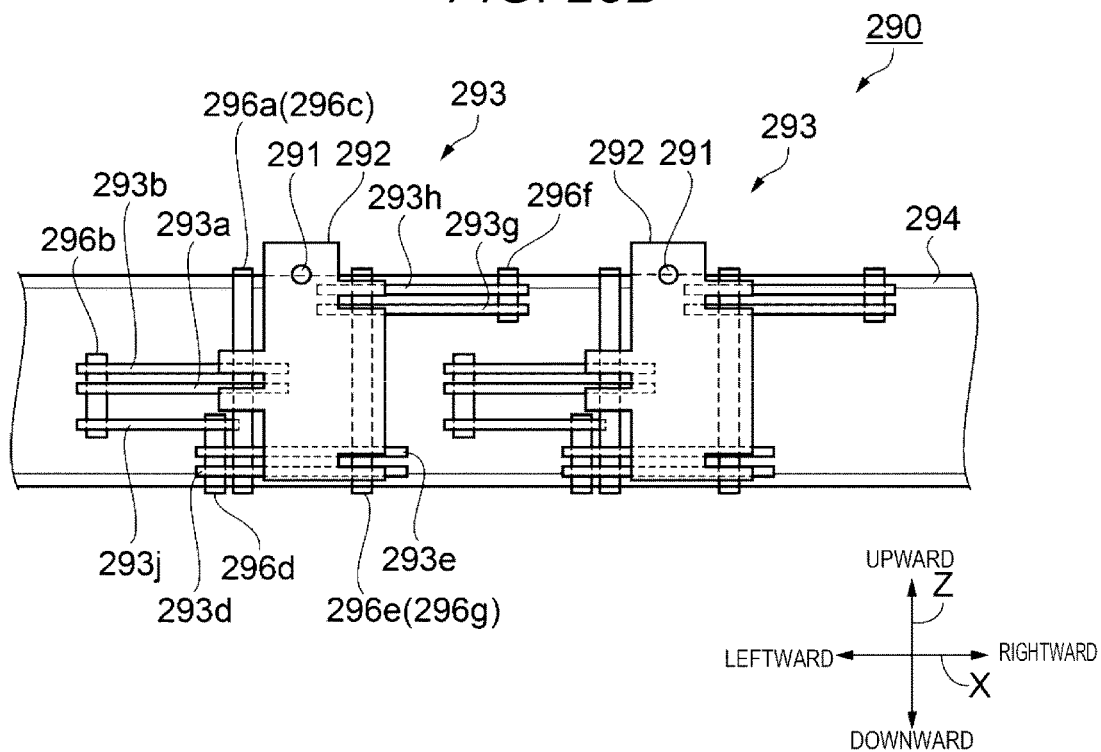
FIG. 25B is a schematic front view illustrating the probe movement mechanism of the electric field stirring section.

Next, the electric field stirring section 270 will be described with reference to FIGS. 23, 24, 25A, and 25B. FIG. 23 is a schematic perspective view illustrating a configuration of the electric field stirring section of the pathological sample manufacturing apparatus, and FIG. 24 is a schematic perspective view illustrating a configuration of the upper electrode of the electric field stirring section. FIG. 25A is a schematic plan view illustrating a probe movement mechanism of the electric field stirring section, and FIG. 25B is a schematic front view illustrating the probe movement mechanism of the electric field stirring section.

As illustrated in FIG. 23, the electric field stirring section 270 has four upper electrodes 272 provided to correspond to the four stage sections 220, and a tabular electrode support portion 271 supporting the four upper electrodes 272 via insulation portions 273. The upper electrode 272 has a rectangular shape of which one lateral part is longer than the other lateral part. The tabular electrode support portion 271 is provided in the third frame 204c of the pathological sample manufacturing apparatus 200 such that the elongated upper electrodes 272 are disposed along the front-rear direction (Y direction) at positions respectively corresponding to the four stage sections 220 in the leftward-rightward direction (X direction).

As illustrated in FIG. 24, a plurality of (five in this case) grooves 272b each extending along the short side are formed with gaps in the longitudinal direction on an electrode surface 272a of the elongated upper electrode 272. The plurality of grooves 272b are formed at an equal interval in the longitudinal direction. A width of the groove 272b in the longitudinal direction is, for example, 8 mm, and a depth thereof is, for example, 4 mm. An arrangement pitch of the grooves 272b in the longitudinal direction is, for example, 20 mm. When the stage 210A is moved to the electric field stirring section 270 by the stage transport mechanism, the lower electrode 210 of the stage 210A is disposed to face the upper electrode 272. In this case, the probe 291 illustrated in FIG. 22 is brought into contact with the lower electrode 210. In the pathological sample manufacturing apparatus 200 of the present embodiment, contact between the lower electrode 210 and the probe 291 is electrically detected, then an electric signal is applied to the upper electrode 272 by the electric field generation section 281, and thus an electric field is generated between the lower electrode 210 and the upper electrode 272.

Probe Movement Mechanism

As illustrated in FIGS. 25A and 25B, a probe movement mechanism 290 includes the probe 291, a base portion 292 on which the probe 291 stands and which is formed by using an insulating material such as Bakelite, a support plate 294, a leg portion 293 connecting the base portion 292 to the support plate 294, and torsion springs 295 as a biasing portion that biases the base portion 292 in the front-rear direction (Y direction) against the support plate 294 via the leg portion 293. When a configuration including the probe 291, the base portion 292, and the leg portion 293 is referred to as a set of probe unit, in the present embodiment, four sets of probe units are provided on the support plate 294, but, for convenience of description, two sets of probe units are illustrated in FIGS. 25A and 25B. A notch part 294a provided on a rib of the support plate 294 defines a position of the probe unit in the leftward-rightward direction (X direction), and two through-holes 294b and 294c are provided with the notch part 294a interposed therebetween in the X direction.

The probe 291 is attached to the base portion 292 so as to protrude frontward in the Y direction. The leg portion 293 has a first leg part 293a, a second leg part 293b, a third leg part 293d, a fourth leg part 293e, a fifth leg part 293g, a sixth leg part 293h, and a connection part 293j, and is attached between the base portion 292 and the support plate 294 so as to be bendable in the leftward-rightward direction (X direction).

Specifically, one end of the first leg part 293a is pivotally supported by a shaft 296a on the left end side of the base portion 292 in the leftward-rightward direction (X direction). The other end of the first leg part 293a and one end of the second leg part 293b are pivotally supported by a shaft 296b. The other end of the second leg part 293b is pivotally supported by a shaft 296c penetrating through one through-hole 294b of the support plate 294. A hook 293c is formed at the center of one lateral part of the second leg part 293b in the longitudinal direction. The torsion spring 295a pivotally supported by the shaft 296c is stretched between a sidewall of the support plate 294 and the hook 293c.

One end of the third leg part 293d is pivotally supported by a shaft 296e on the right end side of the base portion 292 in the leftward-rightward direction (X direction). The other end of the third leg part 293d and one end of the fourth leg part 293e are pivotally supported by a shaft 296d. The other end of the fourth leg part 293e is pivotally supported by a shaft 296g penetrating through the other through-hole 294c of the support plate 294. A hook 293f is formed at the center of one lateral part of the fourth leg part 293e in the longitudinal direction. The torsion spring 295b pivotally supported by the shaft 296g is stretched between the sidewall of the support plate 294 and the hook 293f. The connection part 293j is provided between the shaft 296b and the shaft 296d, and both ends of the connection part 293j is pivotally supported.

One end of the fifth leg part 293g is pivotally supported by the shaft 296e on the right end side of the base portion 292 in the leftward-rightward direction (X direction). The other end of the fifth leg part 293g and one end of the sixth leg part 293h are pivotally supported by a shaft 296f. The other end of the sixth leg part 293h is pivotally supported by the shaft 296g penetrating through the other through-hole 294c of the support plate 294. A hook 293i is formed at the center of one lateral part of the sixth leg part 293h in the longitudinal direction. The torsion spring 295c pivotally supported by the shaft 296g is stretched between the sidewall of the support plate 294 and the hook 293i.

The three torsion springs 295a, 295b, and 295c will be collectively referred to as torsion springs 295. When the lower electrode 210 is pushed rearward in the Y direction from a position where the tip of the probe 291 abuts on the lower electrode 210, the leg portion 293 is bent in the X direction, and thus a length thereof in the Y direction is reduced. Since the leg portion 293 is bent, and thus the torsion spring 295 is deflected, the leg portion 293 is biased by the torsion spring 295 in a direction in which bending thereof is canceled, and thus the base portion 292 is pressed frontward in the Y direction. Therefore, a state in which the lower electrode 210 is brought into contact with the probe 291 is maintained in a state in which the lower electrode 210 is pushed rearward in the Y direction from the position where the lower electrode 210 abuts on the probe 291. Even though the lower electrode 210 is moved frontward from the state of being pushed in the Y direction, the state in which the lower electrode 210 and the probe 291 are brought into contact with each other is maintained due to biasing of the torsion spring 295 against the leg portion 293 until deflection of the torsion spring 295 is canceled. In the electric field stirring section 270, in a state in which the upper electrode 272 faces the stage 210A, that is, the lower electrode 210, even though the lower electrode 210 abuts on the probe 291 and is then reciprocally moved in the Y direction, contact between the lower electrode 210 and the probe 291 is maintained. In other words, an initial position in the Y direction of the base portion 292 supporting the probe 291 with respect to the support plate 294 of the probe movement mechanism 290 is adjusted by a length of the leg portion 293 in the Y direction such that the contact between the lower electrode 210 and the probe 291 is maintained during reciprocal movement. A stroke of reciprocal movement during which contact between the lower electrode 210 and the probe 291 is maintained in the probe movement mechanism 290 of the present embodiment is about 40 mm.

As illustrated in FIG. 25B, in the upward-downward direction (Z direction), the first leg part 293a and the second leg part 293b are disposed over the third leg part 293d and the fourth leg part 293e. The fifth leg part 293g and the sixth leg part 293h are disposed over the first leg part 293a and the second leg part 293b. Therefore, in the probe units adjacent to each other in the X direction, even though the probe 291 of one probe unit is moved in the front-rear direction (Y direction) due to bending of the leg portion 293, the probe 291 of one probe unit does not interfere with the leg portion 293 of the other probe unit. In other words, the probe units adjacent to each other are configured such that the mutual leg portions 293 do not interfere with each other in the leftward-rightward direction (X direction), and thus it is possible to easily adjust a length of a stroke in which the probe 291 is reciprocally movable in the front-rear direction (Y direction) by adjusting a length of the leg portion 293.

Circuit Configuration of Electric Field Stirring Section

Figure 26:
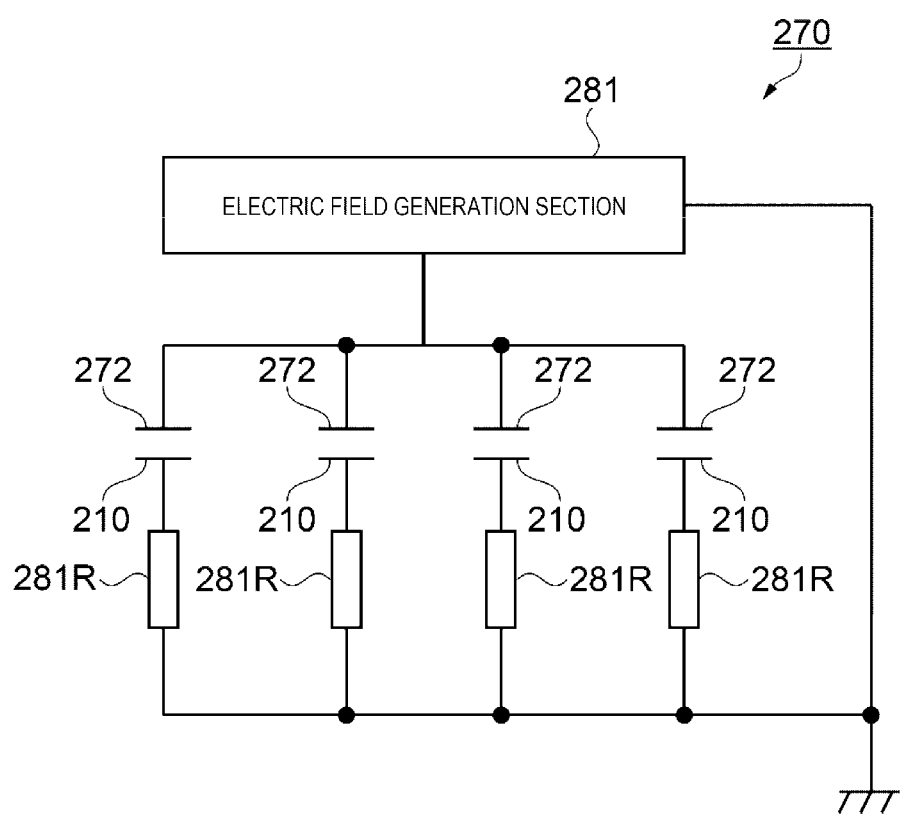
FIG. 26 is a diagram illustrating a circuit configuration of the electric field stirring section.

Next, with reference to FIG. 26, a description will be made of a circuit configuration of the electric field stirring section 270. FIG. 26 is a diagram illustrating a circuit configuration of the electric field stirring section. As described above, the pathological sample manufacturing apparatus 200 of the present embodiment can simultaneously or separately manufacture a plurality of pathological samples by mounting the workpiece W on each of the stages 210A of the plurality of (four, in this case) stage sections 220. Therefore, when the stage section 220 processing a single workpiece W is referred to as a lane, the pathological sample manufacturing apparatus 200 has a plurality of (four, in this case) lanes that can process the workpieces W. As illustrated in FIG. 23, in the electric field stirring section 270 of the present embodiment, the upper electrode 272 is provided in each of the four lanes. On the other hand, as illustrated in FIG. 26, the four upper electrodes 272 are electrically coupled in parallel to the electric field generation section 281. In the electric field stirring section 270, the four lower electrodes 210 disposed to face the four upper electrodes 272 are coupled in parallel to the electric field generation section 281 via resistive elements 281R, and have a GND potential. A resistance value of the resistive element 281R is, for example, 1 megaohm (MΩ).

Since the electric field stirring section 270 has the electrical configuration, for example, while electric field stirring is being performed in one of the four lanes, even though electric field stirring is started in other lanes, and thus an electrical load on the electric field generation section 281 is increased, it is possible to prevent the occurrence of a leaking current in other lanes due to the increase of the electrical load. In other words, it is possible to suppress a variation in a potential of an electric signal applied to the upper electrodes 272 of other lanes due to the leaking current. When the resistive element 281R is coupled to the upper electrode 272, a potential of an electric signal applied to the upper electrode 272 is reduced, and thus the resistive element 281R is preferably coupled to the lower electrode 210.

As described above, the pathological sample manufacturing apparatus 200 of the present embodiment has the same configuration as that of the electric field stirring apparatus 100 of the first embodiment. Specifically, the pathological sample manufacturing apparatus 200 includes the lower electrode 210 functioning as the first electrode, the upper electrode 272 functioning as the second electrode, the stage transport mechanism of the stage section 220 as the movement mechanism that reciprocally moves the lower electrode 210 in the second direction orthogonal to the first direction in which the grooves 272b of the upper electrode 272 are formed, and the electric field generation section 281.

Figure 27:
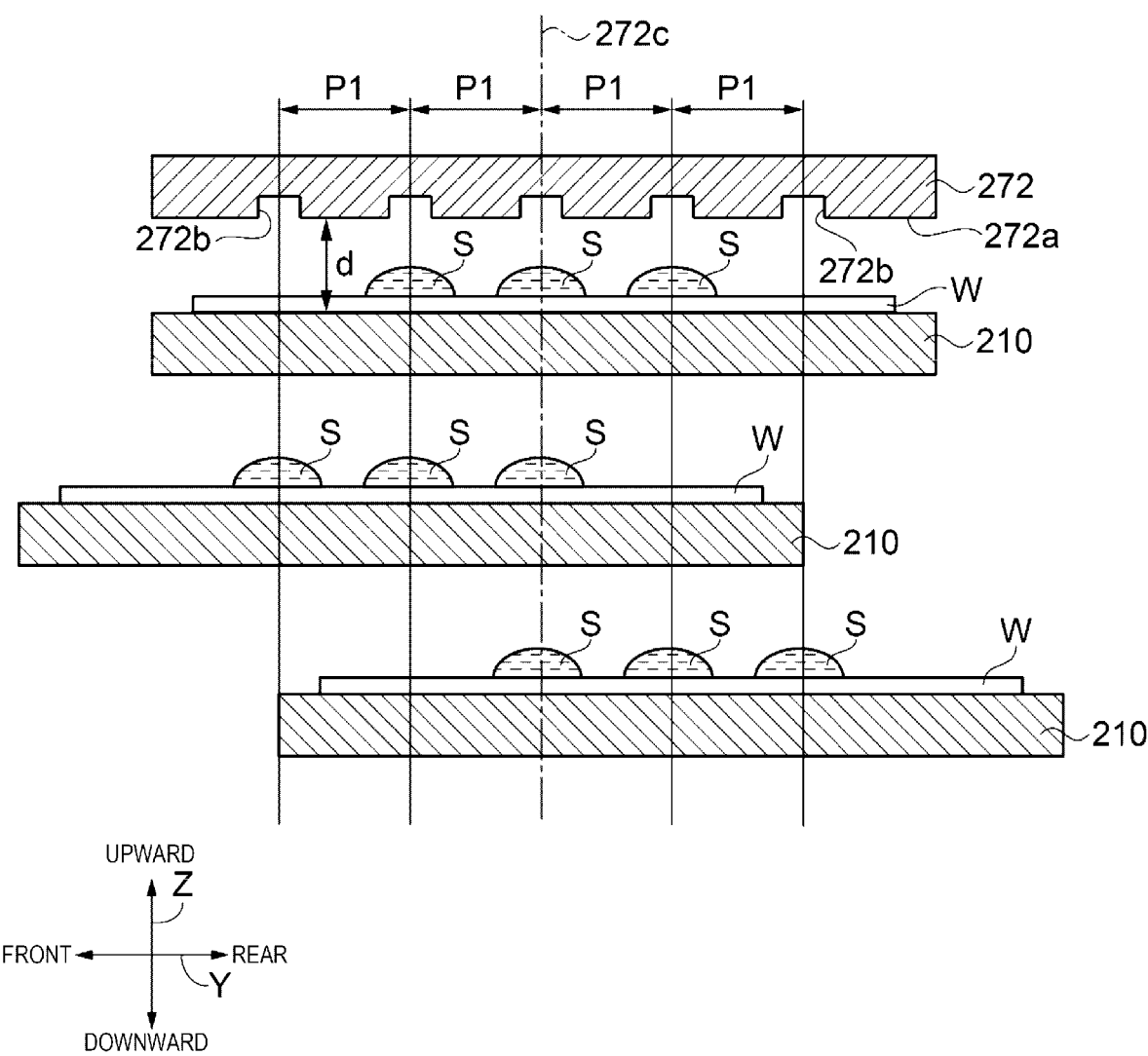
FIG. 27 is a schematic sectional view illustrating an electric field stirring method in the pathological sample manufacturing apparatus.

With reference to FIG. 27, a description will be made of an electric field stirring method using the pathological sample manufacturing apparatus 200. FIG. 27 is a schematic sectional view illustrating an electric field stirring method in the pathological sample manufacturing apparatus. Specifically, FIG. 27 is a schematic sectional view illustrating reciprocal movement of the lower electrode 210 relative to the upper electrode 272 in the front-rear direction (Y direction) during electric field stirring.

As illustrated in FIG. 27, the workpiece W on which a maximum of three droplets S are formed in the front-rear direction (Y direction) may be mounted on the lower electrode 210. An arrangement pitch of the three droplets S in the front-rear direction (Y direction) on the workpiece W is the same as an arrangement pitch P1 of a plurality of (five) grooves 272b formed on the upper electrode 272 in the front-rear direction (Y direction). As described above, the arrangement pitch P1 of the grooves 272b is, for example, 20 mm, a width of the groove 272b is, for example, 8 mm, and a depth thereof is, for example, 4 mm. A length of the predetermined region 2e in which the droplet S is formed in the front-rear direction (Y direction) in this case is, for example, 12 mm. In other words, an inner diameter of the water repellent ring 2 is φ12 mm. An inner diameter of the water repellent ring 2 is not limited thereto.

In the electric field stirring section 270, first, the lower electrode 210 and the upper electrode 272 are disposed to face each other with the preset inter-electrode distance d in the upward-downward direction. The lower electrode 210 and the upper electrode 272 are disposed to face each other such that, among the three droplets S, the central droplet S faces the central groove 272b among the five grooves 272b of the upper electrode 272. A position where the central droplet S overlaps a central line 272c of the central groove 272b is the origin in the electric field stirring method of the present embodiment. During electric field stirring in which an electric field is generated between the lower electrode 210 and the upper electrode 272, the stage transport mechanism of the stage section 220 reciprocally moves the stage 210A, that is, the lower electrode 210 in the Y direction relative to the origin at the same length as the arrangement pitch P1 of the droplets S. In a case where reciprocal movement is performed as mentioned above, the three droplets S formed on the workpiece W respectively face the grooves 272b formed on the upper electrode 272 even when the lower electrode 210 is moved frontward relative to the origin with the arrangement pitch P1 and when the lower electrode 210 is moved rearward relative to the origin with the arrangement pitch P1. In other words, a node of the droplet S vibrated in the upward-downward direction due to the electric field stirring is swung in the front-rear direction with the arrangement pitch P1. Consequently, it is possible to efficiently and uniformly stir a maximum of three droplets S formed on the workpiece W.

An arrangement pitch of a plurality of droplets S formed on the workpiece W in the Y direction may not accurately match the arrangement pitch P1 of the grooves 272b. As described above, a size or a position of the predetermined region 2e in which the droplet S is formed is defined depending on the water repellent ring 2 formed on the substrate 1. Even though a position of the water repellent ring 2 formed on the substrate 1 slightly varies, when a range of reciprocal movement of the lower electrode 210 in the Y direction is twice the arrangement pitch P1 of the grooves 272b, each of a plurality of droplets S can be subjected to sufficient electric field stirring. A range of reciprocal movement of the lower electrode 210 in the Y direction is not limited to twice the arrangement pitch P1 of the grooves 272b, and, as described in the first embodiment, the lower electrode 210 may be reciprocally moved in the Y direction relative to the origin up to a position where the central line 272c of the groove 272b is deviated from the outer edge 2ed of the predetermined region 2e in which the droplet S is formed on the workpiece W.

According to the electric field stirring method for the droplet S, using the pathological sample manufacturing apparatus 200, a node of vibration of the droplet S vibrated in the upward-downward direction due to electric field stirring can be swung in the front-rear direction (Y direction) at a distance that is twice the arrangement pitch P1 larger than a length of the predetermined region 2e of the droplet S formed on the workpiece W. Consequently, it is possible to efficiently and uniformly subject each of the three droplets S formed on the workpiece W to electric field stirring.

Exterior

Figure 28:
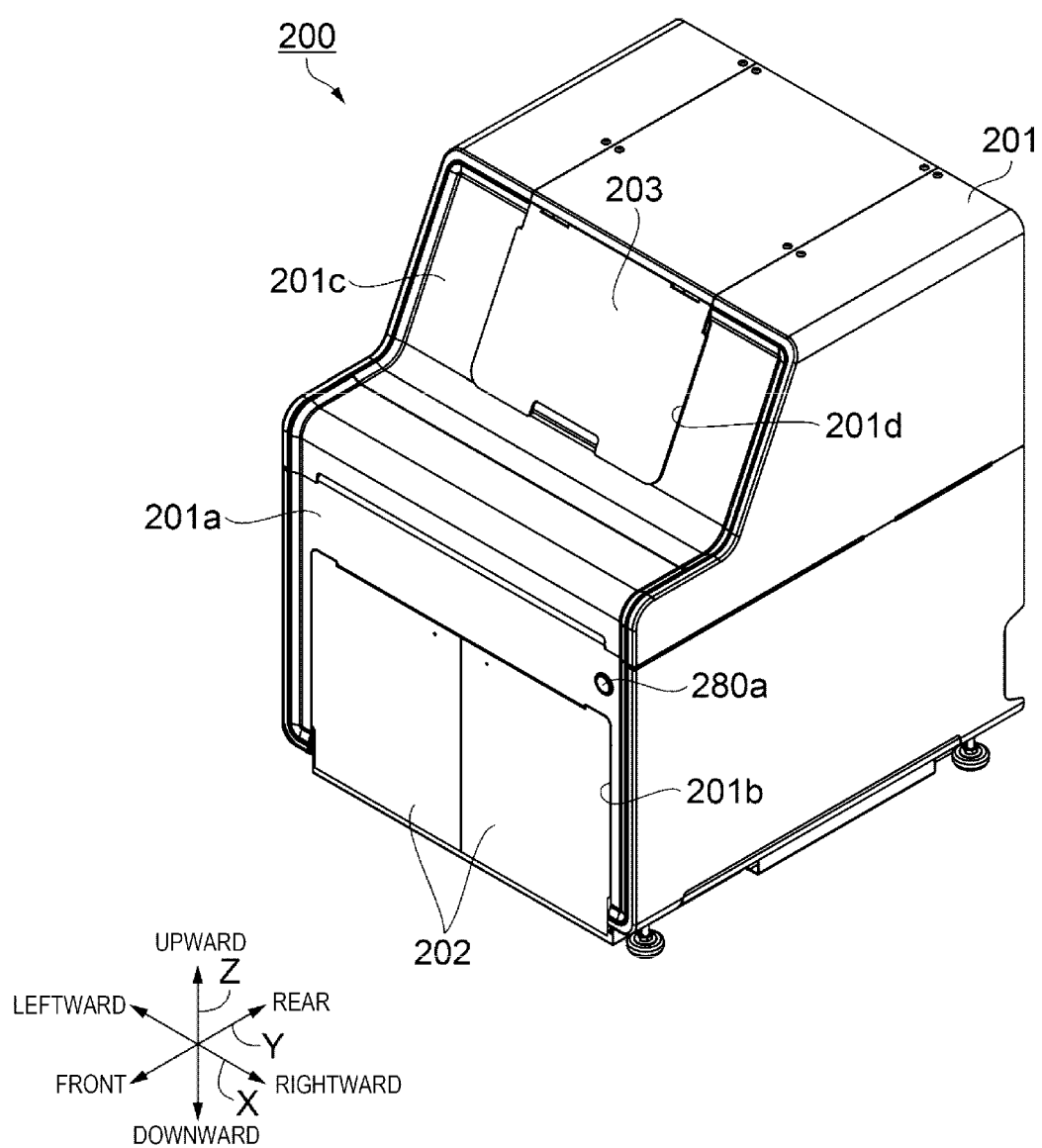
FIG. 28 is a schematic perspective view illustrating an exterior of the pathological sample manufacturing apparatus.
Figure 29:
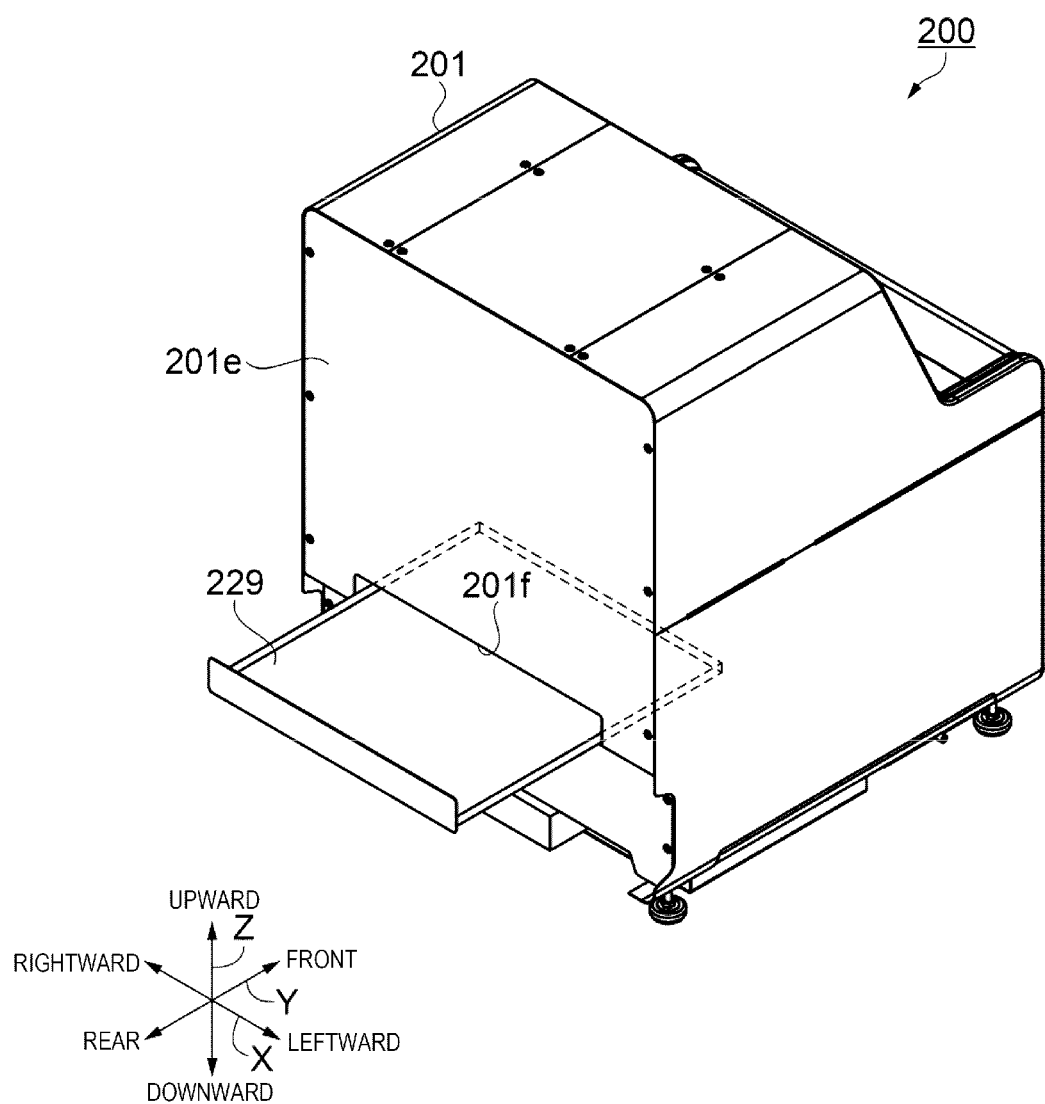
FIG. 29 is a schematic perspective view illustrating the exterior of the pathological sample manufacturing apparatus.

Next, with reference to FIGS. 28 and 29, a description will be made of an exterior of the pathological sample manufacturing apparatus 200 of the present embodiment. FIGS. 28 and 29 are schematic perspective views illustrating an exterior of the pathological sample manufacturing apparatus. Specifically, FIG. 28 illustrates a front side of the exterior of the pathological sample manufacturing apparatus, and FIG. 29 illustrates a rear side of the exterior of the pathological sample manufacturing apparatus.

As illustrated in FIG. 28, the pathological sample manufacturing apparatus 200 of the present embodiment has an exterior case 201 containing the frame 204, and the tanks 205 to 208, the stage section 220, the cleaning section 230, the reagent supply section 250, the electric field stirring section 270, the circuit section 280, and the electric field generation section 281 provided in the frame 204, illustrated in FIG. 10.

On a front surface portion 201a of the exterior case 201, an opening 201b is provided to correspond to the tank storage section 209, and a pair of doors 202 is attached to the opening 201b. When the pair of doors 202 are opened from the center rightward and leftward, each of the tanks 205, 206, 207, and 208 may be attached to the tank storage section 209, or any one of the attached tanks 205, 206, 207, and 208 may be extracted. A power switch 280a is provided at an upper right corner of the front surface portion 201a.

An opening 201d corresponding to the reagent supply section 250 is provided on a front portion 201c located upward of the front surface portion 201a of the exterior case 201. A door 203 that is opened upward with an upper lateral part of the opening 201d as a start point is attached to the opening 201d. The cartridge 50 filled with a reagent may be attached to the reagent supply section 250 by opening the door 203. The cartridge 50 attached to the reagent supply section 250 may be extracted.

The exterior case 201 is formed of, for example, a SUS plate, and the pair of doors 202 and the door 203 are formed of a light-transmissive plastic plate such that the inside can be visually viewed.

As illustrated in FIG. 29, an opening 201f is provided on a rear surface part 201e of the exterior case 201. The opening 201f is open in the leftward-rightward direction (X direction) along the second frame 204b, and a tray 229 is inserted into the opening 201f so as to be extractable. The tray 229 is a part of the stage section 220, and, for example, even though the stage 210A is inclined, and thus the workpiece W mounted on the stage 210A falls down, the fallen workpiece W may be received by the tray 229 so as to be extracted out of the apparatus. Even though a cleaning liquid ejected onto the workpiece W in the cleaning section 230 or a reagent ejected onto the workpiece W from the cartridge 50 in the reagent supply section 250 runs to the stage 210A and leaks downward, the leaking cleaning liquid or reagent may be received by the tray 229 so as to be prevented from leaking to other portions.

Pathological Sample Manufacturing System

Figure 30:
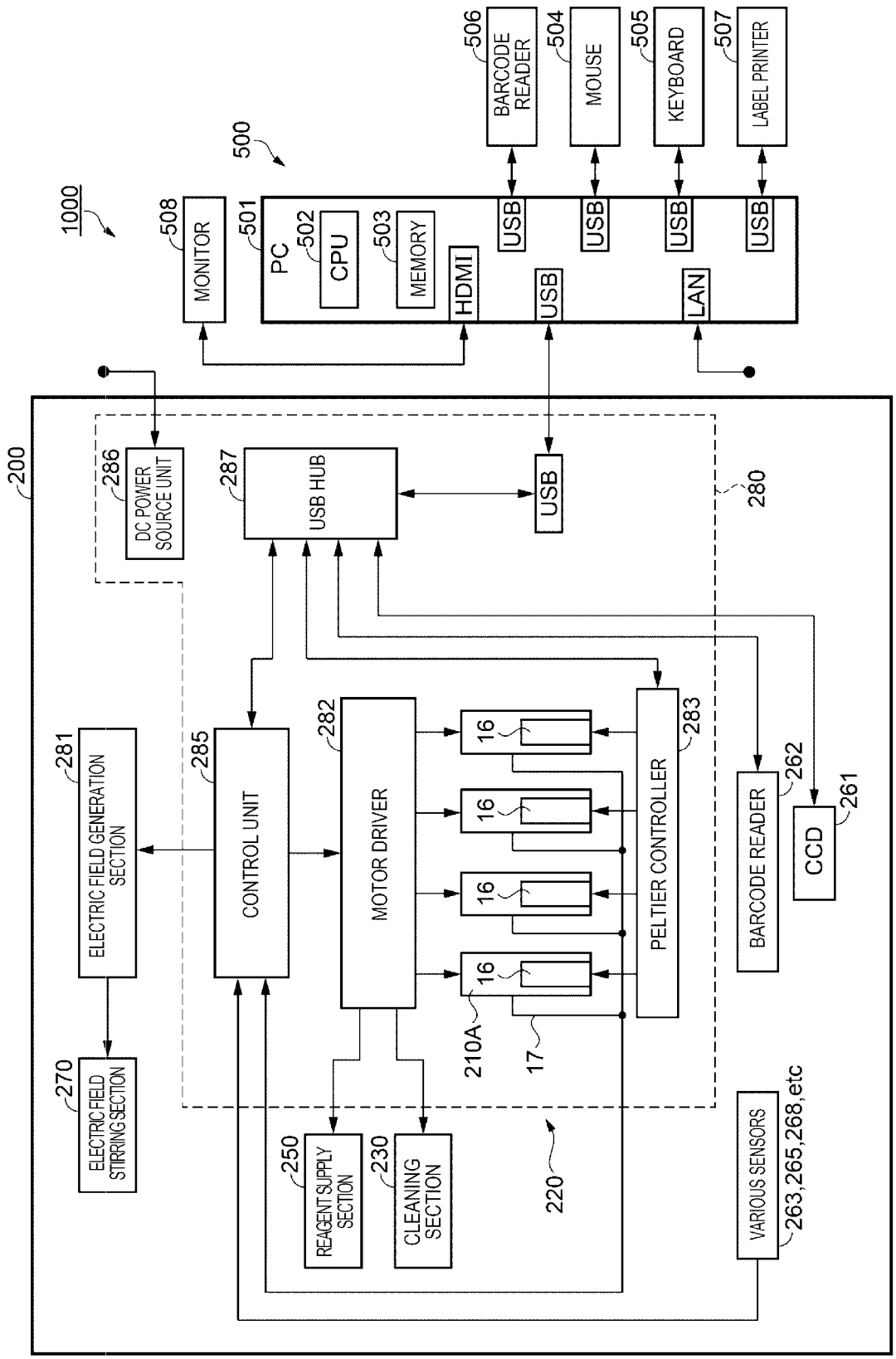
FIG. 30 is a block diagram illustrating an electrical and mechanical configuration of the pathological sample manufacturing apparatus.

Next, with reference to FIG. 30, a description will be made of a pathological sample manufacturing system using the pathological sample manufacturing apparatus 200 of the present embodiment. FIG. 30 is a block diagram illustrating an electrical and mechanical configuration of the pathological sample manufacturing apparatus. A pathological sample manufacturing system 1000 of the present embodiment uses the pathological sample manufacturing apparatus 200 and incorporates the feature thereof.

As illustrated in FIG. 30, the pathological sample manufacturing system 1000 of the present embodiment includes the pathological sample manufacturing apparatus 200, for example, a desktop computer 500, and peripheral devices coupled to the computer 500.

As described above, the pathological sample manufacturing apparatus 200 includes, as described above, the stage section 220, the cleaning section 230, the reagent supply section 250, the electric field stirring section 270, the circuit section 280, and the electric field generation section 281. The pathological sample manufacturing apparatus 200 includes the CCD 261 as an imaging portion, the barcode reader 262, and various sensors such as the residual quantity detection sensors 263 (263a and 263b) of the cartridge 50, the residual quantity detection sensors 265 related to the tanks 205 to 208, and the height detection sensor 268 of the cartridge 50. The circuit section 280 includes a motor driver 282, a Peltier controller 283, a control unit 285, a DC power source unit 286, and a USB hub 287.

As described above, the electric field generation section 281 is a device that generates an electric signal of which a voltage periodically changes, and that applies the electric signal to the upper electrode 272 of the electric field stirring section 270. The control unit 285 detects a potential of the electric signal generated by the electric field generation section 281, and controls the electric field generation section 281 such that the potential is within ±5% with respect to a preset potential. In FIG. 30, a detection unit detecting a potential of the electric signal generated by the electric field generation section 281 is not illustrated. The electric signal generated by the electric field generation section 281 is a rectangular wave of which a potential periodically changes between, for example, 0 V and 4 kV, and a cycle thereof is, for example, 5 Hz. The detection unit detects a potential of the rectangular wave in a state of being reduced to, for example, 1/1000, and feeds back a detection result to the control unit 285 at an interval of one cycle.

The motor driver 282 of the circuit section 280 is a circuit board mounted with circuits controlling driving of the motors included in the stage section 220, the cleaning section 230 including the channel switching mechanism 240, the reagent supply section 250, and the imaging unit 260. The Peltier element 16 as a heating element that heats the stage 210A and the temperature sensor 17 detecting a temperature of the stage 210A are attached to the stage 210A of the stage section 220. The Peltier controller 283 and the temperature sensor 17 are coupled to the control unit 285 via, for example, I/O ports. The Peltier controller 283 controls a current flowing through the Peltier element 16 based on a control signal from the control unit 285, and thus controls a temperature of the Peltier element 16. The Peltier controller 283 of the present embodiment includes a microcomputer related to control of a temperature of the Peltier element 16, but the microcomputer may be included in the control unit 285.

Various sensors such as the residual quantity detection sensors 263 and 265 are coupled to the control unit 285 via, for example, the I/O ports.

The CCD 261 or the barcode reader 262 is coupled to the control unit 285 via the USB hub 287. As described above, the CCD 261 is provided to image the workpiece W mounted on the stage 210A. The control unit 285 may acquire information regarding the tissue sample Ts fixed to the workpiece W based on image information of the workpiece W captured by the CCD 261.

The barcode reader 262 is provided to read a barcode assigned to the cartridge 50 mounted on the reagent supply section 250 as described above. The control unit 285 may acquire information regarding a reagent filling the cartridge 50 based on the barcode read by the barcode reader 262.

The circuit section 280 includes at least the motor driver 282, the Peltier controller 283, the control unit 285, the DC power source unit 286, and the USB hub 287. The DC power source unit 286 generates DC voltage required as power sources in the respective units of the circuit section 280 and the electric field generation section 281 by using AC power of 100 V supplied from the outside, and supplies the DC voltage thereto.

The control unit 285 is coupled to the computer 500 via the USB hub 287 and USB terminals. The computer 500 has a main body 501 including a CPU 502, a memory 503 as a storage unit, and terminals (HDMI (registered trademark), a LAN, and a USB) for coupling to various peripheral devices.

USB terminals may be coupled to a mouse 504 or a keyboard 505 related to an input operation on the computer 500. Other USB terminals may be coupled to a barcode reader 506 that is different from the barcode reader 262 provided in the pathological sample manufacturing apparatus 200, or a label printer 507. The HDMI terminal may be coupled to a monitor 508. In the present embodiment, not only an operation on the pathological sample manufacturing apparatus 200 but also communication with the computer 500 may be performed while checking information regarding a pathological sample manufacturing protocol displayed on the monitor 508. The monitor 508 may display various pieces of information sent from the computer 500. The LAN terminal is coupled to, for example, a network related to information management for a pathology department.

The barcode reader 506 is generally used to read a barcode assigned to a reagent container such as a bottle mainly storing a reagent. The computer 500 may acquire information regarding the reagent based on the read barcode, and may thus print a barcode label stuck to the cartridge 50 filled with the reagent by using the label printer 507.

Various pathological sample manufacturing protocols related to the pathological sample manufacturing method are stored in the memory 503 of the computer 500. The memory 503 storing the pathological sample manufacturing protocols may be an internal storage device such as a ROM, a RAM, or an HDD, and may be an external storage device that is coupled to the USB terminal and is used.

A worker may designate a pathological sample manufacturing protocol stored in the computer 500, and cause the computer 500 to control driving of the pathological sample manufacturing apparatus 200 such that a pathological sample is manufactured. A barcode of the cartridge 50 attached to the reagent supply section 250 may be actually read by the barcode reader 262, and thus the computer 500 may collate information regarding a reagent filling the cartridge 50 with information regarding a reagent in a pathological sample manufacturing protocol. Consequently, it is possible to thoroughly manage whether or not a reagent used to manufacture a pathological sample is correctly applied.

The computer 500 may acquire an image of the workpiece W captured by the CCD 261, and may perform an operation of correlating the image with a designated pathological sample manufacturing protocol. Consequently, it is possible to establish traceability of a pathological sample manufactured according to the designated pathological sample manufacturing protocol. In other words, it is possible to improve traceability of a pathological sample more than in a case of visual checking of a worker.

The computer 500 may acquire information regarding a residual quantity of a reagent stored in each cartridge 50 by using the residual quantity detection sensors 263. Therefore, even when there is a difference between a usage amount of a reagent obtained from a pathological sample manufacturing protocol and an actual usage amount, it is possible to appropriately and accurately manage replacement or the like of a reagent, that is, the cartridge 50.

The computer 500 may acquire information regarding an amount of a cleaning liquid such as distilled water or an amount of a waste liquid stored in the tanks 205 to 208 by using the residual quantity detection sensors 265. Therefore, even when there is a difference between a usage amount of a cleaning liquid such as distilled water obtained from a pathological sample manufacturing protocol and an actual usage amount, it is possible to appropriately and accurately manage the cleaning liquid. It is possible to appropriately and accurately manage amounts of waste liquids stored in the tanks 205 to 208.

The computer 500 is coupled to a network for a pathology department, and thus a series of information related to pathological sample manufacturing can be shared and managed. A configuration of the pathological sample manufacturing system 1000 is not limited thereto, and may include other apparatuses used for pathological diagnosis, such as an apparatus that subjects a staining state of tissue or a cell to image analysis. An uninterruptible power supply (UPS) device that can cope with power failure is preferably included.

Pathological Sample Manufacturing Method

Figure 31:
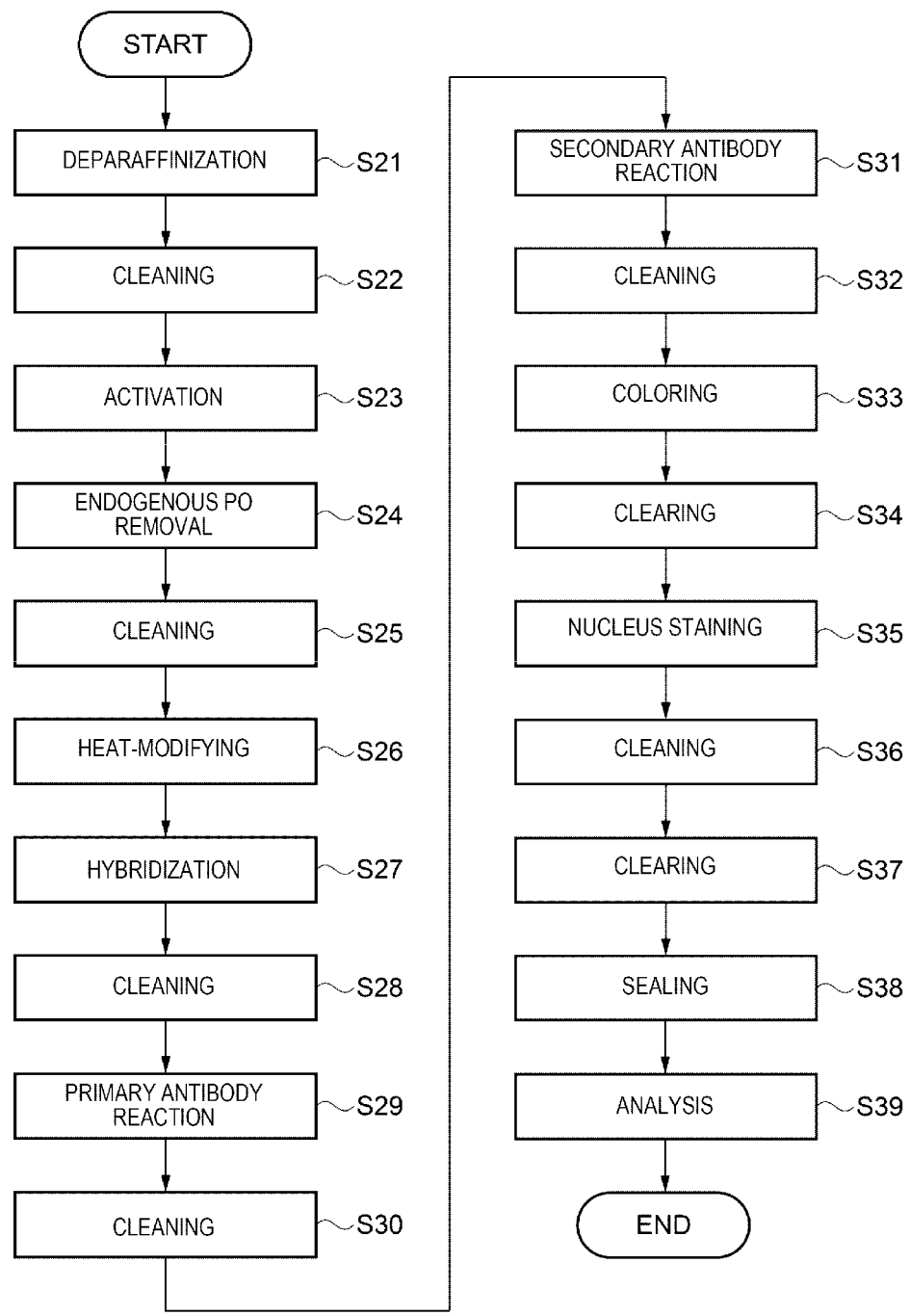
FIG. 31 is a flowchart illustrating a pathological sample manufacturing method in an ISH method.

Next, with reference to FIG. 31, a description will be made of an example of a pathological sample manufacturing method using the pathological sample manufacturing system 1000. FIG. 31 is a flowchart illustrating a pathological sample manufacturing method in an ISH method.

As illustrated in FIG. 31, an example of the pathological sample manufacturing method in the ISH method is a method using a section embedded in a paraffin, and includes step S21 of performing deparaffinization treatment; step S22 of cleaning the tissue sample Ts subjected to the deparaffinization treatment; step S23 of activating an antigen in the tissue sample Ts; step S24 of removing an endogenous PO of the activated tissue sample Ts; step S25 of cleaning the tissue sample Ts from which the endogenous PO is removed; step S26 of performing heat-modifying treatment on the tissue sample Ts; step S27 of performing hybridization; and step S28 of cleaning the tissue sample Ts subjected to the hybridization. The example of the pathological sample manufacturing method includes step S29 of performing a primary antibody reaction; step S30 of cleaning the tissue sample Ts subjected to the primary antibody reaction treatment; step S31 of performing a secondary antibody reaction; step S32 of cleaning the tissue sample Ts subjected to the secondary antibody reaction treatment; step S33 of coloring the cleaned tissue sample Ts; and step S34 of cleaning the colored tissue sample Ts. The example of the pathological sample manufacturing method includes step S35 of subjecting the cleaned tissue sample Ts to nucleus staining; step S36 of cleaning the tissue sample Ts subjected to the nucleus staining; step S37 of clearing the cleaned tissue sample Ts; step S38 of enclosing the cleared tissue sample Ts; and step S39 of checking the staining density of the enclosed tissue sample Ts through image analysis. The steps are stored in the memory 503 of the computer 500 as a pathological sample manufacturing protocol based on using of the pathological sample manufacturing system 1000. In each of step S24 to step S36, the computer 500 sends a control signal based on the pathological sample manufacturing protocol to the control unit 285 of the pathological sample manufacturing apparatus 200, and the control unit 285 controls driving of the pathological sample manufacturing apparatus 200 so as to perform the processes in step S24 to step S36.

In step S21 (deparaffinization process), a worker performs deparaffinization treatment by disposing a paraffin-embedded section of a pig liver block as the tissue sample Ts inside the water repellent ring 2 of the workpiece W, and then immersing the workpiece W in xylene for five minutes. The deparaffinization process is performed by immersing the workpiece W in each of two vessels storing the xylene for five minutes. In other words, the time required for the deparaffinization treatment is ten minutes. The worker performs the deparaffinization treatment using the xylene for ten minutes, and then immerses the workpiece W in ethanol for three minutes such that the xylene adhered to the workpiece W is replaced with the ethanol. A replacement process of replacing the xylene with the ethanol is performed by immersing the workpiece W in each of three vessels storing the ethanol for three minutes. In other words, the time required for the replacement treatment is nine minutes. The flow proceeds to step S22.

In step S22 (cleaning process), the worker pours distilled water over the workpiece W and thus washes the workpiece W. The flow proceeds to step S23.

In step S23 (activation process), the worker immerses the workpiece W in an activation liquid that is adjusted to pH9 and is heated to 98° C. for 15 minutes. The antigen of the tissue sample Ts is activated, and thus the antigen that hardly binds to an antibody due to immobilization is caused to easily bind. After the activation, the worker pours distilled water over the workpiece W. In step S21 to step S23, the worker performs each process without using the pathological sample manufacturing system 1000.

In step S24 (endogenous PO removal process), the worker mounts the workpiece W subjected to the activation treatment on the stage 210A of the pathological sample manufacturing apparatus 200. The control unit 285 controls driving of the motor 215 of the stage transport mechanism, and thus transports the stage 210A to the reagent supply section 250. In the reagent supply section 250, the control unit 285 controls driving of the motor 257 of the reagent supply section 250 based on the pathological sample manufacturing protocol, and thus transports the cartridge 50 filled with a reagent (hydrogen peroxide solution of 3% by volume) removing the endogenous PO to face the workpiece W. The control unit 285 controls driving of the electric pusher 258 and thus drops the reagent (hydrogen peroxide solution of 3% by volume) onto the workpiece W from the cartridge 50. An amount of the dropped reagent (hydrogen peroxide solution of 3% by volume) in this case is, for example, 100 μL. After a predetermined amount the reagent (hydrogen peroxide solution of 3% by volume) is supplied to the workpiece W, the control unit 285 controls driving of the motor 215 of the stage transport mechanism, and thus transports the stage 210A to a reaction position that is an intermediate position between the reagent supply section 250 and the cleaning section 230. The workpiece W stands still at the reaction position for five minutes, and endogenous PO is removed from the tissue sample Ts through blocking. The process proceeds to step S25.

In step S25 (cleaning process), the control unit 285 controls driving of the motor 215 of the stage transport mechanism, and thus transports the stage 210A from the reaction position to the cleaning section 230. In the cleaning section 230, the control unit 285 controls driving a valve related to a pump, ejects distilled water as a cleaning liquid stored in the tank 205 onto the workpiece W from the nozzle 231 such that the distilled water flows for 30 seconds, and thus performs cleaning. After the cleaning, the control unit 285 controls driving of the motor 215 of the stage transport mechanism, and thus transports the stage 210A to the reagent supply section 250. The control unit 285 controls driving of the motor 257 of the reagent supply section 250, causes the cartridge 50 filled with a reagent containing a proteolytic enzyme such as pepsin to face the stage 210A, and drops, for example, 50 μL of the reagent onto the tissue sample Ts of the workpiece W from the cartridge 50. The control unit 285 moves the stage 210A to the reaction position, then causes the stage 210A to stand still there for 5 to 30 minutes, and performs a treatment process for an enzyme to be reacted. Through the enzyme treatment process, permeability of a reagent (probe) into a target gene is increased, and a nonspecific reaction is reduced. After the enzyme treatment process is finished, the control unit 285 transports the stage 210A to the cleaning section 230, ejects distilled water as a cleaning liquid stored in the tank 205 onto the workpiece W from the nozzle 231 such that the distilled water flows for 30 seconds, and thus performs cleaning. After the workpiece W is firmly washed away with distilled water, air is blown from the nozzle 234 onto the workpiece W to blow away the residue of the distilled water. The flow proceeds to step S26.

In step S26 (heat-modifying process), the worker drops 10 microliters (μL) of a reagent (probe) onto the tissue sample Ts of the workpiece W subjected to the endogenous PO removal treatment and the enzyme treatment and mounted on the stage 210A by using a pipette. Successively, 30 μL of an oil is dropped by using a pipette. In other words, the reagent (probe) is coated with the oil, and thus transpiration of the reagent (probe) due to heating is prevented. In order to efficiently perform subsequent electric field stirring, the oil is added to the reagent (probe), and thus a volume of the droplet S is increased during the electric field stirring. The control unit 285 controls driving the motor 215 of the stage transport mechanism, and thus transports the stage 210A to the reaction position. The control unit 285 controls the Peltier controller 283 such that a current flows through the Peltier element 16, and thus heats the stage 210A to 80° C., and then causes the stage 210A to stand still for about five minutes. Thereafter, the control unit 285 stops flowing of a current to the Peltier element 16, and performs natural cooling until a temperature of the workpiece W becomes 37° C. The flow proceeds to step S27.

In step S27 (hybridization process), the control unit 285 controls driving the motor 215 of the stage transport mechanism, and thus transports the stage 210A to the electric field stirring section 270. The control unit 285 controls the Peltier controller 283 such that a current flows through the Peltier element 16, and thus heats the stage 210A to 37° C., and also generates an electric field between the lower electrode 210 and the upper electrode 272 so as to subject the droplet S containing the reagent (probe) and the oil to electric field stirring. During the electric field stirring in this case, the stage 210A is not moved in a state in which the lower electrode 210 and the upper electrode 272 are disposed to face each other. The time required for the electric field stirring is 180 minutes. Consequently, the tissue sample Ts (that is, single-stranded nucleic acid) subjected to the heat-modifying treatment and the reagent (probe) are reacted with each other, and thus hybridization (complementary binding reaction) is performed. The flow proceeds to step S28.

In step S28 (cleaning process), the control unit 285 controls driving of the motor 215 of the stage transport mechanism, and thus transports the stage 210A from the electric field stirring section 270 to the cleaning section 230. In the cleaning section 230, the control unit 285 controls driving a valve related to a pump, ejects a cleaning liquid (PBS-T) stored in the tank 206 onto the workpiece W from the nozzle 231 such that the cleaning liquid flows for 30 seconds, and thus performs cleaning. The cleaning liquid (PBS-T) is discharged to the tank 208. TBS-T may be used as a cleaning liquid. The control unit 285 transports the stage 210A to the reagent supply section 250, drops 100 μL of a standard-saline-citrate (SSC) solution onto the workpiece W from the cartridge 50 filled with the SSC solution, causes the stage 210A to stand still for five minutes, and cleans the tissue sample Ts. The control unit 285 transports the stage 210A to the cleaning section 230, and inclines the stage 210A to discharge the SSC solution. The control unit 285 transports the stage 210A to the reagent supply section 250 again, and drops 250 μL of the SSC solution onto the workpiece W from the cartridge 50 filled with the SSC solution. The control unit 285 moves the stage 210A to the reaction position, then controls the Peltier controller 283, causes a current to flow through the Peltier element 16 to heat the workpiece W to 75° C. to 80° C., and causes the stage 210A to standstill there for five minutes. Through standstill for five minutes, a probe that binds in a nonspecific manner is peeled. Thereafter, the control unit 285 transports the stage 210A to the cleaning section 230, ejects the cleaning liquid (PBS-T) stored in the tank 206 onto the workpiece W from the nozzle 231 such that the cleaning liquid flows for 30 seconds, and thus performs cleaning. In the cleaning section 230, cleaning for a total of one minute is performed, and thus the stage 210A is cooled. The flow proceeds to step S29.

In step S29 (primary antibody reaction process), the control unit 285 controls driving the motor 215 of the stage transport mechanism, and thus transports the stage 210A to the reagent supply section 250 from the cleaning section 230. In the reagent supply section 250, based on the pathological sample manufacturing protocol, the control unit 285 controls driving of the motor 257 of the reagent supply section 250, and thus transports the cartridge 50 filled with a primary antibody reagent (Hep-par1) to face the workpiece W. The control unit 285 controls driving of the electric pusher 258 and thus drops, for example, 30 μL of the primary antibody reagent onto the workpiece W from the cartridge 50. Next, the control unit 285 controls driving of the motor 257 of the reagent supply section 250, and thus transports the cartridge 50 filled with an oil (liquid paraffin) as a reagent to face the workpiece W. The control unit 285 controls driving of the electric pusher 258 and thus drops the oil onto the workpiece W from the cartridge 50. An amount of the dropped oil in this case is, for example, 30 μL. In other words, the primary antibody reagent is coated with the oil, and thus transpiration of the primary antibody reagent is prevented. In order to efficiently perform subsequent electric field stirring, the oil is added to the primary antibody reagent, and thus a volume of the droplet S is increased during the electric field stirring. Thereafter, the control unit 285 controls driving the motor 215 of the stage transport mechanism, and thus transports the stage 210A to the electric field stirring section 270 from the reagent supply section 250. In the electric field stirring section 270, the control unit 285 generates an electric field between the lower electrode 210 and the upper electrode 272, and thus stirs the droplet S containing the primary antibody reagent and the oil supplied to the workpiece W. In this case, the control unit 285 controls driving of the motor 215 of the stage transport mechanism, and thus reciprocally moves the stage 210A relative to the origin in the electric field stirring. The time required for the electric field stirring is 20 minutes. The flow proceeds to step S30.

In step S30 (cleaning process), the control unit 285 controls driving of the motor 215 of the stage transport mechanism, and thus transports the stage 210A from the electric field stirring section 270 to the cleaning section 230. In the cleaning section 230, in the same manner as in step S28, the PBS-T is caused to flow, and thus cleaning is performed. The flow proceeds to step S31.

In step S31 (secondary antibody reaction process), the control unit 285 controls driving the motor 215 of the stage transport mechanism, and thus transports the stage 210A to the reagent supply section 250 from the cleaning section 230. In the reagent supply section 250, based on the pathological sample manufacturing protocol, the control unit 285 controls driving of the motor 257 of the reagent supply section 250, and thus transports the cartridge 50 filled with a secondary antibody reagent (Envision+Dual Link) to face the workpiece W. The control unit 285 controls driving of the electric pusher 258 and thus drops, for example, 30 μL of the secondary antibody reagent onto the workpiece W from the cartridge 50. Next, the control unit 285 controls driving of the motor 257 of the reagent supply section 250, and thus transports the cartridge 50 filled with an oil (liquid paraffin) as a reagent to face the workpiece W. The control unit 285 controls driving of the electric pusher 258 and thus drops the oil onto the workpiece W from the cartridge 50. An amount of the dropped oil in this case is, for example, 30 μL. In other words, the secondary antibody reagent is coated with the oil, and thus transpiration of the secondary antibody reagent is prevented. In order to efficiently perform subsequent electric field stirring, the oil is added to the secondary antibody reagent, and thus a volume of the droplet S is increased during the electric field stirring. Thereafter, the control unit 285 controls driving the motor 215 of the stage transport mechanism, and thus transports the stage 210A to the electric field stirring section 270 from the reagent supply section 250. In the electric field stirring section 270, the control unit 285 generates an electric field between the lower electrode 210 and the upper electrode 272, and thus stirs the droplet S containing the secondary antibody reagent and the oil supplied to the workpiece W. In this case, the control unit 285 controls driving of the motor 215 of the stage transport mechanism, and thus reciprocally moves the stage 210A relative to the origin in the electric field stirring. The time required for the electric field stirring is 20 minutes. The flow proceeds to step S32.

In step S32 (cleaning process), the control unit 285 controls driving of the motor 215 of the stage transport mechanism, and thus transports the stage 210A from the electric field stirring section 270 to the cleaning section 230. In the cleaning section 230, in the same manner as in step S28, the PBS-T is caused to flow, and thus cleaning is performed. The flow proceeds to step S33.

In step S33 (coloring process), the control unit 285 controls driving the motor 215 of the stage transport mechanism, and thus transports the stage 210A to the reagent supply section 250 from the cleaning section 230. In the reagent supply section 250, based on the pathological sample manufacturing protocol, the control unit 285 controls driving of the motor 257 of the reagent supply section 250, and thus transports the cartridge 50 filled with a coloring reagent (DAB) to face the workpiece W. The control unit 285 controls driving of the electric pusher 258 and thus drops the reagent (DAB) onto the workpiece W from the cartridge 50. An amount of the dropped reagent (DAB) in this case is, for example, 60 μL. After a predetermined amount of the reagent (DAB) is supplied to the workpiece W, the stage 210A stands still there for three minutes, and thus the tissue sample Ts and the reagent (DAB) are reacted with each other such that a color is developed. The flow proceeds to step S34.

In step S34 (cleaning process), the control unit 285 controls driving of the motor 215 of the stage transport mechanism, and thus transports the stage 210A from the reagent supply section 250 to the cleaning section 230. In the cleaning section 230, the control unit 285 controls driving a valve related to a pump, ejects the distilled water stored in the tank 205 onto the workpiece W from the nozzle 231 such that the distilled water flows for two minutes. In the cleaning section 230, the control unit 285 controls driving of the stage inclination mechanism, and thus supplies the distilled water to the workpiece W to be cleaned in a state in which the stage 210A is inclined. The distilled water containing the reagent (DAB) containing a carcinogen is discharged to the tank 208 from the inclined workpiece W via the liquid discharge guide portion 226 by the channel switching mechanism 240. The flow proceeds to step S35.

In step S35 (nucleus staining process), the control unit 285 controls driving the motor 215 of the stage transport mechanism, and thus transports the stage 210A to the reagent supply section 250 from the cleaning section 230. In the reagent supply section 250, based on the pathological sample manufacturing protocol, the control unit 285 controls driving of the motor 257 of the reagent supply section 250, and thus transports the cartridge 50 filled with a reagent (hematoxylin) for nucleus staining (counter staining) to face the workpiece W. The control unit 285 controls driving of the electric pusher 258 and thus drops the reagent (hematoxylin) onto the workpiece W from the cartridge 50. An amount of the dropped reagent (hematoxylin) in this case is, for example, 100 μL. After a predetermined amount of the reagent (hematoxylin) is supplied to the workpiece W, the stage 210A stands still there for one minute, and thus the tissue sample Ts and the reagent (hematoxylin) are reacted with each other such that nucleus staining (counter staining) is performed. The flow proceeds to step S36.

In step S36 (cleaning process), the control unit 285 controls driving of the motor 215 of the stage transport mechanism, and thus transports the stage 210A from the reagent supply section 250 to the cleaning section 230. In the cleaning section 230, the control unit 285 controls driving a valve related to a pump, ejects the distilled water stored in the tank 205 onto the workpiece W from the nozzle 231 such that the distilled water flows for two minutes. In the cleaning section 230, the distilled water is supplied to the workpiece W to be cleaned in a state in which the stage 210A is inclined by the stage inclination mechanism. The distilled water containing the reagent (hematoxylin) is discharged to the tank 207 from the inclined workpiece W via the liquid discharge guide portion 226 by the channel switching mechanism 240. The control unit 285 controls driving the motor 215 of the stage transport mechanism, and thus transports the stage 210A to the origin from the cleaning section 230. The flow proceeds to step S37.

In step S37 (clearing process), in order to further improve a contrast ratio in staining of the tissue sample Ts subjected to the nucleus staining by extracting the workpiece W from the stage 210A, a dehydration treatment of removing moisture from the tissue sample Ts by using ethanol and a clearing treatment to improve the clearness of the tissue sample Ts by replacing ethanol with xylene are performed. Specifically, five vessels storing absolute ethanol (99.5% by volume or more) and five vessels storing xylene are prepared, and the workpiece W is immersed in each of a total of ten vessels in order from the absolute ethanol for 10 seconds. Therefore, the time required for immersion is 100 seconds. The flow proceeds to step S38. In the dehydration treatment, five vessels for ethanol of which a concentration changes stepwise from 75% by volume to 99.5% by volume may be used.

In step S38 (sealing process), in order to prevent the tissue sample Ts subjected to the clearing treatment from being dried, a water-insoluble sealing agent is dropped onto the workpiece W such that sealing treatment of covering the tissue sample Ts with cover glass is performed. The time required for the sealing treatment is about one minute. The flow proceeds to step S39.

In step S39 (analysis process), the tissue sample Ts subjected to the clearing treatment is imaged by using an image analysis apparatus having an imaging unit, and staining density is checked through image analysis. The time required for the analysis treatment is about one minute. The tissue sample Ts with a positive finding and the tissue sample Ts with a negative finding are prepared, staining densities thereof are compared with each other through image analysis, and thus pathological diagnosis is performed.

According to the pathological sample manufacturing in the ISH method exemplified in the present embodiment, in the primary antibody reaction process of step S29 and the secondary antibody reaction process of step S31, the primary antibody reagent and the secondary antibody reagent are efficiently and uniformly subjected to electric field stirring, and a reaction progresses, and thus a coloring state with less coloring unevenness is obtained in the coloring process of step S33. When the pathological sample manufacturing system 1000 is used, a pathological sample can be manufactured not only according to the ISH method but also according to the IHC method.

The present disclosure is not limited to the embodiments, and various changes or alterations may be added to the embodiments. Hereinafter, modification examples will be described.

Modification Example 1

In the electric field stirring apparatus 100 of the first embodiment, a sectional shape of the groove 20b formed on the electrode surface 20a of the second electrode 20 is a quadrilateral shape as illustrated in FIG. 3B, but is not limited thereto. For example, a sectional shape of the groove 20b may be a polygonal shape such as a triangular shape in which a width is reduced toward the bottom, or a circular arc shape. Such a form of the groove 20b of the second electrode 20 may be applied to the upper electrode 272 of the electric field stirring section 270 of the pathological sample manufacturing apparatus 200 according to the second embodiment.

Modification Example 2

The electric field stirring apparatus 100 of the first embodiment may include an inter-electrode distance adjustment mechanism that adjusts the inter-electrode distance d between the first electrode 10 and the second electrode 20 disposed to face each other in the upward-downward direction. The inter-electrode distance adjustment mechanism of the electric field stirring apparatus 100 is configured to move, for example, the electrode support portion 21 supporting the second electrode 20 in the upward-downward direction. This is also the same for the pathological sample manufacturing apparatus 200 of the second embodiment, and an inter-electrode distance adjustment mechanism that moves the electrode support portion 271 supporting the plurality of upper electrodes 272 in the upward-downward direction may be provided in the third frame 204c. According to this configuration, the droplet S can be adjusted not to come into contact with the second electrode 20 or the upper electrode 272 functioning as the second electrode during electric field stirring due to physical property such as an amount, viscosity, or surface tension of the droplet S formed on the workpiece W.

Modification Example 3

In the pathological sample manufacturing according to the IHC method or the ISH method, a reagent used in a single process is not limited to one type of reagent. For example, in the coloring process, a coloring buffer reagent (DAB1) and a concentrated coloring reagent (DAB2) may be used. A ratio between the DAB1 and the DAB2 is set as appropriate. In a case where a plurality of types of reagents are used as mentioned above, it is necessary to mix the plurality of dropped reagents with each other well. In this case, the stage 210A may be slightly reciprocally moved in the front-rear direction by using the stage transport mechanism such that the plurality of types of reagents dropped onto the workpiece W are mixed with each other.

Hereinafter, contents derived from the embodiments will be described.

An electric field stirring apparatus of the present specification is an apparatus in which a liquid disposed between a first electrode and a second electrode disposed to face each other is vibrated and stirred by an electric field generated between the first electrode and the second electrode, the second electrode having a groove formed along a first direction on an electrode surface facing the first electrode, includes a movement mechanism that reciprocally moves at least one of the first electrode and the second electrode relative to the other electrode in a second direction intersecting the first direction in a state in which the first electrode and the second electrode face each other during a period in which the electric field is generated.

According to the configuration of the present specification, when the first electrode and the second electrode are disposed to face each other, a first portion in which an inter-electrode distance from the first electrode is set to a predetermined distance and a second portion longer than the first portion are generated in the portion of the groove formed along the first direction in the second electrode. Therefore, when an electric field is generated between the first electrode and the second electrode, an intensity of an electric field generated in the second portion is lower than an intensity of an electric field generated in the first portion. When a liquid is stirred under a situation of such electric field intensities, vibration of the liquid due to the electric field is increased more than in a case where the liquid is stirred at a constant electric field intensity. When one of the first electrode and the second is reciprocally moved relative to the other electrode in the second direction intersecting the first direction by the movement mechanism in a state in which the first electrode and the second electrode face each other, a position of the node, when a liquid is vibrated due to an electric field swings in the second direction. Since weaker stirring occurs in a node portion in vibration of a liquid than in other portions, a position of the node in vibration is caused to swing in the second direction, and thus the liquid can be uniformly stirred compared with a case where a position of the node in vibration of the liquid is constant. In other words, in immunostaining or ISH, it is possible to provide the electric field stirring apparatus capable of suppressing coloring unevenness caused by a reaction by uniformly stirring a reagent as a liquid and reacting the reagent with a tissue sample.

In the electric field stirring apparatus, preferably, the liquid is disposed in a predetermined region on one surface of a substrate, the first electrode has a mounting portion on which the substrate is mounted, and, when a position where a center of the predetermined region of the substrate mounted on the mounting portion of the first electrode faces a center of the groove of the second electrode is set as an origin in the second direction, the movement mechanism reciprocally moves the one electrode in the second direction relative to the other electrode to a position where an inner edge of the predetermined region is deviated relative to the origin. According to the configuration, an intensity of an electric field generated between the center of the groove of the second electrode and the first electrode is much weaker than other portions of the second electrode. Therefore, the portion where the electric field intensity between the first electrode and the second electrode is the weakest is moved to the end of the predetermined region in which the liquid is disposed by the movement mechanism. In other words, the portion where the electric field intensity other than the center of the groove is strong in the predetermined region in which the liquid is disposed is moved in the second direction, and thus it is possible to uniformly stir the liquid disposed in the predetermined region. Since the mounting portion is provided on the first electrode, the liquid can be stirred by disposing the substrate at a constant position on the first electrode.

In the electric field stirring apparatus, a plurality of the grooves may be formed with a predetermined arrangement pitch in the second direction on the electrode surface of the second electrode, and the predetermined region in which the liquid is disposed may be provided in a plurality with the predetermined arrangement pitch in the second direction on the one surface of the substrate. According to the configuration, it is possible to uniformly stir a liquid disposed in each of the plurality of regions on one surface of the substrate, by using an electric field.

The electric field stirring apparatus preferably further includes an electric field generation section that periodically applies a voltage between the first electrode and the second electrode so as to generate an electric field; a detection section that detects the voltage applied between the first electrode and the second electrode; and a control section, and the control section preferably controls the electric field generation section such that a value of the voltage detected by the detection section is included in a predetermined range. When a voltage is periodically applied between the first electrode and the second electrode, so as to generate an electric field, and a liquid is stirred, there is concern that a temperature of the liquid may be increased during stirring, and thus a potential of the voltage applied between the first electrode and the second electrode may be substantially reduced. According to the configuration, the control section controls the electric field generation section such that a value of the voltage applied between the first electrode and the second electrode, detected by the detection section is included in a predetermined range. Therefore, since a voltage is reliably applied between the first electrode and the second electrode so as to generate a stable electric field, it is possible to efficiently stir a liquid.

In the electric field stirring apparatus, the predetermined range of the value of the voltage is preferably ±5% of a predetermined voltage value.

An electric field stirring method of the present specification includes an electric field stirring step in which a liquid disposed between a first electrode and a second electrode disposed to face each other is vibrated and stirred by an electric field generated between the first electrode and the second electrode, in which the second electrode has a groove formed along a first direction on an electrode surface facing the first electrode, and, in which, in the electric field stirring step, at least one of the first electrode and the second electrode is reciprocally moved relative to the other electrode in a second direction intersecting the first direction in a state in which the first electrode and the second electrode face each other during a period in which the electric field is generated.

According to the method of the present specification, when the first electrode and the second electrode are disposed to face each other, a first portion in which an inter-electrode distance from the first electrode is set to a predetermined distance and a second portion longer than the first portion are generated in the portion of the groove formed along the first direction in the second electrode. Therefore, when an electric field is generated between the first electrode and the second electrode, an intensity of an electric field generated in the second portion is lower than an intensity of an electric field generated in the first portion. When a liquid is stirred under a situation of the electric field intensities, vibration of the liquid due to the electric field is increased more than in a case where the liquid is stirred at a constant electric field intensity. When one of the first electrode and the second electrode is reciprocally moved relative to the other in the second direction intersecting the first direction in a state in which the first electrode and the second electrode face each other during a period in which an electric field is generated, a position of the node, when a liquid is vibrated due to the electric field swings in the second direction. Since weaker stirring occurs in a node portion in vibration of a liquid than in other portions, a position of the node in vibration is caused to swing in the second direction, and thus the liquid can be uniformly stirred compared with a case where a position of the node in vibration of the liquid is constant. In other words, in immunostaining or ISH, it is possible to provide the electric field stirring method capable of suppressing coloring unevenness caused by a reaction by uniformly stirring a reagent as a liquid and reacting the reagent with a tissue sample.

In the electric field stirring method, preferably, the liquid is disposed in a predetermined region on one surface of a substrate, and, in the electric field stirring step, when a position where a center of the predetermined region of the substrate mounted on the first electrode faces a center of the groove of the second electrode is set as an origin in the second direction, the one electrode is reciprocally moved in the second direction relative to the other electrode to a position where an outer edge of the predetermined region is deviated relative to the origin. According to the configuration, an intensity of an electric field generated between the center of the groove of the second electrode and the first electrode is much weaker than other portions of the second electrode. Therefore, one electrode is reciprocally moved in the second direction relative to the other electrode, and thus the portion where the electric field intensity between the first electrode and the second electrode is much weakest is moved to the end of the predetermined region in which the liquid is disposed. In other words, the portion where the electric field intensity other than the center of the groove is strong in the predetermined region in which the liquid is disposed is moved in the second direction, and thus it is possible to uniformly stir the liquid disposed in the predetermined region.

In the electric field stirring method, a plurality of the grooves may be formed with a predetermined arrangement pitch in the second direction on the electrode surface of the second electrode, and the predetermined region in which the liquid is disposed may be provided in a plurality with the predetermined arrangement pitch in the second direction on the one surface of the substrate. According to the method, it is possible to uniformly stir a liquid disposed in each of the plurality of regions on one surface of the substrate, by using an electric field.

In the electric field stirring method, preferably, in the electric field stirring step, a voltage is periodically applied between the first electrode and the second electrode so as to generate an electric field, and the voltage is applied such that a value of the voltage applied between the first electrode and the second electrode is included in a predetermined range. In the electric field stirring step, when a voltage is periodically applied between the first electrode and the second electrode, so as to generate an electric field, and a liquid is stirred, there is concern that a temperature of the liquid may be increased during stirring, and thus a potential of the voltage applied between the first electrode and the second electrode may be substantially reduced. According to the method, the voltage is applied such that a value of the voltage applied between the first electrode and the second electrode is included in a predetermined range. Therefore, since a voltage is reliably applied between the first electrode and the second electrode so as to generate a stable electric field, it is possible to efficiently stir a liquid.

A pathological sample manufacturing apparatus of the present specification includes the electric field stirring apparatus; a stage section that includes a stage which functions as the first electrode of the electric field stirring apparatus and on which a substrate with a tissue sample fixed to a predetermined region is mounted; a reagent supply section that supplies a reagent to the substrate mounted on the stage; a cleaning section that supplies a cleaning liquid to the substrate mounted on the stage; a stage transport mechanism that functions as the movement mechanism of the electric field stirring apparatus when the cleaning section, the reagent supply section, and the electric field stirring apparatus are disposed in the second direction, and moves the stage in the second direction; and a control unit, in which, based on a pathological sample manufacturing protocol, the control unit controls driving of the stage transport mechanism, thus moves the stage to a position facing the second electrode of the electric field stirring apparatus, and subjects the reagent or the cleaning liquid supplied to the substrate to electric field stirring.

According to the configuration of the present specification, it is possible to uniformly stir a reagent supplied from the reagent supply section or a cleaning liquid supplied from the cleaning section, with the electric field stirring apparatus. Therefore, when the pathological sample manufacturing apparatus is used for immunostaining or ISH, it is possible to provide the pathological sample manufacturing apparatus capable of suppressing coloring unevenness by uniformly reacting pathological tissue with a reagent and enabling appropriate pathological diagnosis to be performed.

The pathological sample manufacturing apparatus preferably further includes a plurality of stage sections, the stage transport mechanism is preferably provided to correspond to each of the plurality of stage sections, and the second electrode of the electric field stirring apparatus is preferably separately provided for each of the plurality of stage sections. According to the configuration, it is possible to efficiently manufacture a plurality of pathological samples with a single pathological sample manufacturing apparatus. Since the second electrode of the electric field stirring apparatus is separately provided for each of the plurality of stage sections, it is possible to reduce a variation in an electric field generation intensity among the plurality of stage sections compared with a case where the second electrode is provided in common to the plurality of stage sections.

The pathological sample manufacturing apparatus preferably further includes a probe that is brought into contact with the stage transported to the electric field stirring apparatus by the stage transport mechanism, and applies a potential for generating an electric field, and the electric field stirring apparatus preferably includes a probe movement mechanism that reciprocally moves the probe in the second direction in a state in which the probe is brought into contact with the stage. According to the configuration, since the probe movement mechanism is provided which reciprocally moves the probe in the second direction in a state in which the probe is brought into contact with the stage even though the stage section is reciprocally moved in the second direction by the stage transport mechanism functioning as a movement mechanism, it is possible to stably generate an electric field between the stage functioning as the first electrode and the second electrode. In other words, a structure of the stage transport mechanism is simplified compared with a case where a wiring is provided to directly apply a potential to the stage in order to generate an electric field.

What is claimed is:

1. A pathological sample manufacturing apparatus comrpsing:
   an electric field stirring apparatus in which a liquid disposed between a first electrode and a second electrode disposed to face each other is vibrated and stirred by an electric field generated between the first electrode and the second electrode, the second electrode having a groove formed along a first direction on an electrode surface facing the first electrode, the electric field stirring apparatus including a movement mechanism that reciprocally moves at least one of the first electrode and the second electrode relative to the other electrode in a second direction intersecting the first direction in a state in which the first electrode and the second electrode face each other during a period in which the electric field is generated;
   a stage section that includes a stage which functions as the first electrode of the electric field stirring apparatus and on which a substrate with a tissue sample fixed to a predetermined region is mounted;
   a reagent supply section that supplies a reagent to the substrate mounted on the stage;
   a cleaning section that supplies a cleaning liquid to the substrate mounted on the stage;
   a stage transport mechanism that functions as the movement mechanism of the electric field stirring apparatus when the cleaning section, the reagent supply section, and the electric field stirring apparatus are disposed in the second direction, and moves the stage in the second direction; and
   a control unit, wherein based on a pathological sample manufacturing protocol, the control unit controls driving of the stage transport mechanism, thus moves the stage to position facing the second electrode of the electric field stirring apparatus, and subjects the reagent or the cleaning liquid supplied to the substrate to electric field stirring.

2. The pathological sample manufacturing apparatus according to claim 1, wherein
   the liquid is disposed in a predetermined region on one surface of a substrate, the first electrode has a mounting portion on which the substrate is mounted, and when a position where a center of the predetermined region of the substrate mounted on the mounting portion of the first electrode faces a center of the groove of the second electrode is set as an origin in the second direction, the movement mechanism reciprocally moves the one electrode in the second direction relative to the other electrode to a position where an inner edge of the predetermined region is deviated relative to the origin.

3. The pathological sample manufacturing apparatus according to claim 2, wherein a plurality of the grooves are formed with a predetermined arrangement pitch in the second direction on the electrode surface of the second electrode, and the predetermined region in which the liquid is disposed is provided in a plurality with the predetermined arrangement pitch in the second direction on the one surface of the substrate.

4. The pathological sample manufacturing apparatus according to claim 1, further comprising:

an electric field generation section that periodically applies a voltage between the first electrode and the second electrode so as to generate an electric field;

a detection section that detects the voltage applied between the first electrode and the second electrode; and a control section, wherein the control section controls the electric field generation section such that a value of the voltage detected by the detection section is included in a predetermined range.

5. The pathological sample manufacturing apparatus according to claim 4, wherein the predetermined range of the value of the voltage is ±5% of a predetermined voltage value.

6. The pathological sample manufacturing apparatus according to claim 1, wherein a plurality of the stage sections are provided, the stage transport mechanism is provided to correspond to each of the plurality of stage sections, and the second electrode of the electric field stirring apparatus is separately provided for each of the plurality of stage sections.

7. The pathological sample manufacturing apparatus according to claim 1, further comprising:

a probe that is brought into contact with the stage transported to the electric field stirring apparatus by the stage transport mechanism, and applies a potential for generating an electric field, wherein the electric field stirring apparatus includes a probe movement mechanism that reciprocally moves the probe in the second direction in a state in which the probe is brought into contact with the stage.

8. An electric field stirring method comprising:

an electric field stirring step of vibrating and stirring a liquid disposed between a first electrode and a second electrode disposed to face each other with an electric field generated between the first electrode and the second electrode, wherein the second electrode has a groove formed along a first direction on an electrode surface facing the first electrode, and in the electric field stirring step, at least one of the first electrode and the second electrode is reciprocally moved relative to the other electrode in a second direction intersecting the first direction in a state in which the first electrode and the second electrode face each other during a period in which the electric field is generated.

9. The electric field stirring method according to claim 8, wherein the liquid is disposed in a predetermined region on one surface of a substrate, and in the electric field stirring step, when a position where a center of the predetermined region of the substrate mounted on the first electrode faces a center of the groove of the second electrode is set as an origin in the second direction, the one electrode is reciprocally moved in the second direction relative to the other electrode to a position where an outer edge of the predetermined region is deviated relative to the origin.

10. The electric field stirring method according to claim 9, wherein a plurality of the grooves are formed with a predetermined arrangement pitch in the second direction on the electrode surface of the second electrode, and the predetermined region in which the liquid is disposed is provided in a plurality with the predetermined arrangement pitch in the second direction on the one surface of the substrate.

11. The electric field stirring method according to claim 8, wherein in the electric field stirring step, a voltage is periodically applied between the first electrode and the second electrode so as to generate an electric field, and the voltage is applied such that a value of the voltage applied between the first electrode and the second electrode is included in a predetermined range.

* * * * *